(12) United States Patent
Ehrenfreund et al.

(10) Patent No.: US 7,531,559 B2
(45) Date of Patent: May 12, 2009

(54) FUNGICIDAL 1,2,3 TRIAZOLE DERIVATIVES

(75) Inventors: Josef Ehrenfreund, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 410 days.

(21) Appl. No.: 10/524,721

(22) PCT Filed: Aug. 18, 2003

(86) PCT No.: PCT/EP03/09111

§ 371 (c)(1),
(2), (4) Date: Feb. 16, 2005

(87) PCT Pub. No.: WO2004/018438

PCT Pub. Date: Mar. 4, 2004

(65) Prior Publication Data

US 2006/0154967 A1    Jul. 13, 2006

(30) Foreign Application Priority Data

Aug. 22, 2002   (GB) ................... 0219612.9
May 7, 2003     (GB) ................... 0310464.3

(51) Int. Cl.
*A61K 31/41* (2006.01)
*C07D 249/00* (2006.01)

(52) U.S. Cl. ...................... 514/359; 548/255
(58) Field of Classification Search ............ 514/359; 548/255
See application file for complete search history.

(56) References Cited

U.S. PATENT DOCUMENTS 4,233,059 A    11/1980   Krueger et al.

FOREIGN PATENT DOCUMENTS

| CH | 631602 | 8/1982 |
|----|--------|--------|
| DE | 1914954 | * 10/1969 |
| EP | 0019742 | 12/1980 |
| GB | 1215066 | 12/1970 |
| WO | 0009482 | 2/2000 |
| WO | 0149664 | 7/2001 |
| WO | 2004035589 | 4/2004 |

OTHER PUBLICATIONS

Copending U.S. Appl. Nos. 10/569,343 and 10/554,336.*

Romagnoli et al., Mycopathologia, vol. 153, pp. 129-132, 2001, especially p. 129.*
Romagnoli, et al., Mycopathologia, 153, 2001, 129-132, especially p. 130.*

* cited by examiner

Primary Examiner—Golam M. M. Shameem
Assistant Examiner—Susannah Chung
(74) Attorney, Agent, or Firm—Thomas Hamilton

(57) ABSTRACT

A compound of formula (I):, where A is an ortho-substituted ring selected from a number of specified rings; $R^1$ is halogen, cyano, nitro, $C_{1-4}$ alkyl, $C_{1-4}$ haloalkyl, $C_{1-4}$ alkoxy or $C_{1-4}$ haloalkoxy or optionally substituted $C_{2-4}$ alkenyl, optionally substituted $C_{2-4}$ alkynyl or optionally substituted $SO2(C_{1-4}$ alkyl) (where the optionally substituted moieties may each have up to 3 substituents, each independently selected from halogen and $C_{1-4}$ alkoxy); $R^2$ is $C_{1-4}$ alkyl, $C_{1-4}$ haloalkyl, $C_{1-4}$ alkoxy($C_{1-4}$)alkyl or $C_{1-4}$ alkylthio($C_{1-4}$)alkyl or [optionally substituted aryl]($C_{1-4}$)alkyl- or [optionally substituted aryl]oxy($C_{1-4}$)alkyl (where the optionally substituted aryl moieties may each have up to 3 substituents, each independently selected from halogen and $C_{1-4}$ alkoxy); $R^3$ is hydrogen, $CH_2C{=}CR^4$, $CH_2CR^4{=}C(H)R^4$, $CH{=}C{=}CH_2$ or $COR^5$ or optionally substituted $C_{1-4}$ alkyl, optionally substituted $C_{1-4}$ alkoxy or optionally substituted $(C_{1-4})$alkylC($=$O)O (where the optionally substituted moieties may each have up to 3 substituents, each independently selected from halogen and $C_{1-4}$ alkoxy, $C_{1-4}$ alkyl, $C_{1-2}$ haloalkoxy, hydroxy, cyano, carboxyl, methoxycarbonyl, ethoxycarbonyl, methylsulfonyl and ethylsulfonyl); each $R^4$ is, independently, hydrogen, halogen, $C_{1-4}$ alkyl, $C_{1-4}$ haloalkyl, $C_{1-4}$ alkoxy or $C_{1-4}$ alkoxy($C_{1-4}$)alkyl; and $R^5$ is hydrogen or optionally substituted $C_{1-6}$ alkyl, optionally substituted $C_{1-4}$ alkoxy, optionally substituted $C_{1-4}$ alkoxy($C_{1-4}$)alkyl, optionally substituted $C_{1-4}$ alkylthio($C_{1-4}$)alkyl or optionally substituted aryl (where the optionally substituted moieties may each have up to 3 substituents, each independently selected from halogen, $C_{1-6}$ alkoxy, $C_{1-6}$ haloalkoxy, cyano, hydroxy, methoxycarbonyl and ethoxycarbonyl).

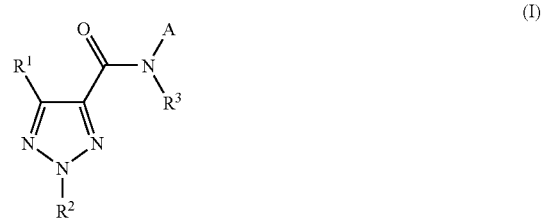

(I)

7 Claims, No Drawings

FUNGICIDAL 1,2,3 TRIAZOLE DERIVATIVES

This application is a 371 of International Application No. PCT/EP2003/009111 filed Aug. 18, 2003, which claims priority to GB 0219612.9, filed Aug. 22, 2002, and GB 0310464.3 filed May 7, 2003, the contents of which are incorporated herein by reference.

The present invention relates to novel 1,2,3-triazole derivatives which have microbiocidal activity, in particular fungicidal activity. The invention also relates to novel intermediates used in the preparation of these compounds, to agrochemical compositions which comprise at least one of the novel compounds as active ingredient and to the use of the active ingredients or compositions in agriculture or horticulture for controlling or preventing infestation of plants by phytopathogenic microorganisms, preferably fungi.

The present invention provides a compound of formula (I):

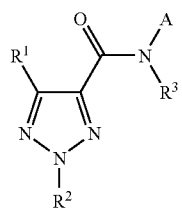
(I)

where A is an ortho-substituted ring selected from formulae (A1) to (A22);

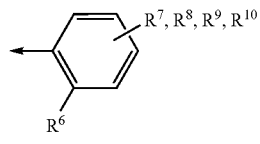
(A1)

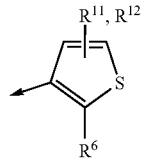
(A2)

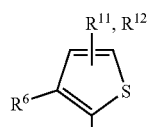
(A3)

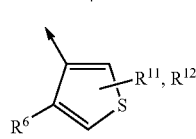
(A4)

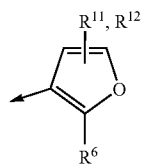
(A5)

-continued

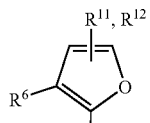
(A6)

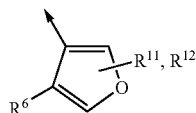
(A7)

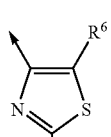
(A8)

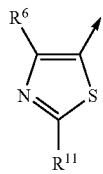
(A9)

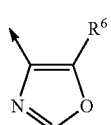
(A10)

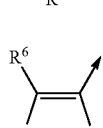
(A11)

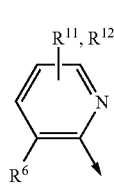
(A12)

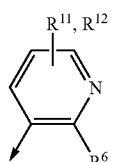
(A13)

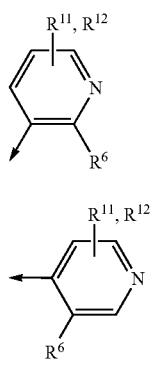
(A14)

-continued

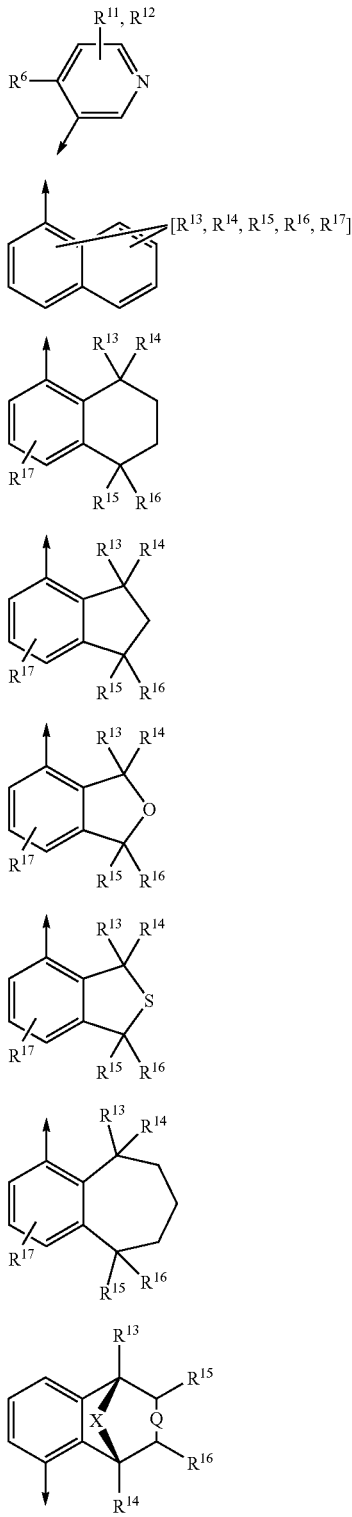

(A15)

(A16)

(A17)

(A18)

(A19)

(A20)

(A21)

(A22)

Q is a single or a double bond; X is O, N($R^{18}$), S or ($CR^{19}R^{20}$)($CR^{21}R^{22}$)$_m$($CR^{23}R^{24}$)$_n$; $R^1$ is halogen, cyano, nitro, $C_{1-4}$ alkyl, $C_{1-4}$ haloalkyl, $C_{1-4}$ alkoxy, $C_{1-4}$ haloalkoxy or optionally substituted $C_{2-4}$ alkenyl, optionally substituted $C_{2-4}$ alkynyl or optionally substituted $SO_2(C_{1-4})$alkyl (where the optionally substituted moieties may each have up to 3 substituents, each independently selected from halogen and $C_{1-4}$ alkoxy); $R^2$ is $C_{1-4}$ alkyl, $C_{1-4}$ haloalkyl, $C_{1-4}$ alkoxy($C_{1-4}$)alkyl or $C_{1-4}$ alkylthio($C_{1-4}$)alkyl or [optionally substituted aryl]($C_{1-4}$)alkyl- or [optionally substituted aryl]oxy($C_{1-4}$)alkyl- (where the optionally substituted aryl moieties may each have up to 3 substituents, each independently selected from halogen and $C_{1-4}$ alkoxy); $R^3$ is hydrogen, $CH_2C\equiv CR^4$, $CH_2CR^4=C(H)R^4$, $CH=C=CH_2$ or $COR^5$ or optionally substituted $C_{1-4}$ alkyl, optionally substituted $C_{1-4}$ alkoxy or optionally substituted $(C_{1-4})$alkylC(=O)O (where the optionally substituted moieties may each have up to 3 substituents, each independently selected from halogen, $C_{1-4}$ alkoxy, $C_{1-4}$ alkyl, $C_{1-2}$ haloalkoxy, hydroxy, cyano, carboxyl, methoxycarbonyl, ethoxycarbonyl, methylsulfonyl and ethylsulfonyl); each $R^4$ is, independently, hydrogen, halogen, $C_{1-4}$ alkyl, $C_{1-4}$ haloalkyl, $C_{1-4}$ alkoxy or $C_{1-4}$ alkoxy($C_{1-4}$)alkyl; $R^5$ is hydrogen or optionally substituted $C_{1-6}$ alkyl, optionally substituted $C_{1-4}$ alkoxy, optionally substituted $C_{1-4}$ alkoxy($C_{1-4}$)alkyl, optionally substituted $C_{1-4}$ alkylthio($C_{1-4}$)alkyl or optionally substituted aryl (where the optionally substituted moieties may each have up to 3 substituents, each independently selected from halogen, $C_{1-6}$ alkoxy, $C_{1-6}$ haloalkoxy, cyano, hydroxy, methoxycarbonyl and ethoxycarbonyl); $R^6$ is phenyl [optionally substituted by up to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), $(Z)_pC\equiv CR^{25}$ and $(Z)_pCR^{28}=CR^{26}R^{27}$], a 5-6 membered heterocyclic ring [in which the ring contains 1 to 3 heteroatoms (each independently chosen from oxygen, sulphur and nitrogen) and the ring is optionally substituted by up to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, C(H)=N—O—($C_{1-6}$ alkyl) and C($C_{1-6}$ alkyl)=N—O—($C_{1-6}$ alkyl)], $C_{3-12}$ alkyl [optionally substituted by up to 6 substituents, each independently selected from halogen, cyano, $C_{1-4}$ alkoxy, $C_{1-4}$ thioalkyl, COO—$C_{1-4}$ alkyl, =N—OH, =N—O—($C_{1-4}$ alkyl), $C_{3-8}$ cycloalkyl (itself optionally substituted by up to 3 substituents, each independently selected from $C_{1-4}$ alkyl, halogen, $C_{1-4}$ alkoxy and $C_{1-4}$ haloalkoxy) and $C_{4-8}$ cycloalkenyl (itself optionally substituted by up to 3 substituents, each independently selected from $C_{1-4}$ alkyl, halogen, $C_{1-4}$ alkoxy and $C_{1-4}$ haloalkoxy)], $C_{2-12}$ alkenyl [optionally substituted by up to 6 substituents, each independently selected from halogen, cyano, $C_{1-4}$ alkoxy, $C_{1-4}$ thioalkyl, COO—($C_{1-4}$ alkyl), =N—OH, =N—O—($C_{1-4}$ alkyl), $C_{3-8}$ cycloalkyl (itself optionally substituted by up to 3 substituents, each independently selected from $C_{1-4}$ alkyl, halogen, $C_{1-4}$ alkoxy and $C_{1-4}$ haloalkoxy) and $C_{4-8}$ cycloalkenyl (itself optionally substituted by up to 3 substituents, each independently selected from $C_{1-4}$ alkyl, halogen, $C_{1-4}$ alkoxy and $C_{1-4}$ haloalkoxy)], $C_{2-12}$ alkynyl [optionally substituted by up to 6 substituents, each independently selected from halogen, cyano, $C_{1-4}$ alkoxy, $C_{1-4}$ thioalkyl, COO—$C_{1-4}$ alkyl, =N—OH, =N—O—($C_{1-4}$ alkyl), $C_{3-8}$ cycloalkyl (itself optionally substituted by up to 3 substituents, each independently selected from $C_{1-4}$ alkyl, halogen, $C_{1-4}$ alkoxy and $C_{1-4}$ haloalkoxy), $Si(CH_3)_3$ and $C_{4-8}$ cycloalkenyl (itself optionally substituted by up to 3 substituents, each independently selected from $C_{1-4}$ alkyl, halogen, $C_{1-4}$ alkoxy and $C_{1-4}$ haloalkoxy)], $C_{3-8}$ cycloalkyl [optionally substituted by up to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl (itself optionally substituted by up to 3 substituents, each independently selected from C$_{1-4}$ alkyl, halogen, C$_{1-4}$ alkoxy and C$_{1-4}$ haloalkoxy) and phenyl (itself optionally substituted by up to five independently selected halogen atoms)], C$_{4-8}$ cycloalkenyl [optionally substituted by up to 3 substituents, each independently selected from halogen, C$_{1-4}$ alkyl, C$_{1-4}$ haloalkyl, C$_{1-4}$ alkoxy, C$_{1-4}$ haloalkoxy, C$_{1-4}$ thioalkyl, C$_{3-6}$ cycloalkyl (itself optionally substituted by up to 3 substituents, each independently selected from C$_{1-4}$ alkyl, halogen, C$_{1-4}$ alkoxy and C$_{1-4}$ haloalkoxy) and phenyl (itself optionally substituted by up to five independently selected halogen atoms)], C$_{6-12}$ bicycloalkyl [optionally substituted by up to 3 substituents, each independently selected from halogen, C$_{1-4}$ alkyl and C$_{1-4}$ haloalkyl] or an aliphatic, saturated or unsaturated group [in which the group contains three to thirteen carbon atoms and at least one silicon atom and, optionally, one to three heteroatoms, each independently selected from oxygen, nitrogen and sulphur, and the group is optionally substituted by up to four independently selected halogen atoms]; R$^7$, R$^8$, R$^9$, R$^{10}$, R$^{11}$ and R$^{12}$ are each, independently, hydrogen, halogen, cyano, nitro, C$_{1-4}$ alkyl, C$_{1-4}$ haloalkyl, C$_{1-4}$ alkoxy, C$_{1-4}$ haloalkoxy, C$_{1-4}$ thioalkyl or C$_{1-4}$ thiohaloalkyl; R$^{13}$, R$^{14}$, R$^{15}$, R$^{16}$ and R$^{17}$ are each, independently, hydrogen, halogen, C$_{1-4}$ alkyl, C(O)CH$_3$, C$_{1-4}$ haloalkyl, C$_{1-4}$ alkoxy, C$_{1-4}$ haloalkoxy, C$_{1-4}$ thioalkyl, C$_{1-4}$ thiohaloalkyl, hydroxymethyl or C$_{1-4}$ alkoxymethyl; R$^{18}$ is hydrogen, C$_{1-4}$ alkyl, C$_{1-4}$ alkoxy(C$_{1-4}$)alkyl, formyl, C(=O)C$_{1-4}$ alkyl (optionally substituted by halogen or C$_{1-4}$-alkoxy) or C(=O)O—C$_{1-6}$ alkyl (optionally substituted by halogen, C$_{1-4}$ alkoxy or CN); R$^{19}$, R$^{20}$, R$^{21}$, R$^{22}$, R$^{23}$ and R$^{24}$ are each, independently, C$_{1-6}$ alkyl, C$_{1-6}$ alkenyl [both optionally substituted by halogen, hydroxy, =O, C$_{1-4}$ alkoxy, O—C(O)—C$_{1-4}$ alkyl, aryl or a 3-7 membered carbocyclic ring (itself optionally substituted by up to three methyl groups)], a 3-7 membered carbocyclic ring (optionally substituted by up to three methyl groups and optionally containing one heteroatom selected from nitrogen and oxygen), hydrogen, halogen, hydroxy or C$_{1-4}$ alkoxy; or R$^{19}$R$^{20}$ together with the carbon atom to which they are attached form a carbonyl-group, a 3-5 membered carbocyclic ring (optionally substituted by up to three methyl groups), C$_{1-6}$ alkylidene (optionally substituted by up to three methyl groups) or C$_{3-6}$ cycloalkylidene (optionally substituted by up to three methyl groups); R$^{25}$ is hydrogen, halogen, C$_{1-4}$ alkyl, C$_{1-4}$ haloalkyl, C$_{1-4}$ alkoxy(C$_{1-4}$)alkyl, C$_{1-4}$ haloalkoxy(C$_{1-4}$)alkyl or Si(C$_{1-4}$ alkyl)$_3$; R$^{26}$ and R$^{27}$ are each, independently, hydrogen, halogen, C$_{1-4}$ alkyl or C$_{1-4}$ haloalkyl; R$^{28}$ is hydrogen, C$_{1-4}$ alkyl or C$_{1-4}$ haloalkyl; m is 0 or 1; n is 0 or 1; p is 0 or 1; and Z is C$_{1-4}$ alkylene.

Halogen is fluoro, chloro, bromo or iodo.

Each alkyl moiety is a straight or branched chain and is, for example, methyl, ethyl, n-propyl, n-butyl, n-pentyl, n-hexyl, iso-propyl, sec-butyl, iso-butyl, tert-butyl, neo-pentyl, n-heptyl, 1,3-dimethylbutyl, 1,3-dimethylpentyl, 1-methyl-3-ethyl-butyl or 1,3,3-trimethylbutyl.

Haloalkyl moieties are alkyl moieties which are substituted by one or more of the same or different halogen atoms and are, for example, CF$_3$, CF$_2$Cl, CHF$_2$, CH$_2$F, CCl$_3$, CF$_3$CH$_2$, CHF$_2$CH$_2$, CH$_2$FCH$_2$, CH$_3$CHF or CH$_3$CF$_2$.

Alkenyl and alkynyl moieties can be in the form of straight or branched chains. The alkenyl moieties, where appropriate, can be of either the (E)- or (Z)-configuration. Examples are vinyl, allyl, ethynyl and propargyl.

Alkylidene moieties can be in the form of straight or branched chains. Alkylidene includes methylidene [CH$_2$=C], ethylidene [CH$_3$C(H)=C], n-propylidene, i-propylidene [(CH$_3$)$_2$C=C], n-butylidene, i-butylidene, 2-butylidene, n-pentylidene, i-pentylidene, neo-pentylidene, 2-pentylidene, n-hexylidene, 2-hexylidene, 3-hexylidene, i-hexylidene and neo-hexylidene.

Cycloalkyl includes cyclopropyl, cyclobutyl, cyclopentyl, cyclohexyl, cycloheptyl and cyclooctyl.

Cycloalkenyl includes cyclobutenyl, cyclopentenyl, cyclohexenyl and cycloheptenyl.

Cycloalkylidene includes cyclopropylidene [c(C$_3$H$_4$)=C], cyclobutylidene, cyclopentylidene and cyclohexylidene.

Bicycloalkyl includes bicyclo[1,1,1]pentyl, bicyclo[2,1,1]hexyl, bicyclo[2,2,1]heptyl, bicyclo[2,2,2]octyl, bicyclo[3,2,1]octyl and bicyclo[3,2,2]nonyl.

Aryl includes phenyl, naphthyl, anthracyl, fluorenyl and indanyl but is preferably phenyl.

In one aspect of the invention, A is as defined above provided that it is not (A1).

In another aspect of the invention, R$^6$ is as defined above provided that it is not an aliphatic, saturated or unsaturated group [in which the group contains three to thirteen carbon atoms and at least one silicon atom and, optionally, one to three heteroatoms, each independently selected from oxygen, nitrogen and sulphur, and the group is optionally substituted by up to four independently selected halogen atoms].

In a further aspect of the invention, A is as defined above provided that it is not (A1) when R$^6$ is an aliphatic, saturated or unsaturated group [in which the group contains three to thirteen carbon atoms and at least one silicon atom and, optionally, one to three heteroatoms, each independently selected from oxygen, nitrogen and sulphur, and the group is optionally substituted by up to four independently selected halogen atoms].

Preferably Q is a single bond.
Preferably n is 0.
Preferably m is 0.
Preferably A is selected from formulae (A1), (A2), (A3), (A16), (A17), (A18), (A19), (A20) and (A22).

More preferably A is selected from formulae (A1); (A2), (A18), (A19) and (A22).

Even more preferably A is selected from one of the following ortho-substituted rings:

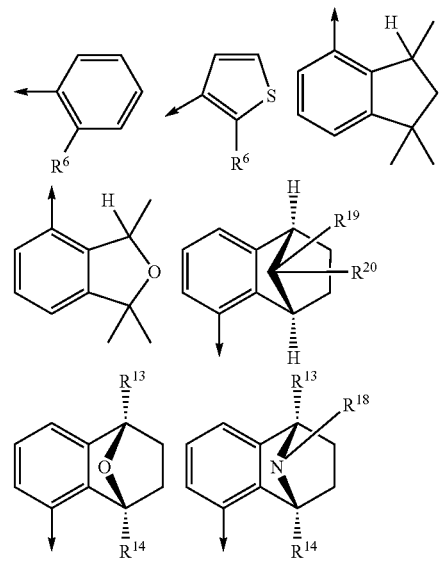

where R$^{13}$ and R$^{14}$ are each, independently, selected from H and C$_{1-4}$ alkyl.

Preferably X is O, $NR^{18}$ or $(CR^{19}R^{20})(CR^{21}R^{22})_m(CR^{23}R^{24})_n$.

More preferably X is O or $(CR^{19}R^{20})(CR^{21}R^{22})_m(CR^{23}R^{24})_n$.

Even more preferably X is $(CR^{19}R^{20})(CR^{21}R^{22})_m(CR^{23}R^{24})_n$.

Most preferably X is $(CR^{19}R^{20})$.

Preferably $R^1$ is $C_{1-4}$ alkyl, $C_{1-4}$ haloalkyl, $NO_2$, CN or $OCF_3$.

More preferably $R^1$ is $CHF_2$, $CF_3$, $CH_2F$, $CF_2Cl$, $CH_3$ or $C_2H_5$.

Even more preferably $R^1$ is $CHF_2$, $CF_3$, $CH_2F$, $CF_2Cl$ or $CH_3$.

Most preferably $R^1$ is $CHF_2$, $CF_3$ or $CH_2F$.

Preferably $R^2$ is $C_{1-4}$ alkyl, $C_{1-4}$ haloalkyl, $C_{1-4}$ alkoxy$(C_{1-4})$alkyl or $C_{1-4}$ alkylthio$(C_{1-4})$alkyl.

More preferably $R^2$ is $CH_3$, $CF_3$, $C_2H_5$, $CH_2OCH_3$ or $CH_2SCH_3$.

Even more preferably $R^2$ is $CH_3$ or $C_2H_5$.

Most preferably $R^2$ is $CH_3$.

Preferably $R^3$ is hydrogen, $CH_2C\equiv CR^4$, $CH_2CR^4=C(H)R^4$, $CH=C=CH_2$ or $COR^5$.

More preferably $R^3$ is H, $CH_2C\equiv CH$, $CH=C=CH_2$, $CH_2CH=CH_2$ or $COCH_3$.

Still more preferably $R^3$ is H, $CH_2C\equiv CH$, $CH=C=CH_2$ or $CH_2CH=CH_2$.

Even more preferably $R^3$ is H, $CH_2C\equiv CH$ or $CH=C=CH_2$.

Most preferably $R^3$ is H.

Preferably each $R^4$ is, independently, H, halogen, $C_{1-4}$ alkyl or $C_{1-4}$ alkoxy.

More preferably each $R^4$ is, independently, H, Cl, Br, $CH_3$ or $CH_3O$.

Still more preferably each $R^4$ is, independently, H, Cl or $CH_3$.

Most preferably each $R^4$ is H.

Preferably $R^5$ is H, $C_{1-6}$ alkyl, $C_{1-4}$ alkoxy or $C_{1-4}$ alkoxy$(C_{1-4})$alkyl.

More preferably $R^5$ is H, methyl, $OC(CH_3)_3$ or $CH_2OCH_3$.

Even more preferably $R^5$ is H or methyl.

Preferably $R^6$ is chosen from $C_{3-10}$ alkyl, $C_{3-9}$ haloalkyl, $C_{3-7}$ cycloalkyl [optionally substituted by $C_3$ cycloalkyl (itself optionally substituted by $C_{1-2}$ alkyl) or by up to two $C_{1-4}$ alkyl groups], an aliphatic group [which contains three to ten carbon atoms and at least one silicon atom and, optionally, one oxygen atom], thienyl [optionally substituted by halo], furyl [optionally substituted by halo], pyridyl [optionally substituted by halo], oxazolyl, isoxazolyl and

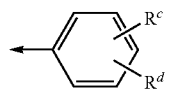

where $R^c$ and $R^d$ are, independently, H, Cl, Br, F, I, CN, $NO_2$, $C_{1-4}$ alkyl, $CF_3$, $SCF_3$, $OCF_3$, CH=NOH, $CH=N-OC_{1-6}$ alkyl, $C\equiv CH$, $C\equiv C-Si(CH_3)_3$, $C(H)=CH_2$ or $C(H)=CH(C_{1-4}$ alkyl).

More preferably $R^6$ is $C_{3-7}$ alkyl, $C_{3-6}$ cycloalkyl [optionally substituted by $C_{1-4}$ alkyl or a $C_3$ cycloalkyl (itself optionally substituted by $C_{1-2}$ alkyl)], an aliphatic group (which contains three to eight carbon atoms and at least one silicon atom) or

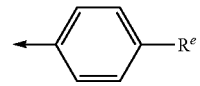

where $R^e$ is Cl, Br, F, $CF_3$, $OCF_3$, $CH=N-OC_{1-4}$ alkyl, $C\equiv CH$, $C\equiv C-Si(CH_3)_3$ or $C(H)=CH_2$ [in one aspect it is preferred that $R^e$ is Cl, Br, F, $CF_3$, $OCF_3$, $CH=N-OC_{1-4}$ alkyl, $C\equiv CH$ or $C(H)=CH_2$].

Even more preferably $R^6$ is chosen from one of the following moieties:

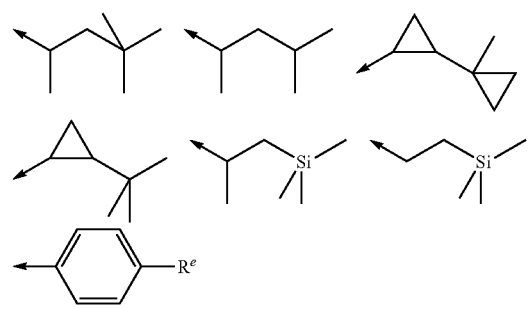

where $R^e$ is Cl, Br, F, $CF_3$, $C\equiv CH$, $C\equiv C-Si(CH_3)_3$ or $CH=N-OC_{1-4}$ alkyl [in one aspect it is preferred that $R^e$ is Cl, Br, F, $CF_3$, $C\equiv CH$ or $CH=N-OC_{1-4}$ alkyl].

Preferably $R^7$ is H, F or $CH_3$.

Preferably $R^8$ is H.

Preferably $R^9$ is H.

Preferably $R^{10}$ is H.

Preferably $R^{11}$ is H.

Preferably $R^{12}$ is H.

Preferably $R^{13}$, $R^{14}$, $R^{15}$, $R^{16}$ are each, independently, H, $CH_3$, $C_2H_5$, $CF_3$, $CH_3O$, $C(O)CH_3$ or $CH_3OCH_2$.

More preferably $R^{13}$, $R^{14}$, $R^{15}$, $R^{16}$ are each, independently, H or $CH_3$.

Preferably $R^{17}$ is H.

Preferably $R^{18}$ is H, $CH_3$, $C_2H_5$, $C(O)OC_{1-4}$ alkyl (optionally substituted with halogen or $C_{1-4}$ alkoxy) or COH.

More preferably $R^{18}$ is $C(O)OC_{1-4}$ alkyl (optionally substituted with halogen or $C_{1-4}$ alkoxy) or COH.

Even more preferably $R^{18}$ is $C(O)OC_{1-4}$ alkyl (optionally substituted with halogen or $C_{1-4}$ alkoxy).

Most preferably $R^{18}$ is $C(O)OC_{1-4}$ alkyl.

Preferably $R^{19}$ and $R^{20}$ are each, independently, H, halogen, $C_{1-5}$ alkyl, $C_{1-3}$ alkoxy, $CH_2O$, $C_{3-6}$ cycloalkyl, $CH_2O-C(=O)CH_3$, $CH_2-C_{3-6}$ cycloalkyl or benzyl; or $R^{19}$ and $R^{20}$ together with the carbon atom to which they are attached form a carbonyl group, a 3-5 membered carbocyclic ring, $C_{1-5}$ alkylidene or $C_{3-6}$ cycloalkylidene.

More preferably $R^{19}$ and $R^{20}$ are, independently, H, $CH_3$, $C_2H_5$, n-$C_3H_7$, i-$C_3H_7$, i-$C_4H_9$, $CH(C_2H_5)_2$, $CH_2$-cyclopropyl or cyclopentyl; or $R^{19}$ and $R^{20}$ together with the carbon atom to which they are attached form a 3-membered carbocyclic ring.

Preferably $R^{21}$ is H or $CH_3$.

Preferably $R^{22}$ is H or $CH_3$.

Preferably $R^{23}$ is H or $CH_3$.

Preferably $R^{24}$ is H or $CH_3$.

Compounds of formula (II):

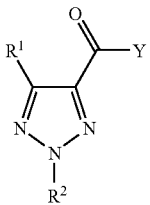

(II)

where $R^1$ and $R^2$ are as defined above for a compound of formula (I) and Y is halogen, hydroxy or $C_{1-5}$ alkoxy, are useful as intermediates in the preparation of compounds of formula (I).

Some compounds of formula (II) are already known in the literature [B. Iddon et al. *J. Chem. Soc. Perkin Trans.* 1, 1341 (1996); M. Begtrup et al., *Acta Chemica Scald.*, 19, 2022 (1965); D. R. Buckle et al., *J. Chem. Res, Syn.* 10, 292 (1982); and A. Peratoner et al., *Sci. Fis. Mat. Nat. Rend* 5, 16 (1907)] but others are novel.

Therefore, in another aspect the present invention provides a compound of formula (II) where $R^1$ and $R^2$ are as defined above for a compound of formula (I) and Y is halogen, hydroxy or $C_{1-5}$ alkoxy; provided that when $R^1$ is chloro and $R^2$ is 4-$CH_3O$—$C_6H_4$—$CH_2$—, Y is not $C_2H_5O$; when $R^1$ is $CH_3O$ and $R^2$ is $CH_3$, Y is not $C_2H_5O$; when $R^1$ is bromo and $R^2$ is $CH_3OCH_2$, Y is not $CH_3O$; and when $R^1$ is $CH_3$ and $R^2$ is $C_2H_5$, Y is not OH.

Preferably Y is hydroxy, chloro, fluoro or $C_{1-3}$ alkoxy.

Some compounds of formula (IIIa) are also novel but some are described in the literature [see, for example, L. A Paquette et al., *J. Amer. Chem Soc.* 99, 3734 (1977); H. Plieninger et al., *Chem. Ber.* 109, 2121 (1976); Kasansski et al., *Zh. Obshch. Khim.* (1959), 29, 2588; and A. J. Kirby et al., *J. Chem. Soc., Perkin Trans.* 2, 1997, 1081].

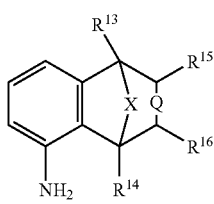

(IIIa)

Anilines of formula (IIIa) are novel when $R^{13}$, $R^{14}$, $R^{15}$, $R^{16}$, Q and X are as defined above for a compound of formula (I); provided that when $R^{13}$, $R^{14}$, $R^{15}$ and $R^{16}$ are each H then X is not $CH_2$ when Q is a double bond and X is not $CH_2CH_2$ when Q is a single bond or a double bond; and when $R^{13}$ is $CH_3$, $R^{14}$ is $OCH_3$ and $R^{15}$ and $R^{16}$ are both H then X is not $CH_2CH_2$ when Q is a single bond.

Therefore, in a further aspect, the present invention provides a compound of formula (IIIa) where $R^{13}$, $R^{14}$, $R^{15}$, $R^{16}$, Q and X are as defined above for a compound of formula (I); provided that when $R^{13}$, $R^{14}$, $R^{15}$ and $R^{16}$ are each H then X is not $CH_2$ when Q is a double bond and X is not $CH_2CH_2$ when Q is a single bond or a double bond; and when $R^{13}$ is $CH_3$, $R^{14}$ is $OCH_3$ and $R^{15}$ and $R^{16}$ are both H then X is not $CH_2CH_2$ when Q is a single bond.

The compounds of formula (I), (II) and (IIIa) may exist as different geometric or optical isomers or in different tautomeric forms. This invention covers, for each formula, all such isomers and tautomers and mixtures thereof in all proportions as well as isotopic forms such as deuterated compounds.

The compounds in Tables 1 to 28 below illustrate compounds of the invention.

Table 1 provides 59 compounds of formula (II) wherein $R^1$, $R^2$ and Y are as defined in Table 1.

TABLE 1

| Compound Number | $R^1$ | $R^2$ | Y |
|---|---|---|---|
| 1.01 | $CHF_2$ | $CH_3$ | OH |
| 1.02 | $CHF_2$ | $CH_3$ | Cl |
| 1.03 | $CHF_2$ | $CH_3$ | $OCH_3$ |
| 1.04 | $CHF_2$ | $CH_3$ | $OC_2H_5$ |
| 1.05 | $CHF_2$ | $CH_3$ | $OC_3H_7(n)$ |
| 1.06 | $CHF_2$ | $CH_3$ | $OC_3H_7(i)$ |
| 1.07 | $CHF_2$ | $C_2H_5$ | OH |
| 1.08 | $CHF_2$ | $C_2H_5$ | Cl |
| 1.09 | $CHF_2$ | $C_2H_5$ | $OCH_3$ |
| 1.10 | $CHF_2$ | $C_2H_5$ | $OC_2H_5$ |
| 1.11 | $CHF_2$ | $C_2H_5$ | $OC_3H_7(n)$ |
| 1.12 | $CHF_2$ | $C_2H_5$ | $OC_3H_7(i)$ |
| 1.13 | $CF_3$ | $CH_3$ | OH |
| 1.14 | $CF_3$ | $CH_3$ | Cl |
| 1.15 | $CF_3$ | $CH_3$ | $OCH_3$ |
| 1.16 | $CF_3$ | $CH_3$ | $OC_2H_5$ |
| 1.17 | $CF_3$ | $CH_3$ | $OC_3H_7(n)$ |
| 1.18 | $CF_3$ | $CH_3$ | $OC_3H_7(i)$ |
| 1.19 | $CF_3$ | $C_2H_5$ | OH |
| 1.20 | $CF_3$ | $C_2H_5$ | Cl |
| 1.21 | $CF_3$ | $C_2H_5$ | $OCH_3$ |
| 1.22 | $CF_3$ | $C_2H_5$ | $OC_2H_5$ |
| 1.23 | $CF_3$ | $C_2H_5$ | $OC_3H_7(n)$ |
| 1.24 | $CF_3$ | $C_2H_5$ | $OC_3H_7(i)$ |
| 1.25 | $CF_3$ | $CH_2OCH_3$ | OH |
| 1.26 | $CF_3$ | $CH_2OCH_3$ | Cl |
| 1.27 | $CF_3$ | $CH_2OCH_3$ | $OCH_3$ |
| 1.28 | $CF_3$ | $CH_2OCH_3$ | $OC_2H_5$ |
| 1.29 | $CF_3$ | $CH_2OCH_3$ | $OC_3H_7(n)$ |
| 1.30 | $CF_3$ | $CH_2OCH_3$ | $OC_3H_7(i)$ |
| 1.31 | $CF_3$ | $CH_3$ | F |
| 1.32 | $CHF_2$ | $CH_3$ | F |
| 1.33 | $CHF_2$ | $CH_2OCH_3$ | OH |
| 1.34 | $CHF_2$ | $CH_2OCH_3$ | $OCH_3$ |
| 1.35 | $CHF_2$ | $CH_2OCH_3$ | $OC_2H_5$ |
| 1.36 | $CF_3$ | $CH_2SCH_3$ | OH |
| 1.37 | $CF_3$ | $CH_2SCH_3$ | $OCH_3$ |
| 1.38 | CN | $CH_3$ | $OCH_3$ |
| 1.39 | $OCF_3$ | $CH_3$ | $OCH_3$ |
| 1.40 | $NO_2$ | $CH_3$ | $OCH_3$ |
| 1.41 | $CH_3$ | $CH_3$ | OH |
| 1.42 | $CH_3$ | $CH_3$ | $OCH_3$ |
| 1.43 | $CH_3$ | $CH_3$ | Cl |
| 1.44 | $CH_3$ | $C_2H_5$ | OH |
| 1.45 | $C_2F_5$ | $CH_3$ | $OCH_3$ |
| 1.46 | $CF_3$ | $CF_3$ | $OCH_3$ |
| 1.47 | $CH_3$ | $CF_3$ | $OCH_3$ |
| 1.48 | $CH_2F$ | $CH_3$ | OH |
| 1.49 | $CH_2F$ | $CH_3$ | Cl |
| 1.50 | $CH_2F$ | $CH_3$ | $OCH_3$ |
| 1.51 | $CH_2F$ | $CH_3$ | $OC_2H_5$ |
| 1.52 | $CH_2F$ | $CH_3$ | $OC_3H_7(n)$ |
| 1.53 | $CH_2F$ | $CH_3$ | $OC_3H_7(i)$ |
| 1.54 | $CH_2F$ | $C_2H_5$ | OH |
| 1.55 | $CH_2F$ | $C_2H_5$ | Cl |
| 1.56 | $CH_2F$ | $C_2H_5$ | $OCH_3$ |
| 1.57 | $CH_2F$ | $C_2H_5$ | $OC_2H_5$ |
| 1.58 | $CH_2F$ | $C_2H_5$ | $OC_3H_7(n)$ |
| 1.59 | $CH_2F$ | $C_2H_5$ | $OC_3H_7(i)$ |

Table X represents Table 2 [when X is 2], Table 3 [when X is 3], Table 4 [when X is 4], Table 5 [when X is 5], Table 6 [when X is 6] and represents Table 7 [when X is 7].

TABLE X

| Cmpd. No. | $R^2$ | $R^3$ | $R^6$ | $R^7$ |
|---|---|---|---|---|
| X.001 | $CH_3$ | H | phenyl | H |
| X.002 | $CH_3$ | $CH_2C{\equiv}CH$ | phenyl | H |
| X.003 | $CH_3$ | H | 2'-fluorophenyl | H |
| X.004 | $CH_3$ | H | 3'-fluorophenyl | H |
| X.005 | $CH_3$ | H | 4'-fluorophenyl | H |
| X.006 | $C_2H_5$ | H | 4'-fluorophenyl | H |
| X.007 | $CH_2OCH_3$ | H | 4'-fluorophenyl | H |
| X.008 | $CH_3$ | $COCH_3$ | 4'-fluorophenyl | H |
| X.009 | $CH_3$ | $COCH_2OCH_3$ | 4'-fluorophenyl | H |
| X.010 | $CH_3$ | $CH_2C{\equiv}CH$ | 4'-fluorophenyl | H |
| X.011 | $CH_3$ | $CH{=}C{=}CH_2$ | 4'-fluorophenyl | H |
| X.012 | $CH_3$ | COO-tert-Bu | 4'-fluorophenyl | H |
| X.013 | $CH_3$ | H | 4'-fluorophenyl | F |
| X.014 | $CH_3$ | H | 4'-fluorophenyl | $CH_3$ |
| X.015 | $CH_3$ | H | 2'-chlorophenyl | H |
| X.016 | $CH_3$ | H | 3'-chlorophenyl | H |
| X.017 | $CH_3$ | H | 4'-chlorophenyl | H |
| X.018 | $C_2H_5$ | H | 4'-chlorophenyl | H |
| X.019 | $CH_2OCH_3$ | H | 4'-chlorophenyl | H |
| X.020 | $CH_3$ | $COCH_3$ | 4'-chlorophenyl | H |
| X.021 | $CH_3$ | $COCH_2OCH_3$ | 4'-chlorophenyl | H |
| X.022 | $CH_3$ | $CH_2C{\equiv}CH$ | 4'-chlorophenyl | H |
| X.023 | $CH_3$ | $CH{=}C{=}CH_2$ | 4'-chlorophenyl | H |
| X.024 | $CH_3$ | COO-tert-Bu | 4'-chlorophenyl | H |
| X.025 | $CH_3$ | H | 4'-chlorophenyl | F |
| X.026 | $CH_3$ | H | 4'-chlorophenyl | $CH_3$ |
| X.027 | $CH_3$ | H | 2'-bromophenyl | H |
| X.028 | $CH_3$ | H | 3'-bromophenyl | H |
| X.029 | $CH_3$ | H | 4'-bromophenyl | H |
| X.030 | $C_2H_5$ | H | 4'-bromophenyl | H |
| X.031 | $CH_2OCH_3$ | H | 4'-bromophenyl | H |
| X.032 | $CH_3$ | $COCH_3$ | 4'-bromophenyl | H |
| X.033 | $CH_3$ | $COCH_2OCH_3$ | 4'-bromophenyl | H |
| X.034 | $CH_3$ | $CH_2C{\equiv}CH$ | 4'-bromophenyl | H |
| X.035 | $CH_3$ | $CH{=}C{=}CH_2$ | 4'-bromophenyl | H |
| X.036 | $CH_3$ | COO-tert-Bu | 4'-bromophenyl | H |
| X.037 | $CH_3$ | H | 4'-bromophenyl | F |
| X.038 | $CH_3$ | H | 4'-bromophenyl | $CH_3$ |
| X.039 | $CH_3$ | H | 2'-iodophenyl | H |
| X.040 | $CH_3$ | H | 3'-iodophenyl | H |
| X.041 | $CH_3$ | H | 4'-iodophenyl | H |
| X.042 | $CH_3$ | H | 2'-$CF_3$-phenyl | H |
| X.043 | $CH_3$ | H | 3'-$CF_3$-phenyl | H |
| X.044 | $CH_3$ | H | 4'-$CF_3$-phenyl | H |
| X.045 | $C_2H_5$ | H | 4'-$CF_3$-phenyl | H |
| X.046 | $CH_2OCH_3$ | H | 4'-$CF_3$-phenyl | H |
| X.047 | $CH_3$ | $COCH_3$ | 4'-$CF_3$-phenyl | H |
| X.048 | $CH_3$ | $COCH_2OCH_3$ | 4'-$CF_3$-phenyl | H |
| X.049 | $CH_3$ | $CH_2C{\equiv}CH$ | 4'-$CF_3$-phenyl | H |
| X.050 | $CH_3$ | COO-tert-Bu | 4'-$CF_3$-phenyl | H |
| X.051 | $CH_3$ | H | 2'-$OCF_3$-phenyl | H |
| X.052 | $CH_3$ | H | 3'-$OCF_3$-phenyl | H |
| X.053 | $CH_3$ | H | 4'-$OCF_3$-phenyl | H |
| X.054 | $C_2H_5$ | H | 4'-$OCF_3$-phenyl | H |
| X.055 | $CH_2OCH_3$ | H | 4'-$OCF_3$-phenyl | H |
| X.056 | $CH_3$ | $COCH_3$ | 4'-$OCF_3$-phenyl | H |
| X.057 | $CH_3$ | $COCH_2OCH_3$ | 4'-$OCF_3$-phenyl | H |
| X.058 | $CH_3$ | $CH_2C{\equiv}CH$ | 4'-$OCF_3$-phenyl | H |
| X.059 | $CH_3$ | COO-tert-Bu | 4'-$OCF_3$-phenyl | H |
| X.060 | $CH_3$ | $CH{=}C{=}CH_2$ | 4'-$OCF_3$-phenyl | H |
| X.061 | $CH_3$ | H | 4'-$SCF_3$-phenyl | H |
| X.062 | $CH_3$ | H | 2'-CH=NOH-phenyl | H |
| X.063 | $CH_3$ | H | 3'-CH=NOH-phenyl | H |
| X.064 | $CH_3$ | H | 4'-CH=NOH-phenyl | H |
| X.065 | $CH_3$ | H | 2'-CH=$NOCH_3$-phenyl | H |
| X.066 | $CH_3$ | H | 3'-CH=$NOCH_3$-phenyl | H |
| X.067 | $CH_3$ | H | 4'-CH=$NOCH_3$-phenyl | H |
| X.068 | $CH_3$ | H | 2'-CH=$NOC_2H_5$-phenyl | H |
| X.069 | $CH_3$ | H | 3'-CH=$NOC_2H_5$-phenyl | H |
| X.070 | $CH_3$ | H | 4'-CH=$NOC_2H_5$-phenyl | H |
| X.071 | $CH_3$ | H | 2'-CN-phenyl | H |
| X.072 | $CH_3$ | H | 3'-CN-phenyl | H |
| X.073 | $CH_3$ | H | 4'-CN-phenyl | H |
| X.074 | $CH_3$ | H | 2'-$NO_2$-phenyl | H |
| X.075 | $CH_3$ | H | 3'-$NO_2$-phenyl | H |
| X.076 | $CH_3$ | H | 4'-$NO_2$-phenyl | H |
| X.077 | $CH_3$ | H | 3',4'-difluorophenyl | H |

TABLE X-continued

| Cmpd. No. | $R^2$ | $R^3$ | $R^6$ | $R^7$ |
|---|---|---|---|---|
| X.078 | $C_2H_5$ | H | 3',4'-difluorophenyl | H |
| X.079 | $CH_2OCH_3$ | H | 3',4'-difluorophenyl | H |
| X.080 | $CH_3$ | $COCH_3$ | 3',4'-difluorophenyl | H |
| X.081 | $CH_3$ | $COCH_2OCH_3$ | 3',4'-difluorophenyl | H |
| X.082 | $CH_3$ | $CH_2C{\equiv}CH$ | 3',4'-difluorophenyl | H |
| X.083 | $CH_3$ | COO-tert-Bu | 3',4'-difluorophenyl | H |
| X.084 | $CH_3$ | $CH{=}C{=}CH_2$ | 3',4'-difluorophenyl | H |
| X.085 | $CH_3$ | H | 3',4'-difluorophenyl | F |
| X.086 | $CH_3$ | H | 3',4'-difluorophenyl | $CH_3$ |
| X.087 | $CH_3$ | H | 3',4'-dichlorophenyl | H |
| X.088 | $C_2H_5$ | H | 3',4'-dichlorophenyl | H |
| X.089 | $CH_2OCH_3$ | H | 3',4'-dichlorophenyl | H |
| X.090 | $CH_3$ | $COCH_3$ | 3',4'-dichlorophenyl | H |
| X.091 | $CH_3$ | $COCH_2OCH_3$ | 3',4'-dichlorophenyl | H |
| X.092 | $CH_3$ | $CH_2C{\equiv}CH$ | 3',4'-dichlorophenyl | H |
| X.093 | $CH_3$ | COO-tert-Bu | 3',4'-dichlorophenyl | H |
| X.094 | $CH_3$ | $CH{=}C{=}CH_2$ | 3',4'-dichlorophenyl | H |
| X.095 | $CH_3$ | H | 3',4'-dichlorophenyl | F |
| X.096 | $CH_3$ | H | 3',4'-dichlorophenyl | $CH_3$ |
| X.097 | $CH_3$ | H | 4'-chloro-3'-fluoro-phenyl | H |
| X.098 | $C_2H_5$ | H | 4'-chloro-3'-fluoro-phenyl | H |
| X.099 | $CH_2OCH_3$ | H | 4'-chloro-3'-fluoro-phenyl | H |
| X.100 | $CH_3$ | $COCH_3$ | 4'-chloro-3'-fluoro-phenyl | H |
| X.101 | $CH_3$ | $COCH_2OCH_3$ | 4'-chloro-3'-fluoro-phenyl | H |
| X.102 | $CH_3$ | $CH_2C{\equiv}CH$ | 4'-chloro-3'-fluoro-phenyl | H |
| X.103 | $CH_3$ | COO-tert-Bu | 4'-chloro-3'-fluoro-phenyl | H |
| X.104 | $CH_3$ | $CH{=}C{=}CH_2$ | 4'-chloro-3'-fluoro-phenyl | H |
| X.105 | $CH_3$ | H | 4'-chloro-3'-fluoro-phenyl | F |
| X.106 | $CH_3$ | H | 4'-chloro-3'-fluoro-phenyl | $CH_3$ |
| X.107 | $CH_3$ | H | 3'-chloro-4'-fluoro-phenyl | H |
| X.108 | $C_2H_5$ | H | 3'-chloro-4'-fluoro-phenyl | H |
| X.109 | $CH_2OCH_3$ | H | 3'-chloro-4'-fluoro-phenyl | H |
| X.110 | $CH_3$ | $COCH_3$ | 3'-chloro-4'-fluoro-phenyl | H |
| X.111 | $CH_3$ | $COCH_2OCH_3$ | 3'-chloro-4'-fluoro-phenyl | H |
| X.112 | $CH_3$ | $CH_2C{\equiv}CH$ | 3'-chloro-4'-fluoro-phenyl | H |
| X.113 | $CH_3$ | COO-tert-Bu | 3'-chloro-4'-fluoro-phenyl | H |
| X.114 | $CH_3$ | $CH{=}C{=}CH_2$ | 3'-chloro-4'-fluoro-phenyl | H |
| X.115 | $CH_3$ | H | 3'-chloro-4'-fluoro-phenyl | F |
| X.116 | $CH_3$ | H | 3'-chloro-4'-fluoro-phenyl | $CH_3$ |
| X.117 | $CH_3$ | H | 2'-4'-dichloro-phenyl | H |
| X.118 | $CH_2OCH_3$ | H | 2'-4'-dichloro-phenyl | H |
| X.119 | $CH_3$ | H | 2'-4'-difluoro-phenyl | H |
| X.120 | $CH_2OCH_3$ | H | 2'-4'-difluoro-phenyl | H |
| X.121 | $CH_3$ | H | $CH_2CH_2CH_3$ | H |
| X.122 | $C_2H_5$ | H | $CH_2CH_2CH_3$ | H |
| X.123 | $CH_2OCH_3$ | H | $CH_2CH_2CH_3$ | H |
| X.124 | $CH_3$ | $CH_2C{\equiv}CH$ | $CH_2CH_2CH_3$ | H |
| X.125 | $CH_3$ | H | $CH_2CH_2CH_2CH_3$ | H |
| X.126 | $C_2H_5$ | H | $CH_2CH_2CH_2CH_3$ | H |
| X.127 | $CH_2OCH_3$ | H | $CH_2CH_2CH_2CH_3$ | H |
| X.128 | $CH_3$ | $CH_2C{\equiv}CH$ | $CH_2CH_2CH_2CH_3$ | H |
| X.129 | $CH_3$ | H | $CH_2CH_2CH_2CH_3$ | F |
| X.130 | $CH_3$ | H | $CH_2CH_2CH_2CH_3$ | $CH_3$ |
| X.131 | $CH_3$ | H | $CH_2CH_2CH_2(C_2H_5)$ | H |
| X.132 | $C_2H_5$ | H | $CH_2CH_2CH_2(C_2H_5)$ | H |
| X.133 | $CH_2OCH_3$ | H | $CH_2CH_2CH_2(C_2H_5)$ | H |
| X.134 | $CH_3$ | $CH_2C{\equiv}CH$ | $CH_2CH_2CH_2(C_2H_5)$ | H |
| X.135 | $CH_3$ | H | $CH_2CH_2CH_2(C_2H_5)$ | F |
| X.136 | $CH_3$ | H | $CH_2CH_2CH_2(C_2H_5)$ | $CH_3$ |
| X.137 | $CH_3$ | H | $CH_2CH_2CH(CH_3)_2$ | H |
| X.138 | $C_2H_5$ | H | $CH_2CH_2CH(CH_3)_2$ | H |
| X.139 | $CH_2OCH_3$ | H | $CH_2CH_2CH(CH_3)_2$ | H |
| X.140 | $CH_3$ | $COCH_3$ | $CH_2CH_2CH(CH_3)_2$ | H |
| X.141 | $CH_3$ | $COCH_2OCH_3$ | $CH_2CH_2CH(CH_3)_2$ | H |
| X.142 | $CH_3$ | $CH_2C{\equiv}CH$ | $CH_2CH_2CH(CH_3)_2$ | H |
| X.143 | $CH_3$ | COO-tert-Bu | $CH_2CH_2CH(CH_3)_2$ | H |
| X.144 | $CH_3$ | $CH{=}C{=}CH_2$ | $CH_2CH_2CH(CH_3)_2$ | H |
| X.145 | $CH_3$ | H | $CH_2CH_2CH(CH_3)_2$ | F |
| X.146 | $CH_3$ | H | $CH_2CH_2CH(CH_3)_2$ | $CH_3$ |
| X.147 | $CH_3$ | H | $CH_2CH_2CH(CH_3)(C_2H_5)$ | H |
| X.148 | $C_2H_5$ | H | $CH_2CH_2CH(CH_3)(C_2H_5)$ | H |
| X.149 | $CH_2OCH_3$ | H | $CH_2CH_2CH(CH_3)(C_2H_5)$ | H |
| X.150 | $CH_3$ | $COCH_3$ | $CH_2CH_2CH(CH_3)(C_2H_5)$ | H |
| X.151 | $CH_3$ | $COCH_2OCH_3$ | $CH_2CH_2CH(CH_3)(C_2H_5)$ | H |
| X.152 | $CH_3$ | $CH_2C{\equiv}CH$ | $CH_2CH_2CH(CH_3)(C_2H_5)$ | H |
| X.153 | $CH_3$ | COO-tert-Bu | $CH_2CH_2CH(CH_3)(C_2H_5)$ | H |
| X.154 | $CH_3$ | $CH{=}C{=}CH_2$ | $CH_2CH_2CH(CH_3)(C_2H_5)$ | H |

TABLE X-continued

| Cmpd. No. | R² | R³ | R⁶ | R⁷ |
|---|---|---|---|---|
| X.155 | CH₃ | H | CH₂CH₂CH(CH₃)(C₂H₅) | F |
| X.156 | CH₃ | H | CH₂CH₂CH(CH₃)(C₂H₅) | CH₃ |
| X.157 | CH₃ | H | CH₂CH₂CH(C₂H₅)₂ | H |
| X.158 | C₂H₅ | H | CH₂CH₂CH(C₂H₅)₂ | H |
| X.159 | CH₂OCH₃ | H | CH₂CH₂CH(C₂H₅)₂ | H |
| X.160 | CH₃ | COCH₃ | CH₂CH₂CH(C₂H₅)₂ | H |
| X.161 | CH₃ | COCH₂OCH₃ | CH₂CH₂CH(C₂H₅)₂ | H |
| X.162 | CH₃ | CH₂C≡CH | CH₂CH₂CH(C₂H₅)₂ | H |
| X.163 | CH₃ | COO-tert-Bu | CH₂CH₂CH(C₂H₅)₂ | H |
| X.164 | CH₃ | CH=C=CH₂ | CH₂CH₂CH(C₂H₅)₂ | H |
| X.165 | CH₃ | H | CH₂CH₂CH(C₂H₅)₂ | F |
| X.166 | CH₃ | H | CH₂CH₂CH(C₂H₅)₂ | CH₃ |
| X.167 | CH₃ | H | CH₂CH₂C(CH₃)₃ | H |
| X.168 | C₂H₅ | H | CH₂CH₂C(CH₃)₃ | H |
| X.169 | CH₂OCH₃ | H | CH₂CH₂C(CH₃)₃ | H |
| X.170 | CH₃ | COCH₃ | CH₂CH₂C(CH₃)₃ | H |
| X.171 | CH₃ | COCH₂OCH₃ | CH₂CH₂C(CH₃)₃ | H |
| X.172 | CH₃ | CH₂C≡CH | CH₂CH₂C(CH₃)₃ | H |
| X.173 | CH₃ | COO-tert-Bu | CH₂CH₂C(CH₃)₃ | H |
| X.174 | CH₃ | CH=C=CH₂ | CH₂CH₂C(CH₃)₃ | H |
| X.175 | CH₃ | H | CH₂CH₂C(CH₃)₃ | F |
| X.176 | CH₃ | H | CH₂CH₂C(CH₃)₃ | CH₃ |
| X.177 | CH₃ | H | CH₂CH₂C(CH₃)₂(C₂H₅) | H |
| X.178 | C₂H₅ | H | CH₂CH₂C(CH₃)₂(C₂H₅) | H |
| X.179 | CH₂OCH₃ | H | CH₂CH₂C(CH₃)₂(C₂H₅) | H |
| X.180 | CH₃ | COCH₃ | CH₂CH₂C(CH₃)₂(C₂H₅) | H |
| X.181 | CH₃ | COCH₂OCH₃ | CH₂CH₂C(CH₃)₂(C₂H₅) | H |
| X.182 | CH₃ | CH₂C≡CH | CH₂CH₂C(CH₃)₂(C₂H₅) | H |
| X.183 | CH₃ | COO-tert-Bu | CH₂CH₂C(CH₃)₂(C₂H₅) | H |
| X.184 | CH₃ | CH=C=CH₂ | CH₂CH₂C(CH₃)₂(C₂H₅) | H |
| X.185 | CH₃ | H | CH₂CH₂C(CH₃)₂(C₂H₅) | F |
| X.186 | CH₃ | H | CH₂CH₂C(CH₃)₂(C₂H₅) | CH₃ |
| X.187 | CH₃ | H | CH₂CH₂C(CH₃)(C₂H₅)₂ | H |
| X.188 | C₂H₅ | H | CH₂CH₂C(CH₃)(C₂H₅)₂ | H |
| X.189 | CH₂OCH₃ | H | CH₂CH₂C(CH₃)(C₂H₅)₂ | H |
| X.190 | CH₃ | COCH₃ | CH₂CH₂C(CH₃)(C₂H₅)₂ | H |
| X.191 | CH₃ | COCH₂OCH₃ | CH₂CH₂C(CH₃)(C₂H₅)₂ | H |
| X.192 | CH₃ | CH₂C≡CH | CH₂CH₂C(CH₃)(C₂H₅)₂ | H |
| X.193 | CH₃ | COO-tert-Bu | CH₂CH₂C(CH₃)(C₂H₅)₂ | H |
| X.194 | CH₃ | CH=C=CH₂ | CH₂CH₂C(CH₃)(C₂H₅)₂ | H |
| X.195 | CH₃ | H | CH₂CH₂C(CH₃)(C₂H₅)₂ | F |
| X.196 | CH₃ | H | CH₂CH₂C(CH₃)(C₂H₅)₂ | CH₃ |
| X.197 | CH₃ | H | CH(CH₃)CH₂CH₃ | H |
| X.198 | C₂H₅ | H | CH(CH₃)CH₂CH₃ | H |
| X.199 | CH₂OCH₃ | H | CH(CH₃)CH₂CH₃ | H |
| X.200 | CH₃ | CH₂C≡CH | CH(CH₃)CH₂CH₃ | H |
| X.201 | CH₃ | H | CH(C₂H₅)CH₂CH₃ | H |
| X.202 | C₂H₅ | H | CH(C₂H₅)CH₂CH₃ | H |
| X.203 | CH₂OCH₃ | H | CH(C₂H₅)CH₂CH₃ | H |
| X.204 | CH₃ | CH₂C≡CH | CH(C₂H₅)CH₂CH₃ | H |
| X.205 | CH₃ | H | CH(CF₃)CH₂CH₃ | H |
| X.206 | C₂H₅ | H | CH(CF₃)CH₂CH₃ | H |
| X.207 | CH₂OCH₃ | H | CH(CF₃)CH₂CH₃ | H |
| X.208 | CH₃ | CH₂C≡CH | CH(CF₃)CH₂CH₃ | H |
| X.209 | CH₃ | H | CH(CH₃)CH₂CH₂CH₃ | H |
| X.210 | C₂H₅ | H | CH(CH₃)CH₂CH₂CH₃ | H |
| X.211 | CH₂OCH₃ | H | CH(CH₃)CH₂CH₂CH₃ | H |
| X.212 | CH₃ | CH₂C≡CH | CH(CH₃)CH₂CH₂CH₃ | H |
| X.213 | CH₃ | H | CH(C₂H₅)CH₂CH₂CH₃ | H |
| X.214 | C₂H₅ | H | CH(C₂H₅)CH₂CH₂CH₃ | H |
| X.215 | CH₂OCH₃ | H | CH(C₂H₅)CH₂CH₂CH₃ | H |
| X.216 | CH₃ | CH₂C≡CH | CH(C₂H₅)CH₂CH₂CH₃ | H |
| X.217 | CH₃ | H | CH(CF₃)CH₂CH₂CH₃ | H |
| X.218 | C₂H₅ | H | CH(CF₃)CH₂CH₂CH₃ | H |
| X.219 | CH₃ | H | CH(CH₃)CH₂CH(CH₃)₂ | H |
| X.220 | C₂H₅ | H | CH(CH₃)CH₂CH(CH₃)₂ | H |
| X.221 | CH₂OCH₃ | H | CH(CH₃)CH₂CH(CH₃)₂ | H |
| X.222 | CH₃ | COCH₃ | CH(CH₃)CH₂CH(CH₃)₂ | H |
| X.223 | CH₃ | COCH₂OCH₃ | CH(CH₃)CH₂CH(CH₃)₂ | H |
| X.224 | CH₃ | CH₂C≡CH | CH(CH₃)CH₂CH(CH₃)₂ | H |
| X.225 | CH₃ | COO-tert-Bu | CH(CH₃)CH₂CH(CH₃)₂ | H |
| X.226 | CH₃ | CH=C=CH₂ | CH(CH₃)CH₂CH(CH₃)₂ | H |
| X.227 | CH₃ | H | CH(CH₃)CH₂CH(CH₃)₂ | F |
| X.228 | CH₃ | H | CH(CH₃)CH₂CH(CH₃)₂ | CH₃ |
| X.229 | CH₃ | H | CH(CH₃)CH₂CH(CH₃)(C₂H₅) | H |
| X.230 | C₂H₅ | H | CH(CH₃)CH₂CH(CH₃)(C₂H₅) | H |
| X.231 | CH₂OCH₃ | H | CH(CH₃)CH₂CH(CH₃)(C₂H₅) | H |

TABLE X-continued

| Cmpd. No. | R² | R³ | R⁶ | R⁷ |
|---|---|---|---|---|
| X.232 | CH₃ | COCH₃ | CH(CH₃)CH₂CH(CH₃)(C₂H₅) | H |
| X.233 | CH₃ | COCH₂OCH₃ | CH(CH₃)CH₂CH(CH₃)(C₂H₅) | H |
| X.234 | CH₃ | CH₂C≡CH | CH(CH₃)CH₂CH(CH₃)(C₂H₅) | H |
| X.235 | CH₃ | COO-tert-Bu | CH(CH₃)CH₂CH(CH₃)(C₂H₅) | H |
| X.236 | CH₃ | CH=C=CH₂ | CH(CH₃)CH₂CH(CH₃)(C₂H₅) | H |
| X.237 | CH₃ | H | CH(CH₃)CH₂CH(CH₃)(C₂H₅) | F |
| X.238 | CH₃ | H | CH(CH₃)CH₂CH(CH₃)(C₂H₅) | CH₃ |
| X.239 | CH₃ | H | CH(CH₃)CH₂CH(C₂H₅)₂ | H |
| X.240 | C₂H₅ | H | CH(CH₃)CH₂CH(C₂H₅)₂ | H |
| X.241 | CH₂OCH₃ | H | CH(CH₃)CH₂CH(C₂H₅)₂ | H |
| X.242 | CH₃ | COCH₃ | CH(CH₃)CH₂CH(C₂H₅)₂ | H |
| X.243 | CH₃ | COCH₂OCH₃ | CH(CH₃)CH₂CH(C₂H₅)₂ | H |
| X.244 | CH₃ | CH₂C≡CH | CH(CH₃)CH₂CH(C₂H₅)₂ | H |
| X.245 | CH₃ | COO-tert-Bu | CH(CH₃)CH₂CH(C₂H₅)₂ | H |
| X.246 | CH₃ | CH=C=CH₂ | CH(CH₃)CH₂CH(C₂H₅)₂ | H |
| X.247 | CH₃ | H | CH(CH₃)CH₂CH(C₂H₅)₂ | F |
| X.248 | CH₃ | H | CH(CH₃)CH₂CH(C₂H₅)₂ | CH₃ |
| X.249 | CH₃ | H | CH(C₂H₅)CH₂CH(CH₃)₂ | H |
| X.250 | C₂H₅ | H | CH(C₂H₅)CH₂CH(CH₃)₂ | H |
| X.251 | CH₂OCH₃ | H | CH(C₂H₅)CH₂CH(CH₃)₂ | H |
| X.252 | CH₃ | COCH₃ | CH(C₂H₅)CH₂CH(CH₃)₂ | H |
| X.253 | CH₃ | COCH₂OCH₃ | CH(C₂H₅)CH₂CH(CH₃)₂ | H |
| X.254 | CH₃ | CH₂C≡CH | CH(C₂H₅)CH₂CH(CH₃)₂ | H |
| X.255 | CH₃ | COO-tert-Bu | CH(C₂H₅)CH₂CH(CH₃)₂ | H |
| X.256 | CH₃ | CH=C=CH₂ | CH(C₂H₅)CH₂CH(CH₃)₂ | H |
| X.257 | CH₃ | H | CH(C₂H₅)CH₂CH(CH₃)₂ | F |
| X.258 | CH₃ | H | CH(C₂H₅)CH₂CH(CH₃)₂ | CH₃ |
| X.259 | CH₃ | H | CH(C₂H₅)CH₂CH(CH₃)(C₂H₅) | H |
| X.260 | C₂H₅ | H | CH(C₂H₅)CH₂CH(CH₃)(C₂H₅) | H |
| X.261 | CH₂OCH₃ | H | CH(C₂H₅)CH₂CH(CH₃)(C₂H₅) | H |
| X.262 | CH₃ | CH₂C≡CH | CH(C₂H₅)CH₂CH(CH₃)(C₂H₅) | H |
| X.263 | CH₃ | H | CH(C₂H₅)CH₂CH(C₂H₅)₂ | H |
| X.264 | C₂H₅ | H | CH(C₂H₅)CH₂CH(C₂H₅)₂ | H |
| X.265 | CH₂OCH₃ | H | CH(C₂H₅)CH₂CH(C₂H₅)₂ | H |
| X.266 | CH₃ | CH₂C≡CH | CH(C₂H₅)CH₂CH(C₂H₅)₂ | H |
| X.267 | CH₃ | H | CH(CF₃)CH₂CH(CH₃)₂ | H |
| X.268 | C₂H₅ | H | CH(CF₃)CH₂CH(CH₃)₂ | H |
| X.269 | CH₂OCH₃ | H | CH(CF₃)CH₂CH(CH₃)₂ | H |
| X.270 | CH₃ | CH₂C≡CH | CH(CF₃)CH₂CH(CH₃)₂ | H |
| X.271 | CH₃ | H | CH(CF₃)CH₂CH(CH₃)(C₂H₅) | H |
| X.272 | CH₃ | H | CH(CF₃)CH₂CH(C₂H₅)₂ | H |
| X.273 | CH₃ | H | CH(CH₃)CH₂C(CH₃)₃ | H |
| X.274 | C₂H₅ | H | CH(CH₃)CH₂C(CH₃)₃ | H |
| X.275 | CH₂OCH₃ | H | CH(CH₃)CH₂C(CH₃)₃ | H |
| X.276 | CH₃ | COCH₃ | CH(CH₃)CH₂C(CH₃)₃ | H |
| X.277 | CH₃ | COCH₂OCH₃ | CH(CH₃)CH₂C(CH₃)₃ | H |
| X.278 | CH₃ | CH₂C≡CH | CH(CH₃)CH₂C(CH₃)₃ | H |
| X.279 | CH₃ | COO-tert-Bu | CH(CH₃)CH₂C(CH₃)₃ | H |
| X.280 | CH₃ | CH=C=CH₂ | CH(CH₃)CH₂C(CH₃)₃ | H |
| X.281 | CH₃ | H | CH(CH₃)CH₂C(CH₃)₃ | F |
| X.282 | CH₃ | H | CH(CH₃)CH₂C(CH₃)₃ | CH₃ |
| X.283 | CH₃ | H | CH(CH₃)CH₂C(CH₃)₂(C₂H₅) | H |
| X.284 | C₂H₅ | H | CH(CH₃)CH₂C(CH₃)₂(C₂H₅) | H |
| X.285 | CH₂OCH₃ | H | CH(CH₃)CH₂C(CH₃)₂(C₂H₅) | H |
| X.286 | CH₃ | COCH₃ | CH(CH₃)CH₂C(CH₃)₂(C₂H₅) | H |
| X.287 | CH₃ | COCH₂OCH₃ | CH(CH₃)CH₂C(CH₃)₂(C₂H₅) | H |
| X.288 | CH₃ | CH₂C≡CH | CH(CH₃)CH₂C(CH₃)₂(C₂H₅) | H |
| X.289 | CH₃ | COO-tert-Bu | CH(CH₃)CH₂C(CH₃)₂(C₂H₅) | H |
| X.290 | CH₃ | CH=C=CH₂ | CH(CH₃)CH₂C(CH₃)₂(C₂H₅) | H |
| X.291 | CH₃ | H | CH(CH₃)CH₂C(CH₃)₂(C₂H₅) | F |
| X.292 | CH₃ | H | CH(CH₃)CH₂C(CH₃)₂(C₂H₅) | CH₃ |
| X.293 | CH₃ | H | CH(CH₃)CH₂C(CH₃)(C₂H₅)₂ | H |
| X.294 | C₂H₅ | H | CH(CH₃)CH₂C(CH₃)(C₂H₅)₂ | H |
| X.295 | CH₂OCH₃ | H | CH(CH₃)CH₂C(CH₃)(C₂H₅)₂ | H |
| X.296 | CH₃ | CH₂C≡CH | CH(CH₃)CH₂C(CH₃)(C₂H₅)₂ | H |
| X.297 | CH₃ | H | CH(C₂H₅)CH₂C(CH₃)₃ | H |
| X.298 | C₂H₅ | H | CH(C₂H₅)CH₂C(CH₃)₃ | H |
| X.299 | CH₂OCH₃ | H | CH(C₂H₅)CH₂C(CH₃)₃ | H |
| X.300 | CH₃ | CH₂C≡CH | CH(C₂H₅)CH₂C(CH₃)₃ | H |
| X.301 | CH₃ | H | CH(C₂H₅)CH₂C(CH₃)₂(C₂H₅) | H |
| X.302 | C₂H₅ | H | CH(C₂H₅)CH₂C(CH₃)₂(C₂H₅) | H |
| X.303 | CH₂OCH₃ | H | CH(C₂H₅)CH₂C(CH₃)₂(C₂H₅) | H |
| X.304 | CH₃ | CH₂C≡CH | CH(C₂H₅)CH₂C(CH₃)₂(C₂H₅) | H |
| X.305 | CH₃ | H | CH(C₂H₅)CH₂C(CH₃)(C₂H₅)₂ | H |
| X.306 | C₂H₅ | H | CH(C₂H₅)CH₂C(CH₃)(C₂H₅)₂ | H |
| X.307 | CH₂OCH₃ | H | CH(C₂H₅)CH₂C(CH₃)(C₂H₅)₂ | H |
| X.308 | CH₃ | CH₂C≡CH | CH(C₂H₅)CH₂C(CH₃)(C₂H₅)₂ | H |

TABLE X-continued

| Cmpd. No. | R² | R³ | R⁶ | R⁷ |
|---|---|---|---|---|
| X.309 | CH₃ | H | CH(CF₃)CH₂C(CH₃)₃ | H |
| X.310 | C₂H₅ | H | CH(CF₃)CH₂C(CH₃)₃ | H |
| X.311 | CH₂OCH₃ | H | CH(CF₃)CH₂C(CH₃)₃ | H |
| X.312 | CH₃ | CH₂C≡CH | CH(CF₃)CH₂C(CH₃)₃ | H |
| X.313 | CH₃ | H | CH(CF₃)CH₂C(CH₃)₂(C₂H₅) | H |
| X.314 | C₂H₅ | H | CH(CF₃)CH₂C(CH₃)₂(C₂H₅) | H |
| X.315 | CH₂OCH₃ | H | CH(CF₃)CH₂C(CH₃)₂(C₂H₅) | H |
| X.316 | CH₃ | CH₂C≡CH | CH(CF₃)CH₂C(CH₃)₂(C₂H₅) | H |
| X.317 | CH₃ | H | CH(CF₃)CH₂C(CH₃)(C₂H₅)₂ | H |
| X.318 | C₂H₅ | H | CH(CF₃)CH₂C(CH₃)(C₂H₅)₂ | H |
| X.319 | CH₂OCH₃ | H | CH(CF₃)CH₂C(CH₃)(C₂H₅)₂ | H |
| X.320 | CH₃ | CH₂C≡CH | CH(CF₃)CH₂C(CH₃)(C₂H₅)₂ | H |
| X.321 | CH₃ | H | 2'-tert-butyl-cyclopropyl | H |
| X.322 | C₂H₅ | H | 2'-tert-butyl-cyclopropyl | H |
| X.323 | CH₂OCH₃ | H | 2'-tert-butyl-cyclopropyl | H |
| X.324 | CH₃ | CH₂C≡CH | 2'-tert-butyl-cyclopropyl | H |
| X.325 | CH₃ | H | 2'-isobutyl-cyclopropyl | H |
| X.326 | C₂H₅ | H | 2'-isobutyl-cyclopropyl | H |
| X.327 | CH₂OCH₃ | H | 2'-isobutyl-cyclopropyl | H |
| X.328 | CH₃ | CH₂C≡CH | 2'-isobutyl-cyclopropyl | H |
| X.329 | CH₃ | H | 4',4'-dimethyl-cyclobutyl | H |
| X.330 | C₂H₅ | H | 4',4'-dimethyl-cyclobutyl | H |
| X.331 | CH₂OCH₃ | H | 4',4'-dimethyl-cyclobutyl | H |
| X.332 | CH₃ | CH₂C≡CH | 4',4'-dimethyl-cyclobutyl | H |
| X.333 | CH₃ | H | cyclopentyl | H |
| X.334 | C₂H₅ | H | cyclopentyl | H |
| X.335 | CH₂OCH₃ | H | cyclopentyl | H |
| X.336 | CH₃ | CH₂C≡CH | cyclopentyl | H |
| X.337 | CH₃ | H | 3'-methyl-cyclopentyl | H |
| X.338 | C₂H₅ | H | 3'-methyl-cyclopentyl | H |
| X.339 | CH₂OCH₃ | H | 3'-methyl-cyclopentyl | H |
| X.340 | CH₃ | CH₂C≡CH | 3'-methyl-cyclopentyl | H |
| X.341 | CH₃ | H | cyclohexyl | H |
| X.342 | C₂H₅ | H | cyclohexyl | H |
| X.343 | CH₂OCH₃ | H | cyclohexyl | H |
| X.344 | CH₃ | CH₂C≡CH | cyclohexyl | H |
| X.345 | CH₃ | H | 3'-methyl-cyclohexyl | H |
| X.346 | C₂H₅ | H | 3'-methyl-cyclohexyl | H |
| X.347 | CH₂OCH₃ | H | 3'-methyl-cyclohexyl | H |
| X.348 | CH₃ | CH₂C≡CH | 3'-methyl-cyclohexyl | H |
| X.349 | CH₃ | H | 4'-methyl-cyclohexyl | H |
| X.350 | C₂H₅ | H | 4'-methyl-cyclohexyl | H |
| X.351 | CH₂OCH₃ | H | 4'-methyl-cyclohexyl | H |
| X.352 | CH₃ | CH₂C≡CH | 4'-methyl-cyclohexyl | H |
| X.353 | CH₃ | H | cycloheptyl | H |
| X.354 | C₂H₅ | H | cycloheptyl | H |
| X.355 | CH₂OCH₃ | H | cycloheptyl | H |
| X.356 | CH₃ | CH₂C≡CH | cycloheptyl | H |
| X.357 | CH₃ | H | 2'-thienyl | H |
| X.358 | C₂H₅ | H | 2'-thienyl | H |
| X.359 | CH₂OCH₃ | H | 2'-thienyl | H |
| X.360 | CH₃ | CH₂C≡CH | 2'-thienyl | H |
| X.361 | CH₃ | H | 3'-thienyl | H |
| X.362 | C₂H₅ | H | 3'-thienyl | H |
| X.363 | CH₂OCH₃ | H | 3'-thienyl | H |
| X.364 | CH₃ | CH₂C≡CH | 3'-thienyl | H |
| X.365 | CH₃ | H | 5'-chloro-2'-thienyl | H |
| X.366 | C₂H₅ | H | 5'-chloro-2'-thienyl | H |
| X.367 | CH₂OCH₃ | H | 5'-chloro-2'-thienyl | H |
| X.368 | CH₃ | CH₂C≡CH | 5'-chloro-2'-thienyl | H |
| X.369 | CH₃ | H | 2'-furyl | H |
| X.370 | C₂H₅ | H | 2'-furyl | H |
| X.371 | CH₂OCH₃ | H | 2'-furyl | H |
| X.372 | CH₃ | CH₂C≡CH | 2'-furyl | H |
| X.373 | CH₃ | H | 5'-chloro-2'-furyl | H |
| X.374 | C₂H₅ | H | 5'-chloro-2'-furyl | H |
| X.375 | CH₂OCH₃ | H | 5'-chloro-2'-furyl | H |
| X.376 | CH₃ | CH₂C≡CH | 5'-chloro-2'-furyl | H |
| X.377 | CH₃ | H | 2'-pyridyl | H |
| X.378 | C₂H₅ | H | 2'-pyridyl | H |
| X.379 | CH₂OCH₃ | H | 2'-pyridyl | H |
| X.380 | CH₃ | CH₂C≡CH | 2'-pyridyl | H |
| X.381 | CH₃ | H | 3'-pyridyl | H |
| X.382 | C₂H₅ | H | 3'-pyridyl | H |
| X.383 | CH₂OCH₃ | H | 3'-pyridyl | H |
| X.384 | CH₃ | CH₂C≡CH | 3'-pyridyl | H |
| X.385 | CH₃ | H | 4'-pyridyl | H |

TABLE X-continued

| Cmpd. No. | $R^2$ | $R^3$ | $R^6$ | $R^7$ |
|---|---|---|---|---|
| X.386 | $C_2H_5$ | H | 4'-pyridyl | H |
| X.387 | $CH_2OCH_3$ | H | 4'-pyridyl | H |
| X.388 | $CH_3$ | $CH_2C\equiv CH$ | 4'-pyridyl | H |
| X.389 | $CH_3$ | H | 6'-chloro-3'-pyridyl | H |
| X.390 | $C_2H_5$ | H | 6'-chloro-3'-pyridyl | H |
| X.391 | $CH_2OCH_3$ | H | 6'-chloro-3'-pyridyl | H |
| X.392 | $CH_3$ | $CH_2C\equiv CH$ | 6'-chloro-3'-pyridyl | H |
| X.393 | $CH_3$ | H | 6'-fluoro-3'-pyridyl | H |
| X.394 | $C_2H_5$ | H | 6'-fluoro-3'-pyridyl | H |
| X.395 | $CH_2OCH_3$ | H | 6'-fluoro-3'-pyridyl | H |
| X.396 | $CH_3$ | $CH_2C\equiv CH$ | 6'-fluoro-3'-pyridyl | H |
| X.397 | $CH_3$ | H | 6'-bromo-3'-pyridyl | H |
| X.398 | $C_2H_5$ | H | 6'-bromo-3'-pyridyl | H |
| X.399 | $CH_2OCH_3$ | H | 6'-bromo-3'-pyridyl | H |
| X.400 | $CH_3$ | $CH_2C\equiv CH$ | 6'-bromo-3'-pyridyl | H |
| X.401 | $CH_3$ | H | 2'-oxazolyl | H |
| X.402 | $CH_3$ | H | 3'-isoxazolyl | H |
| X.403 | $CH_3$ | H | $CH(CH_3)_2$ | H |
| X.404 | $C_2H_5$ | H | $CH(CH_3)_2$ | H |
| X.405 | $CH_2OCH_3$ | H | $CH(CH_3)_2$ | H |
| X.406 | $CH_3$ | $CH_2C\equiv CH$ | $CH(CH_3)_2$ | H |
| X.407 | $CH_3$ | H | 4'-CH=NO(n)-$C_4H_9$-phenyl | H |
| X.408 | $CH_3$ | H | 4'-CH=NO(iso)-$C_4H_9$-phenyl | H |
| X.409 | $CH_3$ | H | 4'-CH=NO(iso)-$C_3H_7$-phenyl | H |
| X.410 | $CH_3$ | H | 4'-CH=NO(n)-$C_3H_7$-phenyl | H |
| X.411 | $CH_3$ | H | $Si(CH_3)_3$ | H |
| X.412 | $C_2H_5$ | H | $Si(CH_3)_3$ | H |
| X.413 | $CH_2OCH_3$ | H | $Si(CH_3)_3$ | H |
| X.414 | CH3 | $CH_2C\equiv CH$ | $Si(CH_3)_3$ | H |
| X.415 | $CH_3$ | H | $CH_2Si(CH_3)_3$ | H |
| X.416 | $C_2H_5$ | H | $CH_2Si(CH_3)_3$ | H |
| X.416 | $CH_2OCH_3$ | H | $CH_2Si(CH_3)_3$ | H |
| X.418 | CH3 | $CH_2C\equiv CH$ | $CH_2Si(CH_3)_3$ | H |
| X.419 | $CH_3$ | H | $CH(CH_3)Si(CH_3)_3$ | H |
| X.420 | $C_2H_5$ | H | $CH(CH_3)Si(CH_3)_3$ | H |
| X.421 | $CH_2OCH_3$ | H | $CH(CH_3)Si(CH_3)_3$ | H |
| X.422 | CH3 | $CH_2C\equiv CH$ | $CH(CH_3)Si(CH_3)_3$ | H |
| X.423 | $CH_3$ | H | $CH_2CH_2Si(CH_3)_3$ | H |
| X.424 | $C_2H_5$ | H | $CH_2CH_2Si(CH_3)_3$ | H |
| X.425 | $CH_2OCH_3$ | H | $CH_2CH_2Si(CH_3)_3$ | H |
| X.426 | CH3 | $CH_2C\equiv CH$ | $CH_2CH_2Si(CH_3)_3$ | H |
| X.427 | $CH_3$ | H | $CH(CH_3)CH_2Si(CH_3)_3$ | H |
| X.428 | $C_2H_5$ | H | $CH(CH_3)CH_2Si(CH_3)_3$ | H |
| X.429 | $CH_2OCH_3$ | H | $CH(CH_3)CH_2Si(CH_3)_3$ | H |
| X.430 | CH3 | $CH_2C\equiv CH$ | $CH(CH_3)CH_2Si(CH_3)_3$ | H |
| X.431 | $CH_3$ | H | $CH_2CH_2CH_2Si(CH_3)_3$ | H |
| X.432 | $C_2H_5$ | H | $CH_2CH_2CH_2Si(CH_3)_3$ | H |
| X.433 | $CH_2OCH_3$ | H | $CH_2CH_2CH_2Si(CH_3)_3$ | H |
| X.434 | CH3 | $CH_2C\equiv CH$ | $CH_2CH_2CH_2Si(CH_3)_3$ | H |
| X.435 | $CH_3$ | H | $CH_2Si(CH_3)_2C_2H_5$ | H |
| X.436 | $CH_3$ | H | $CH_2Si(CH_3)_2CH(CH_3)_2$ | H |
| X.437 | $CH_3$ | H | $CH_2Si(CH_3)_2OCH_3$ | H |
| X.438 | $CH_3$ | H | $CH_2CH_2Si(CH_3)_2OCH_3$ | H |
| X.439 | $CH_3$ | H | $CH(CH_3)Si(CH_3)_2OCH_3$ | H |
| X.440 | $CH_3$ | H | $CH(CH_3)CH_2Si(CH_3)_2OCH_3$ | H |
| X.441 | $CH_3$ | H | 2'-cyclopropyl-cyclopropyl | H |
| X.442 | $C_2H_5$ | H | 2'-cyclopropyl-cyclopropyl | H |
| X.443 | $CH_2OCH_3$ | H | 2'-cyclopropyl-cyclopropyl | H |
| X.444 | $CH_3$ | $CH_2C\equiv CH$ | 2'-cyclopropyl-cyclopropyl | H |
| X.445 | $CH_3$ | H | 2'-(α-$CH_3$-cyclopropyl)-cyclopropyl | H |
| X.446 | $C_2H_5$ | H | 2'-(α-$CH_3$-cyclopropyl)-cyclopropyl | H |
| X.447 | $CH_2OCH_3$ | H | 2'-(α-$CH_3$-cyclopropyl)-cyclopropyl | H |
| X.448 | $CH_3$ | $CH_2C\equiv CH$ | 2'-(α-$CH_3$-cyclopropyl)-cyclopropyl | H |
| X.449 | $CH_3$ | H | 2'-cyclobutyl-cyclopropyl | H |
| X.450 | $CH_3$ | H | 2'-cyclopentyl-cyclopropyl | H |
| X.451 | $CH_3$ | H | 2'-cyclohexyl-cyclopropyl | H |
| X.452 | $CH_3$ | H | 4'-C≡CH-phenyl | H |
| X.453 | $C_2H_5$ | H | 4'-C≡CH-phenyl | H |
| X.454 | $CH_3$ | H | 4'-C≡C—$Si(CH_3)_3$-phenyl | H |
| X.455 | $C_2H_5$ | H | 4'-C≡C—$Si(CH_3)_3$-phenyl | H |
| X.456 | $CH_3$ | H | 4'-C(H)=$CH_2$-phenyl | H |
| X.457 | $C_2H_5$ | H | 4'-C(H)=$CH_2$-phenyl | H |

Table 2 provides 457 compounds of formula (I-2):

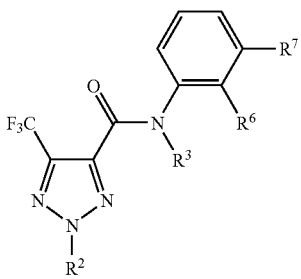

(I-2)

wherein $R^2$, $R^3$, $R^6$ and $R^7$ are as defined in Table 2.

Table 3 provides 457 compounds of formula (I-3):

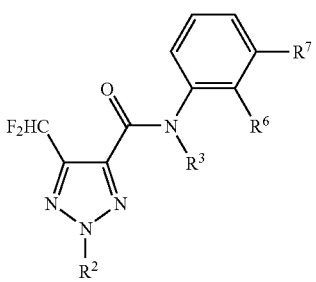

(I-3)

wherein $R^2$, $R^3$, $R^6$ and $R^7$ are as defined in Table 3.

Table 4 provides 457 compounds of formula (I-4):

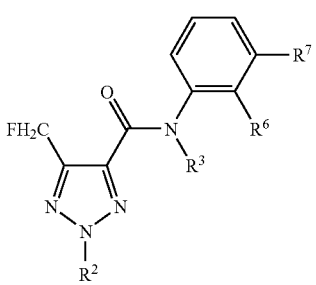

(I-4)

wherein $R^2$, $R^3$, $R^6$ and $R^7$ are as defined in Table 4.

Table 5 provides 457 compounds of formula (I-5):

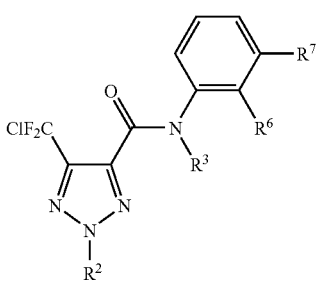

(I-5)

wherein $R^2$, $R^3$, $R^6$ and $R^7$ are as defined in Table 5.

Table 6 provides 457 compounds of formula (I-6):

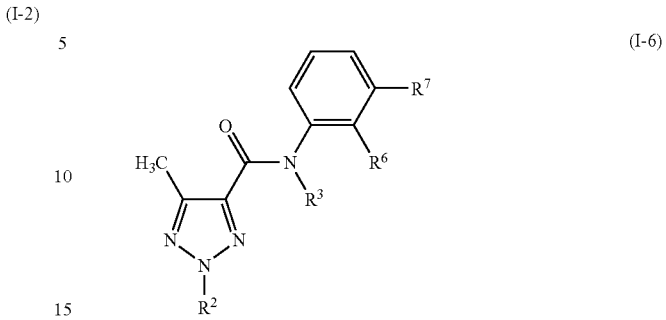

(I-6)

wherein $R^2$, $R^3$, $R^6$ and $R^7$ are as defined in Table 6.

Table 7 provides 457 compounds of formula (I-7):

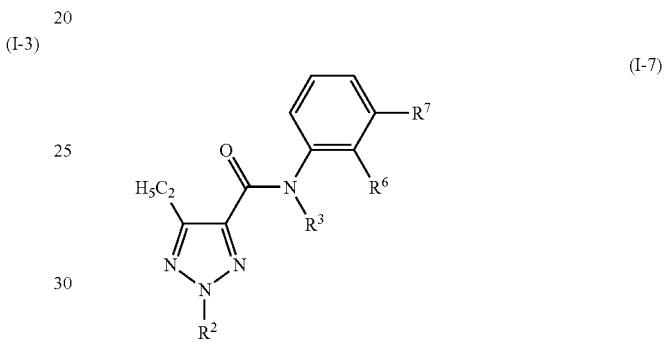

(I-7)

wherein $R^2$, $R^3$, $R^6$ and $R^7$ are as defined in Table 7.

Table Y represents Table 8 [when Y is 8], Table 9 [when Y is 9], Table 10 [when Y is 10], Table 11 [when Y is 11], Table 12 [when Y is 12], Table 13 [when Y is 13], Table 14 [when Y is 14], Table 15 [when Y is 15], Table 16 [when Y is 16], Table 17 [when Y is 17], Table 18 [when Y is 18] and represents Table 19 [when Y is 19].

TABLE Y

| Compound No. | $R^2$ | $R^3$ | $R^6$ |
|---|---|---|---|
| Y.001 | $CH_3$ | H | phenyl |
| Y.002 | $CH_3$ | $CH_2C\equiv CH$ | phenyl |
| Y.003 | $CH_3$ | H | 2'-fluorophenyl |
| Y.004 | $CH_3$ | H | 3'-fluorophenyl |
| Y.005 | $CH_3$ | H | 4'-fluorophenyl |
| Y.006 | $C_2H_5$ | H | 4'-fluorophenyl |
| Y.007 | $CH_2OCH_3$ | H | 4'-fluorophenyl |
| Y.008 | $CH_3$ | $COCH_3$ | 4'-fluorophenyl |
| Y.009 | $CH_3$ | $COCH_2OCH_3$ | 4'-fluorophenyl |
| Y.010 | $CH_3$ | $CH_2C\equiv CH$ | 4'-fluorophenyl |
| Y.011 | $CH_3$ | $CH=C=CH_2$ | 4'-fluorophenyl |
| Y.012 | $CH_3$ | COO-tert-Bu | 4'-fluorophenyl |
| Y.013 | $CH_3$ | H | 2'-chlorophenyl |
| Y.014 | $CH_3$ | H | 3'-chlorophenyl |
| Y.015 | $CH_3$ | H | 4'-chlorophenyl |
| Y.016 | $C_2H_5$ | H | 4'-chlorophenyl |
| Y.017 | $CH_2OCH_3$ | H | 4'-chlorophenyl |
| Y.018 | $CH_3$ | $COCH_3$ | 4'-chlorophenyl |
| Y.019 | $CH_3$ | $COCH_2OCH_3$ | 4'-chlorophenyl |
| Y.020 | $CH_3$ | $CH_2C\equiv CH$ | 4'-chlorophenyl |
| Y.021 | $CH_3$ | $CH=C=CH_2$ | 4'-chlorophenyl |
| Y.022 | $CH_3$ | COO-tert-Bu | 4'-chlorophenyl |
| Y.023 | $CH_3$ | H | 2'-bromophenyl |
| Y.024 | $CH_3$ | H | 3'-bromophenyl |
| Y.025 | $CH_3$ | H | 4'-bromophenyl |

TABLE Y-continued

| Compound No. | R² | R³ | R⁶ |
|---|---|---|---|
| Y.026 | C₂H₅ | H | 4'-bromophenyl |
| Y.027 | CH₂OCH₃ | H | 4'-bromophenyl |
| Y.028 | CH₃ | COCH₃ | 4'-bromophenyl |
| Y.029 | CH₃ | COCH₂OCH₃ | 4'-bromophenyl |
| Y.030 | CH₃ | CH₂C≡CH | 4'-bromophenyl |
| Y.031 | CH₃ | CH=C=CH₂ | 4'-bromophenyl |
| Y.032 | CH₃ | COO-tert-Bu | 4'-bromophenyl |
| Y.033 | CH₃ | H | 2'-iodophenyl |
| Y.034 | CH₃ | H | 3'-iodophenyl |
| Y.035 | CH₃ | H | 4'-iodophenyl |
| Y.036 | CH₃ | H | 2'-CF₃-phenyl |
| Y.037 | CH₃ | H | 3'-CF₃-phenyl |
| Y.038 | CH₃ | H | 4'-CF₃-phenyl |
| Y.039 | C₂H₅ | H | 4'-CF₃-phenyl |
| Y.040 | CH₂OCH₃ | H | 4'-CF₃-phenyl |
| Y.041 | CH₃ | COCH₃ | 4'-CF₃-phenyl |
| Y.042 | CH₃ | COCH₂OCH₃ | 4'-CF₃-phenyl |
| Y.043 | CH₃ | CH₂C≡CH | 4'-CF₃-phenyl |
| Y.044 | CH₃ | COO-tert-Bu | 4'-CF₃-phenyl |
| Y.045 | CH₃ | H | 2'-OCF₃-phenyl |
| Y.046 | CH₃ | H | 3'-OCF₃-phenyl |
| Y.047 | CH₃ | H | 4'-OCF₃-phenyl |
| Y.048 | C₂H₅ | H | 4'-OCF₃-phenyl |
| Y.049 | CH₂OCH₃ | H | 4'-OCF₃-phenyl |
| Y.050 | CH₃ | COCH₃ | 4'-OCF₃-phenyl |
| Y.051 | CH₃ | COCH₂OCH₃ | 4'-OCF₃-phenyl |
| Y.052 | CH₃ | CH₂C≡CH | 4'-OCF₃-phenyl |
| Y.053 | CH₃ | COO-tert-Bu | 4'-OCF₃-phenyl |
| Y.054 | CH₃ | CH=C=CH₂ | 4'-OCF₃-phenyl |
| Y.055 | CH₃ | H | 4'-SCF₃-phenyl |
| Y.056 | CH₃ | H | 2'-CH=NOH-phenyl |
| Y.057 | CH₃ | H | 3'-CH=NOH-phenyl |
| Y.058 | CH₃ | H | 4'-CH=NOH-phenyl |
| Y.059 | CH₃ | H | 2'-CH=NOCH₃-phenyl |
| Y.060 | CH₃ | H | 3'-CH=NOCH₃-phenyl |
| Y.061 | CH₃ | H | 4'-CH=NOCH₃-phenyl |
| Y.062 | CH₃ | H | 2'-CH=NOC₂H₅-phenyl |
| Y.063 | CH₃ | H | 3'-CH=NOC₂H₅-phenyl |
| Y.064 | CH₃ | H | 4'-CH=NOC₂H₅-phenyl |
| Y.065 | CH₃ | H | 2'-CN-phenyl |
| Y.066 | CH₃ | H | 3'-CN-phenyl |
| Y.067 | CH₃ | H | 4'-CN-phenyl |
| Y.068 | CH₃ | H | 2'-NO₂-phenyl |
| Y.069 | CH₃ | H | 3'-NO₂-phenyl |
| Y.070 | CH₃ | H | 4'-NO₂-phenyl |
| Y.071 | CH₃ | H | 3',4'-difluorophenyl |
| Y.072 | C₂H₅ | H | 3',4'-difluorophenyl |
| Y.073 | CH₂OCH₃ | H | 3',4'-difluorophenyl |
| Y.074 | CH₃ | COCH₃ | 3',4'-difluorophenyl |
| Y.075 | CH₃ | COCH₂OCH₃ | 3',4'-difluorophenyl |
| Y.076 | CH₃ | CH₂C≡CH | 3',4'-difluorophenyl |
| Y.077 | CH₃ | COO-tert-Bu | 3',4'-difluorophenyl |
| Y.078 | CH₃ | CH=C=CH₂ | 3',4'-difluorophenyl |
| Y.079 | CH₃ | H | 3',4'-dichlorophenyl |
| Y.080 | C₂H₅ | H | 3',4'-dichlorophenyl |
| Y.081 | CH₂OCH₃ | H | 3',4'-dichlorophenyl |
| Y.082 | CH₃ | COCH₃ | 3',4'-dichlorophenyl |
| Y.083 | CH₃ | COCH₂OCH₃ | 3',4'-dichlorophenyl |
| Y.084 | CH₃ | CH₂C≡CH | 3',4'-dichlorophenyl |
| Y.085 | CH₃ | COO-tert-Bu | 3',4'-dichlorophenyl |
| Y.086 | CH₃ | CH=C=CH₂ | 3',4'-dichlorophenyl |
| Y.087 | CH₃ | H | 4'-chloro-3'-fluoro-phenyl |
| Y.088 | C₂H₅ | H | 4'-chloro-3'-fluoro-phenyl |
| Y.089 | CH₂OCH₃ | H | 4'-chloro-3'-fluoro-phenyl |
| Y.090 | CH₃ | COCH₃ | 4'-chloro-3'-fluoro-phenyl |
| Y.091 | CH₃ | COCH₂OCH₃ | 4'-chloro-3'-fluoro-phenyl |
| Y.092 | CH₃ | CH₂C≡CH | 4'-chloro-3'-fluoro-phenyl |
| Y.093 | CH₃ | COO-tert-Bu | 4'-chloro-3'-fluoro-phenyl |
| Y.094 | CH₃ | CH=C=CH₂ | 4'-chloro-3'-fluoro-phenyl |
| Y.095 | CH₃ | H | 3'-chloro-4'-fluoro-phenyl |
| Y.096 | C₂H₅ | H | 3'-chloro-4'-fluoro-phenyl |
| Y.097 | CH₂OCH₃ | H | 3'-chloro-4'-fluoro-phenyl |
| Y.098 | CH₃ | COCH₃ | 3'-chloro-4'-fluoro-phenyl |
| Y.099 | CH₃ | COCH₂OCH₃ | 3'-chloro-4'-fluoro-phenyl |
| Y.100 | CH₃ | CH₂C≡CH | 3'-chloro-4'-fluoro-phenyl |
| Y.101 | CH₃ | COO-tert-Bu | 3'-chloro-4'-fluoro-phenyl |
| Y.102 | CH₃ | CH=C=CH₂ | 3'-chloro-4'-fluoro-phenyl |
| Y.103 | CH₃ | H | 2'-4'-dichloro-phenyl |
| Y.104 | CH₂OCH₃ | H | 2'-4'-dichloro-phenyl |
| Y.105 | CH₃ | H | 2'-4'-difluoro-phenyl |
| Y.106 | CH₂OCH₃ | H | 2'-4'-difluoro-phenyl |
| Y.107 | CH₃ | H | CH₂CH₂CH₃ |
| Y.108 | C₂H₅ | H | CH₂CH₂CH₃ |
| Y.109 | CH₂OCH₃ | H | CH₂CH₂CH₃ |
| Y.110 | CH₃ | CH₂C≡CH | CH₂CH₂CH₃ |
| Y.111 | CH₃ | H | CH₂CH₂CH₂CH₃ |
| Y.112 | C₂H₅ | H | CH₂CH₂CH₂CH₃ |
| Y.113 | CH₂OCH₃ | H | CH₂CH₂CH₂CH₃ |
| Y.114 | CH₃ | CH₂C≡CH | CH₂CH₂CH₂CH₃ |
| Y.115 | CH₃ | H | CH₂CH₂CH₂(C₂H₅) |
| Y.116 | C₂H₅ | H | CH₂CH₂CH₂(C₂H₅) |
| Y.117 | CH₂OCH₃ | H | CH₂CH₂CH₂(C₂H₅) |
| Y.118 | CH₃ | CH₂C≡CH | CH₂CH₂CH₂(C₂H₅) |
| Y.119 | CH₃ | H | CH₂CH₂CH(CH₃)₂ |
| Y.120 | C₂H₅ | H | CH₂CH₂CH(CH₃)₂ |
| Y.121 | CH₂OCH₃ | H | CH₂CH₂CH(CH₃)₂ |
| Y.122 | CH₃ | COCH₃ | CH₂CH₂CH(CH₃)₂ |
| Y.123 | CH₃ | COCH₂OCH₃ | CH₂CH₂CH(CH₃)₂ |
| Y.124 | CH₃ | CH₂C≡CH | CH₂CH₂CH(CH₃)₂ |
| Y.125 | CH₃ | COO-tert-Bu | CH₂CH₂CH(CH₃)₂ |
| Y.126 | CH₃ | CH=C=CH₂ | CH₂CH₂CH(CH₃)₂ |
| Y.127 | CH₃ | H | CH₂CH₂CH(CH₃)(C₂H₅) |
| Y.128 | C₂H₅ | H | CH₂CH₂CH(CH₃)(C₂H₅) |
| Y.129 | CH₂OCH₃ | H | CH₂CH₂CH(CH₃)(C₂H₅) |
| Y.130 | CH₃ | COCH₃ | CH₂CH₂CH(CH₃)(C₂H₅) |
| Y.131 | CH₃ | COCH₂OCH₃ | CH₂CH₂CH(CH₃)(C₂H₅) |
| Y.132 | CH₃ | CH₂C≡CH | CH₂CH₂CH(CH₃)(C₂H₅) |
| Y.133 | CH₃ | COO-tert-Bu | CH₂CH₂CH(CH₃)(C₂H₅) |
| Y.134 | CH₃ | CH=C=CH₂ | CH₂CH₂CH(CH₃)(C₂H₅) |
| Y.135 | CH₃ | H | CH₂CH₂CH(C₂H₅)₂ |
| Y.136 | C₂H₅ | H | CH₂CH₂CH(C₂H₅)₂ |
| Y.137 | CH₂OCH₃ | H | CH₂CH₂CH(C₂H₅)₂ |
| Y.138 | CH₃ | COCH₃ | CH₂CH₂CH(C₂H₅)₂ |
| Y.139 | CH₃ | COCH₂OCH₃ | CH₂CH₂CH(C₂H₅)₂ |
| Y.140 | CH₃ | CH₂C≡CH | CH₂CH₂CH(C₂H₅)₂ |
| Y.141 | CH₃ | COO-tert-Bu | CH₂CH₂CH(C₂H₅)₂ |
| Y.142 | CH₃ | CH=C=CH₂ | CH₂CH₂CH(C₂H₅)₂ |
| Y.143 | CH₃ | H | CH₂CH₂C(CH₃)₃ |
| Y.144 | C₂H₅ | H | CH₂CH₂C(CH₃)₃ |
| Y.145 | CH₂OCH₃ | H | CH₂CH₂C(CH₃)₃ |
| Y.146 | CH₃ | COCH₃ | CH₂CH₂C(CH₃)₃ |
| Y.147 | CH₃ | COCH₂OCH₃ | CH₂CH₂C(CH₃)₃ |
| Y.148 | CH₃ | CH₂C≡CH | CH₂CH₂C(CH₃)₃ |
| Y.149 | CH₃ | COO-tert-Bu | CH₂CH₂C(CH₃)₃ |
| Y.150 | CH₃ | CH=C=CH₂ | CH₂CH₂C(CH₃)₃ |
| Y.151 | CH₃ | H | CH₂CH₂C(CH₃)₂(C₂H₅) |
| Y.152 | C₂H₅ | H | CH₂CH₂C(CH₃)₂(C₂H₅) |
| Y.153 | CH₂OCH₃ | H | CH₂CH₂C(CH₃)₂(C₂H₅) |
| Y.154 | CH₃ | COCH₃ | CH₂CH₂C(CH₃)₂(C₂H₅) |
| Y.155 | CH₃ | COCH₂OCH₃ | CH₂CH₂C(CH₃)₂(C₂H₅) |
| Y.156 | CH₃ | CH₂C≡CH | CH₂CH₂C(CH₃)₂(C₂H₅) |
| Y.157 | CH₃ | COO-tert-Bu | CH₂CH₂C(CH₃)₂(C₂H₅) |
| Y.158 | CH₃ | CH=C=CH₂ | CH₂CH₂C(CH₃)₂(C₂H₅) |
| Y.159 | CH₃ | H | CH₂CH₂C(CH₃)(C₂H₅)₂ |
| Y.160 | C₂H₅ | H | CH₂CH₂C(CH₃)(C₂H₅)₂ |
| Y.161 | CH₂OCH₃ | H | CH₂CH₂C(CH₃)(C₂H₅)₂ |
| Y.162 | CH₃ | COCH₃ | CH₂CH₂C(CH₃)(C₂H₅)₂ |
| Y.163 | CH₃ | COCH₂OCH₃ | CH₂CH₂C(CH₃)(C₂H₅)₂ |
| Y.164 | CH₃ | CH₂C≡CH | CH₂CH₂C(CH₃)(C₂H₅)₂ |
| Y.165 | CH₃ | COO-tert-Bu | CH₂CH₂C(CH₃)(C₂H₅)₂ |
| Y.166 | CH₃ | CH=C=CH₂ | CH₂CH₂C(CH₃)(C₂H₅)₂ |
| Y.167 | CH₃ | H | CH(CH₃)CH₂CH₃ |
| Y.168 | C₂H₅ | H | CH(CH₃)CH₂CH₃ |
| Y.169 | CH₂OCH₃ | H | CH(CH₃)CH₂CH₃ |
| Y.170 | CH₃ | CH₂C≡CH | CH(CH₃)CH₂CH₃ |
| Y.171 | CH₃ | H | CH(C₂H₅)CH₂CH₃ |
| Y.172 | C₂H₅ | H | CH(C₂H₅)CH₂CH₃ |
| Y.173 | CH₂OCH₃ | H | CH(C₂H₅)CH₂CH₃ |
| Y.174 | CH₃ | CH₂C≡CH | CH(C₂H₅)CH₂CH₃ |
| Y.175 | CH₃ | H | CH(CF₃)CH₂CH₃ |
| Y.176 | C₂H₅ | H | CH(CF₃)CH₂CH₃ |
| Y.177 | CH₂OCH₃ | H | CH(CF₃)CH₂CH₃ |

TABLE Y-continued

| Compound No. | R² | R³ | R⁶ |
|---|---|---|---|
| Y.178 | CH₃ | CH₂C≡CH | CH(CF₃)CH₂CH₃ |
| Y.179 | CH₃ | H | CH(CH₃)CH₂CH₂CH₃ |
| Y.180 | C₂H₅ | H | CH(CH₃)CH₂CH₂CH₃ |
| Y.181 | CH₂OCH₃ | H | CH(CH₃)CH₂CH₂CH₃ |
| Y.182 | CH₃ | CH₂C≡CH | CH(CH₃)CH₂CH₂CH₃ |
| Y.183 | CH₃ | H | CH(C₂H₅)CH₂CH₂CH₃ |
| Y.184 | C₂H₅ | H | CH(C₂H₅)CH₂CH₂CH₃ |
| Y.185 | CH₂OCH₃ | H | CH(C₂H₅)CH₂CH₂CH₃ |
| Y.186 | CH₃ | CH₂C≡CH | CH(C₂H₅)CH₂CH₂CH₃ |
| Y.187 | CH₃ | H | CH(CF₃)CH₂CH₂CH₃ |
| Y.188 | C₂H₅ | H | CH(CF₃)CH₂CH₂CH₃ |
| Y.189 | CH₃ | H | CH(CH₃)CH₂CH(CH₃)₂ |
| Y.190 | C₂H₅ | H | CH(CH₃)CH₂CH(CH₃)₂ |
| Y.191 | CH₂OCH₃ | H | CH(CH₃)CH₂CH(CH₃)₂ |
| Y.192 | CH₃ | COCH₃ | CH(CH₃)CH₂CH(CH₃)₂ |
| Y.193 | CH₃ | COCH₂OCH₃ | CH(CH₃)CH₂CH(CH₃)₂ |
| Y.194 | CH₃ | CH₂C≡CH | CH(CH₃)CH₂CH(CH₃)₂ |
| Y.195 | CH₃ | COO-tert-Bu | CH(CH₃)CH₂CH(CH₃)₂ |
| Y.196 | CH₃ | CH=C=CH₂ | CH(CH₃)CH₂CH(CH₃)₂ |
| Y.197 | CH₃ | H | CH(CH₃)CH₂CH(CH₃)(C₂H₅) |
| Y.198 | C₂H₅ | H | CH(CH₃)CH₂CH(CH₃)(C₂H₅) |
| Y.199 | CH₂OCH₃ | H | CH(CH₃)CH₂CH(CH₃)(C₂H₅) |
| Y.200 | CH₃ | COCH₃ | CH(CH₃)CH₂CH(CH₃)(C₂H₅) |
| Y.201 | CH₃ | COCH₂OCH₃ | CH(CH₃)CH₂CH(CH₃)(C₂H₅) |
| Y.202 | CH₃ | CH₂C≡CH | CH(CH₃)CH₂CH(CH₃)(C₂H₅) |
| Y.203 | CH₃ | COO-tert-Bu | CH(CH₃)CH₂CH(CH₃)(C₂H₅) |
| Y.204 | CH₃ | CH=C=CH₂ | CH(CH₃)CH₂CH(CH₃)(C₂H₅) |
| Y.205 | CH₃ | H | CH(CH₃)CH₂CH(C₂H₅)₂ |
| Y.206 | C₂H₅ | H | CH(CH₃)CH₂CH(C₂H₅)₂ |
| Y.207 | CH₂OCH₃ | H | CH(CH₃)CH₂CH(C₂H₅)₂ |
| Y.208 | CH₃ | COCH₃ | CH(CH₃)CH₂CH(C₂H₅)₂ |
| Y.209 | CH₃ | COCH₂OCH₃ | CH(CH₃)CH₂CH(C₂H₅)₂ |
| Y.210 | CH₃ | CH₂C≡CH | CH(CH₃)CH₂CH(C₂H₅)₂ |
| Y.211 | CH₃ | COO-tert-Bu | CH(CH₃)CH₂CH(C₂H₅)₂ |
| Y.212 | CH₃ | CH=C=CH₂ | CH(CH₃)CH₂CH(C₂H₅)₂ |
| Y.213 | CH₃ | H | CH(C₂H₅)CH₂CH(CH₃)₂ |
| Y.214 | C₂H₅ | H | CH(C₂H₅)CH₂CH(CH₃)₂ |
| Y.215 | CH₂OCH₃ | H | CH(C₂H₅)CH₂CH(CH₃)₂ |
| Y.216 | CH₃ | COCH₃ | CH(C₂H₅)CH₂CH(CH₃)₂ |
| Y.217 | CH₃ | COCH₂OCH₃ | CH(C₂H₅)CH₂CH(CH₃)₂ |
| Y.218 | CH₃ | CH₂C≡CH | CH(C₂H₅)CH₂CH(CH₃)₂ |
| Y.219 | CH₃ | COO-tert-Bu | CH(C₂H₅)CH₂CH(CH₃)₂ |
| Y.220 | CH₃ | CH=C=CH₂ | CH(C₂H₅)CH₂CH(CH₃)₂ |
| Y.221 | CH₃ | H | CH(C₂H₅)CH₂CH(CH₃)(C₂H₅) |
| Y.222 | C₂H₅ | H | CH(C₂H₅)CH₂CH(CH₃)(C₂H₅) |
| Y.223 | CH₂OCH₃ | H | CH(C₂H₅)CH₂CH(CH₃)(C₂H₅) |
| Y.224 | CH₃ | CH₂C≡CH | CH(C₂H₅)CH₂CH(CH₃)(C₂H₅) |
| Y.225 | CH₃ | H | CH(C₂H₅)CH₂CH(C₂H₅)₂ |
| Y.226 | C₂H₅ | H | CH(C₂H₅)CH₂CH(C₂H₅)₂ |
| Y.227 | CH₂OCH₃ | H | CH(C₂H₅)CH₂CH(C₂H₅)₂ |
| Y.228 | CH₃ | CH₂C≡CH | CH(C₂H₅)CH₂CH(C₂H₅)₂ |
| Y.229 | CH₃ | H | CH(CF₃)CH₂CH(CH₃)₂ |
| Y.230 | C₂H₅ | H | CH(CF₃)CH₂CH(CH₃)₂ |
| Y.231 | CH₂OCH₃ | H | CH(CF₃)CH₂CH(CH₃)₂ |
| Y.232 | CH₃ | CH₂C≡CH | CH(CF₃)CH₂CH(CH₃)₂ |
| Y.233 | CH₃ | H | CH(CF₃)CH₂CH(CH₃)(C₂H₅) |
| Y.234 | CH₃ | H | CH(CF₃)CH₂CH(C₂H₅)₂ |
| Y.235 | CH₃ | H | CH(CH₃)CH₂C(CH₃)₃ |
| Y.236 | C₂H₅ | H | CH(CH₃)CH₂C(CH₃)₃ |
| Y.237 | CH₂OCH₃ | H | CH(CH₃)CH₂C(CH₃)₃ |
| Y.238 | CH₃ | COCH₃ | CH(CH₃)CH₂C(CH₃)₃ |
| Y.239 | CH₃ | COCH₂OCH₃ | CH(CH₃)CH₂C(CH₃)₃ |
| Y.240 | CH₃ | CH₂C≡CH | CH(CH₃)CH₂C(CH₃)₃ |
| Y.241 | CH₃ | COO-tert-Bu | CH(CH₃)CH₂C(CH₃)₃ |
| Y.242 | CH₃ | CH=C=CH₂ | CH(CH₃)CH₂C(CH₃)₃ |
| Y.243 | CH₃ | H | CH(CH₃)CH₂C(CH₃)₂(C₂H₅) |
| Y.244 | C₂H₅ | H | CH(CH₃)CH₂C(CH₃)₂(C₂H₅) |
| Y.245 | CH₂OCH₃ | H | CH(CH₃)CH₂C(CH₃)₂(C₂H₅) |
| Y.246 | CH₃ | COCH₃ | CH(CH₃)CH₂C(CH₃)₂(C₂H₅) |
| Y.247 | CH₃ | COCH₂OCH₃ | CH(CH₃)CH₂C(CH₃)₂(C₂H₅) |
| Y.248 | CH₃ | CH₂C≡CH | CH(CH₃)CH₂C(CH₃)₂(C₂H₅) |
| Y.249 | CH₃ | COO-tert-Bu | CH(CH₃)CH₂C(CH₃)₂(C₂H₅) |
| Y.250 | CH₃ | CH=C=CH₂ | CH(CH₃)CH₂C(CH₃)₂(C₂H₅) |
| Y.251 | CH₃ | H | CH(CH₃)CH₂C(CH₃)(C₂H₅)₂ |
| Y.252 | C₂H₅ | H | CH(CH₃)CH₂C(CH₃)(C₂H₅)₂ |
| Y.253 | CH₂OCH₃ | H | CH(CH₃)CH₂C(CH₃)(C₂H₅)₂ |
| Y.254 | CH₃ | CH₂C≡CH | CH(CH₃)CH₂C(CH₃)(C₂H₅)₂ |
| Y.255 | CH₃ | H | CH(C₂H₅)CH₂C(CH₃)₃ |
| Y.256 | C₂H₅ | H | CH(C₂H₅)CH₂C(CH₃)₃ |
| Y.257 | CH₂OCH₃ | H | CH(C₂H₅)CH₂C(CH₃)₃ |
| Y.258 | CH₃ | CH₂C≡CH | CH(C₂H₅)CH₂C(CH₃)₃ |
| Y.259 | CH₃ | H | CH(C₂H₅)CH₂C(CH₃)₂(C₂H₅) |
| Y.260 | C₂H₅ | H | CH(C₂H₅)CH₂C(CH₃)₂(C₂H₅) |
| Y.261 | CH₂OCH₃ | H | CH(C₂H₅)CH₂C(CH₃)₂(C₂H₅) |
| Y.262 | CH₃ | CH₂C≡CH | CH(C₂H₅)CH₂C(CH₃)₂(C₂H₅) |
| Y.263 | CH₃ | H | CH(C₂H₅)CH₂C(CH₃)(C₂H₅)₂ |
| Y.264 | C₂H₅ | H | CH(C₂H₅)CH₂C(CH₃)(C₂H₅)₂ |
| Y.265 | CH₂OCH₃ | H | CH(C₂H₅)CH₂C(CH₃)(C₂H₅)₂ |
| Y.266 | CH₃ | CH₂C≡CH | CH(C₂H₅)CH₂C(CH₃)(C₂H₅)₂ |
| Y.267 | CH₃ | H | CH(CF₃)CH₂C(CH₃)₃ |
| Y.268 | C₂H₅ | H | CH(CF₃)CH₂C(CH₃)₃ |
| Y.269 | CH₂OCH₃ | H | CH(CF₃)CH₂C(CH₃)₃ |
| Y.270 | CH₃ | CH₂C≡CH | CH(CF₃)CH₂C(CH₃)₃ |
| Y.271 | CH₃ | H | CH(CF₃)CH₂C(CH₃)₂(C₂H₅) |
| Y.272 | C₂H₅ | H | CH(CF₃)CH₂C(CH₃)₂(C₂H₅) |
| Y.273 | CH₂OCH₃ | H | CH(CF₃)CH₂C(CH₃)₂(C₂H₅) |
| Y.274 | CH₃ | CH₂C≡CH | CH(CF₃)CH₂C(CH₃)₂(C₂H₅) |
| Y.275 | CH₃ | H | CH(CF₃)CH₂C(CH₃)(C₂H₅)₂ |
| Y.276 | C₂H₅ | H | CH(CF₃)CH₂C(CH₃)(C₂H₅)₂ |
| Y.277 | CH₂OCH₃ | H | CH(CF₃)CH₂C(CH₃)(C₂H₅)₂ |
| Y.278 | CH₃ | CH₂C≡CH | CH(CF₃)CH₂C(CH₃)(C₂H₅)₂ |
| Y.279 | CH₃ | H | 2'-tert-butyl-cyclopropyl |
| Y.280 | C₂H₅ | H | 2'-tert-butyl-cyclopropyl |
| Y.281 | CH₂OCH₃ | H | 2'-tert-butyl-cyclopropyl |
| Y.282 | CH₃ | CH₂C≡CH | 2'-tert-butyl-cyclopropyl |
| Y.283 | CH₃ | H | 2'-isobutyl-cyclopropyl |
| Y.284 | C₂H₅ | H | 2'-isobutyl-cyclopropyl |
| Y.285 | CH₂OCH₃ | H | 2'-isobutyl-cyclopropyl |
| Y.286 | CH₃ | CH₂C≡CH | 2'-isobutyl-cyclopropyl |
| Y.287 | CH₃ | H | 4',4'-dimethyl-cyclobutyl |
| Y.288 | C₂H₅ | H | 4',4'-dimethyl-cyclobutyl |
| Y.289 | CH₂OCH₃ | H | 4',4'-dimethyl-cyclobutyl |
| Y.290 | CH₃ | CH₂C≡CH | 4',4'-dimethyl-cyclobutyl |
| Y.291 | CH₃ | H | cyclopentyl |
| Y.292 | C₂H₅ | H | cyclopentyl |
| Y.293 | CH₂OCH₃ | H | cyclopentyl |
| Y.294 | CH₃ | CH₂C≡CH | cyclopentyl |
| Y.295 | CH₃ | H | 3'-methyl-cyclopentyl |
| Y.296 | C₂H₅ | H | 3'-methyl-cyclopentyl |
| Y.297 | CH₂OCH₃ | H | 3'-methyl-cyclopentyl |
| Y.298 | CH₃ | CH₂C≡CH | 3'-methyl-cyclopentyl |
| Y.299 | CH₃ | H | cyclohexyl |
| Y.300 | C₂H₅ | H | cyclohexyl |
| Y.301 | CH₂OCH₃ | H | cyclohexyl |
| Y.302 | CH₃ | CH₂C≡CH | cyclohexyl |
| Y.303 | CH₃ | H | 3'-methyl-cyclohexyl |
| Y.304 | C₂H₅ | H | 3'-methyl-cyclohexyl |
| Y.305 | CH₂OCH₃ | H | 3'-methyl-cyclohexyl |
| Y.306 | CH₃ | CH₂C≡CH | 3'-methyl-cyclohexyl |
| Y.307 | CH₃ | H | 4'-methyl-cyclohexyl |
| Y.308 | C₂H₅ | H | 4'-methyl-cyclohexyl |
| Y.309 | CH₂OCH₃ | H | 4'-methyl-cyclohexyl |
| Y.310 | CH₃ | CH₂C≡CH | 4'-methyl-cyclohexyl |
| Y.311 | CH₃ | H | cycloheptyl |
| Y.312 | C₂H₅ | H | cycloheptyl |
| Y.313 | CH₂OCH₃ | H | cycloheptyl |
| Y.314 | CH₃ | CH₂C≡CH | cycloheptyl |
| Y.315 | CH₃ | H | 2'-thienyl |
| Y.316 | C₂H₅ | H | 2'-thienyl |
| Y.317 | CH₂OCH₃ | H | 2'-thienyl |
| Y.318 | CH₃ | CH₂C≡CH | 2'-thienyl |
| Y.319 | CH₃ | H | 3'-thienyl |
| Y.320 | C₂H₅ | H | 3'-thienyl |
| Y.321 | CH₂OCH₃ | H | 3'-thienyl |
| Y.322 | CH₃ | CH₂C≡CH | 3'-thienyl |
| Y.323 | CH₃ | H | 5'-chloro-2'-thienyl |
| Y.324 | C₂H₅ | H | 5'-chloro-2'-thienyl |
| Y.325 | CH₂OCH₃ | H | 5'-chloro-2'-thienyl |
| Y.326 | CH₃ | CH₂C≡CH | 5'-chloro-2'-thienyl |
| Y.327 | CH₃ | H | 2'-furyl |
| Y.328 | C₂H₅ | H | 2'-furyl |
| Y.329 | CH₂OCH₃ | H | 2'-furyl |

TABLE Y-continued

| Compound No. | R² | R³ | R⁶ |
|---|---|---|---|
| Y.330 | CH₃ | CH₂C≡CH | 2'-furyl |
| Y.331 | CH₃ | H | 5'-chloro-2'-furyl |
| Y.332 | C₂H₅ | H | 5'-chloro-2'-furyl |
| Y.333 | CH₂OCH₃ | H | 5'-chloro-2'-furyl |
| Y.334 | CH₃ | CH₂C≡CH | 5'-chloro-2'-furyl |
| Y.335 | CH₃ | H | 2'-pyridyl |
| Y.336 | C₂H₅ | H | 2'-pyridyl |
| Y.337 | CH₂OCH₃ | H | 2'-pyridyl |
| Y.338 | CH₃ | CH₂C≡CH | 2'-pyridyl |
| Y.339 | CH₃ | H | 3'-pyridyl |
| Y.340 | C₂H₅ | H | 3'-pyridyl |
| Y.341 | CH₂OCH₃ | H | 3'-pyridyl |
| Y.342 | CH₃ | CH₂C≡CH | 3'-pyridyl |
| Y.343 | CH₃ | H | 4'-pyridyl |
| Y.344 | C₂H₅ | H | 4'-pyridyl |
| Y.345 | CH₂OCH₃ | H | 4'-pyridyl |
| Y.346 | CH₃ | CH₂C≡CH | 4'-pyridyl |
| Y.347 | CH₃ | H | 6'-chloro-3'-pyridyl |
| Y.348 | C₂H₅ | H | 6'-chloro-3'-pyridyl |
| Y.349 | CH₂OCH₃ | H | 6'-chloro-3'-pyridyl |
| Y.350 | CH₃ | CH₂C≡CH | 6'-chloro-3'-pyridyl |
| Y.351 | CH₃ | H | 6'-fluoro-3'-pyridyl |
| Y.352 | C₂H₅ | H | 6'-fluoro-3'-pyridyl |
| Y.353 | CH₂OCH₃ | H | 6'-fluoro-3'-pyridyl |
| Y.354 | CH₃ | CH₂C≡CH | 6'-fluoro-3'-pyridyl |
| Y.355 | CH₃ | H | 6'-bromo-3'-pyridyl |
| Y.356 | C₂H₅ | H | 6'-bromo-3'-pyridyl |
| Y.357 | CH₂OCH₃ | H | 6'-bromo-3'-pyridyl |
| Y.358 | CH₃ | CH₂C≡CH | 6'-bromo-3'-pyridyl |
| Y.359 | CH₃ | H | 2'-oxazolyl |
| Y.360 | CH₃ | H | 3'-isoxazolyl |
| Y.361 | CH₃ | H | CH(CH₃)₂ |
| Y.362 | C₂H₅ | H | CH(CH₃)₂ |
| Y.363 | CH₂OCH₃ | H | CH(CH₃)₂ |
| Y.364 | CH₃ | CH₂C≡CH | CH(CH₃)₂ |

Table 8 provides 364 compounds of formula (I-8):

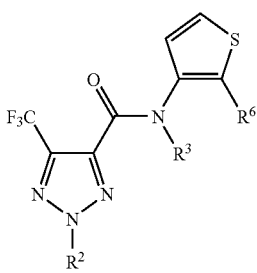

(I-8)

wherein R², R³, and R⁶ are as defined in Table 8.

Table 9 provides 364 compounds of formula (I-9):

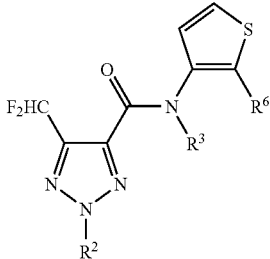

(I-9)

wherein R², R³, and R⁶ are as defined in Table 9.

Table 10 provides 364 compounds of formula (I-10):

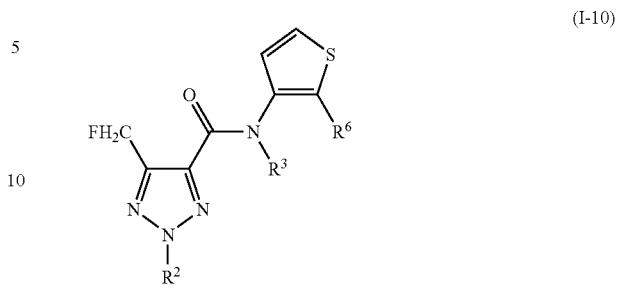

(I-10)

wherein R², R³, and R⁶ are as defined in Table 10.

Table 11 provides 364 compounds of formula (I-11):

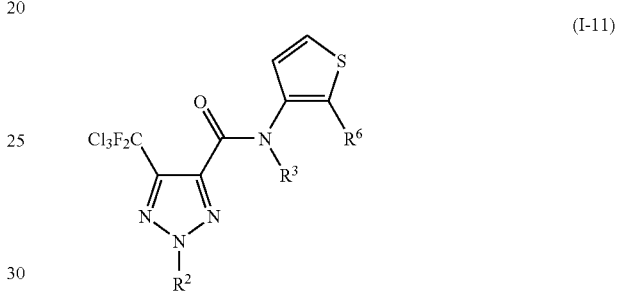

(I-11)

wherein R², R³, and R⁶ are as defined in Table 11.

Table 12 provides 364 compounds of formula (I-12):

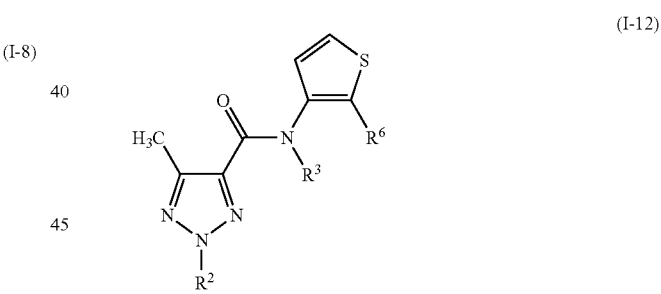

(I-12)

wherein R², R³, and R⁶ are as defined in Table 12.

Table 13 provides 364 compounds of formula (I-13):

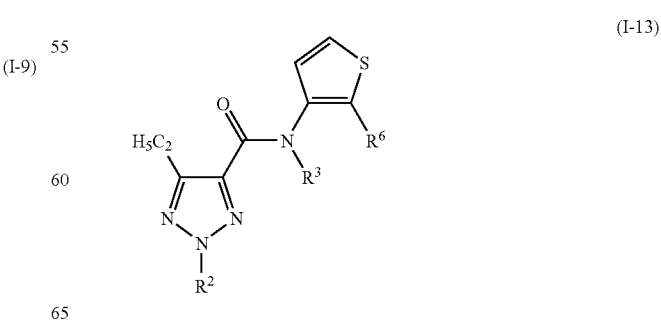

(I-13)

wherein R², R³, and R⁶ are as defined in Table 13.

Table 14 provides 364 compounds of formula (I-14):

(I-14)

wherein R², R³, and R⁶ are as defined in Table 14.

Table 15 provides 364 compounds of formula (I-15):

(I-15)

wherein R², R³, and R⁶ are as defined in Table 15.

Table 16 provides 364 compounds of formula (I-16):

(I-16)

wherein R², R³, and R⁶ are as defined in Table 16.

Table 17 provides 364 compounds of formula (I-17):

(I-17)

wherein R², R³, and R⁶ are as defined in Table 17.

Table 18 provides 364 compounds of formula (I-18):

(I-18)

wherein R², R³, and R⁶ are as defined in Table 18.

Table 19 provides 364 compounds of formula (I-19):

(I-19)

wherein R², R³, and R⁶ are as defined in Table 19.

Table Z represents Table 20 [when Z is 20], Table 21 [when Z is 21], Table 22 [when Z is 22], Table 23 [when Z is 23], Table 24 [when Z is 24] and represents Table 25 [when Z is 25].

TABLE Z

| Compound No. | R² | R³ | A |
|---|---|---|---|
| Z.001 | CH₃ | H | (indane) |
| Z.002 | C₂H₅ | H | (indane) |
| Z.003 | CH₃OCH₃ | H | (indane) |

TABLE Z-continued

| Compound No. | R² | R³ | A |
|---|---|---|---|
| Z.004 | CH₃ | CH₂C≡CH | (4-indanyl) |
| Z.005 | CH₃ | H | (1-methyl-4-indanyl) |
| Z.006 | C₂H₅ | H | (1-methyl-4-indanyl) |
| Z.007 | CH₂OCH₃ | H | (1-methyl-4-indanyl) |
| Z.008 | CH₃ | CH₂C≡CH | (1-methyl-4-indanyl) |
| Z.009 | CH₃ | H | (3-methyl-4-indanyl) |
| Z.010 | C₂H₅ | H | (3-methyl-4-indanyl) |
| Z.011 | CH₂OCH₃ | H | (3-methyl-4-indanyl) |
| Z.012 | CH₃ | CH₂C≡CH | (3-methyl-4-indanyl) |
| Z.013 | CH₃ | H | (1,3-dimethyl-4-indanyl) |
| Z.014 | C₂H₅ | H | (1,3-dimethyl-4-indanyl) |
| Z.015 | CH₂OCH₃ | H | (1,3-dimethyl-4-indanyl) |
| Z.016 | CH₃ | CH₂C≡CH | (1,3-dimethyl-4-indanyl) |
| Z.017 | CH₃ | H | (1,1,3-trimethyl-4-indanyl) |
| Z.018 | C₂H₅ | H | (1,1,3-trimethyl-4-indanyl) |
| Z.019 | CH₂OCH₃ | H | (1,1,3-trimethyl-4-indanyl) |

TABLE Z-continued

| Compound No. | R² | R³ | A |
|---|---|---|---|
| Z.020 | CH₃ | CH₂C≡CH | 4-methyl-1,1,3-trimethyl-2,3-dihydro-1H-indene |
| Z.021 | CH₃ | H | 1,1,3-trimethyl-1,3-dihydroisobenzofuran-4-yl |
| Z.022 | C₂H₅ | H | 1,1,3-trimethyl-1,3-dihydroisobenzofuran-4-yl |
| Z.023 | CH₂OCH₃ | H | 1,1,3-trimethyl-1,3-dihydroisobenzofuran-4-yl |
| Z.024 | CH₃ | CH₂C≡CH | 1,1,3-trimethyl-1,3-dihydroisobenzofuran-4-yl |
| Z.025 | CH₃ | H | 1,3-dimethyl-1,3-dihydroisobenzofuran-4-yl |
| Z.026 | C₂H₅ | H | 1,3-dimethyl-1,3-dihydroisobenzofuran-4-yl |
| Z.027 | CH₂OCH₃ | H | 1,3-dimethyl-1,3-dihydroisobenzofuran-4-yl |
| Z.028 | CH₃ | CH₂C≡CH | 1,3-dimethyl-1,3-dihydroisobenzofuran-4-yl |
| Z.029 | CH₃ | H | 1-methyl-1,3-dihydroisobenzofuran-4-yl |
| Z.030 | C₂H₅ | H | 1-methyl-1,3-dihydroisobenzofuran-4-yl |
| Z.031 | CH₂OCH₃ | H | 1-methyl-1,3-dihydroisobenzofuran-4-yl |
| Z.032 | CH₃ | CH₂C≡CH | 1-methyl-1,3-dihydroisobenzofuran-4-yl |
| Z.033 | CH₃ | H | 3-methyl-1,3-dihydroisobenzofuran-4-yl |
| Z.034 | C₂H₅ | H | 3-methyl-1,3-dihydroisobenzofuran-4-yl |

TABLE Z-continued
| Compound No. | R² | R³ | A |
|---|---|---|---|
| Z.035 | CH₂OCH₃ | H | 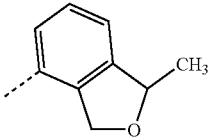 |
| Z.036 | CH₃ | CH₂C≡CH | 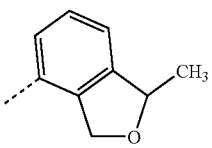 |
| Z.037 | CH₃ | H | 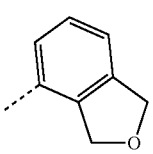 |
| Z.038 | C₂H₅ | H | 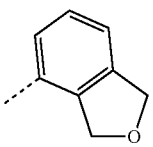 |
| Z.039 | CH₂OCH₃ | H | 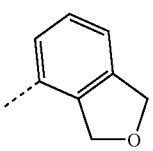 |
| Z.040 | CH₃ | CH₂C≡CH | 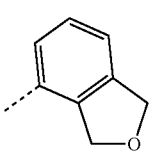 |
| Z.041 | CH₃ | H | 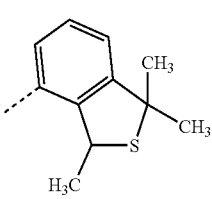 |
| Z.042 | C₂H₅ | H | 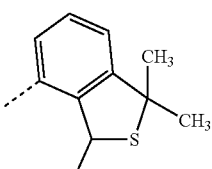 |
| Z.043 | CH₂OCH₃ | H | 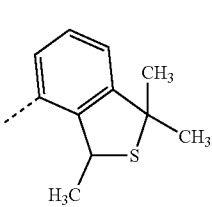 |
TABLE Z-continued
| Compound No. | R² | R³ | A |
|---|---|---|---|
| Z.044 | CH₃ | CH₂C≡CH | 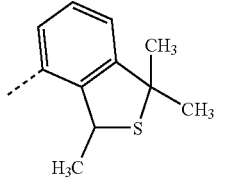 |
| Z.045 | CH₃ | H | 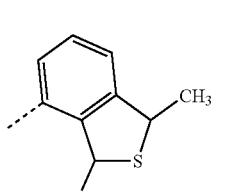 |
| Z.046 | C₂H₅ | H | 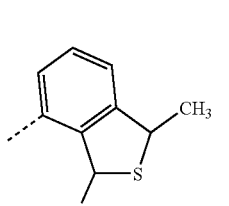 |
| Z.047 | CH₂OCH₃ | H | 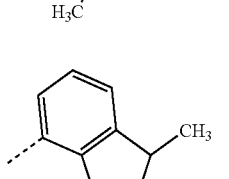 |
| Z.048 | CH₃ | CH₂C≡CH | 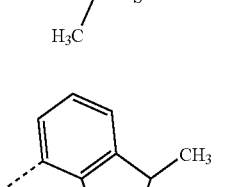 |
| Z.049 | CH₃ | H | 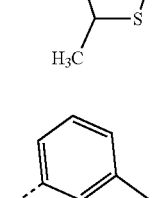 |
| Z.050 | C₂H₅ | H | 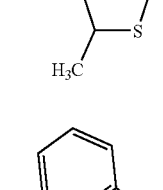 |

TABLE Z-continued
| Compound No. | R² | R³ | A |
|---|---|---|---|
| Z.051 | CH₂OCH₃ | H | 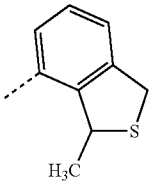 |
| Z.052 | CH₃ | CH₂C≡CH | 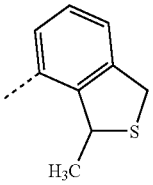 |
| Z.053 | CH₃ | H | 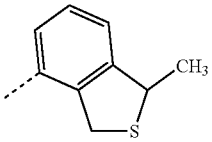 |
| Z.054 | C₂H₅ | H | 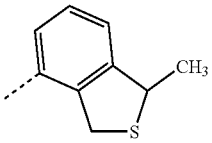 |
| Z.055 | CH₂OCH₃ | H | 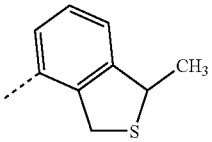 |
| Z.056 | CH₃ | CH₂C≡CH | 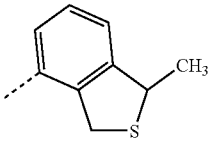 |
| Z.057 | CH₃ | H | 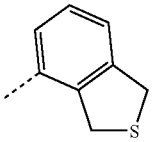 |
| Z.058 | C₂H₅ | H | 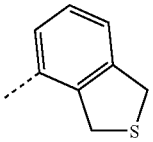 |
| Z.059 | CH₂OCH₃ | H | 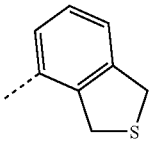 |
| Z.060 | CH₃ | CH₂C≡CH | 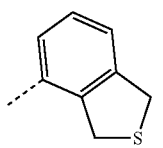 |
| Z.061 | CH₃ | H | 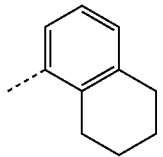 |
| Z.062 | C₂H₅ | H | 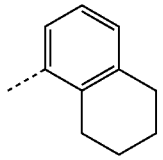 |
| Z.063 | CH₂OCH₃ | H | 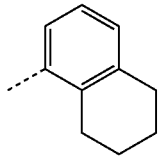 |
| Z.064 | CH₃ | CH₂C≡CH | 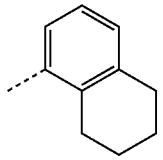 |
| Z.065 | CH₃ | H | 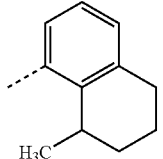 |
| Z.066 | C₂H₅ | H | 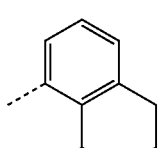 |
| Z.067 | CH₂OCH₃ | H | 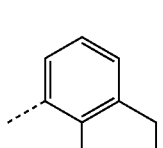 |

TABLE Z-continued

| Compound No. | R² | R³ | A |
|---|---|---|---|
| Z.068 | CH₃ | CH₂C≡CH | tetrahydronaphthalene with CH₃ |
| Z.069 | CH₃ | H | tetrahydronaphthalene with CH₃ |
| Z.070 | C₂H₅ | H | tetrahydronaphthalene with CH₃ |
| Z.071 | CH₂OCH₃ | H | tetrahydronaphthalene with CH₃ |
| Z.072 | CH₃ | CH₂C≡CH | tetrahydronaphthalene with CH₃ |
| Z.073 | CH₃ | H | tetrahydronaphthalene with 2 CH₃ |
| Z.074 | C₂H₅ | H | tetrahydronaphthalene with 2 CH₃ |
| Z.075 | CH₂OCH₃ | H | tetrahydronaphthalene with 2 CH₃ |
| Z.076 | CH₃ | CH₂C≡CH | tetrahydronaphthalene with 2 CH₃ |
| Z.077 | CH₃ | H | tetrahydronaphthalene with 3 CH₃ |
| Z.078 | C₂H₅ | H | tetrahydronaphthalene with 3 CH₃ |
| Z.079 | CH₂OCH₃ | H | tetrahydronaphthalene with 3 CH₃ |
| Z.080 | CH₃ | CH₂C≡CH | tetrahydronaphthalene with 3 CH₃ |
| Z.081 | CH₃ | H | dihydronaphthalene with 2 CH₃ |
| Z.082 | C₂H₅ | H | dihydronaphthalene with 2 CH₃ |
| Z.083 | CH₂OCH₃ | H | dihydronaphthalene with 2 CH₃ |

TABLE Z-continued

| Compound No. | R² | R³ | A |
|---|---|---|---|
| Z.084 | CH₃ | CH₂C≡CH | 4,8-dimethylnaphth-1-yl |
| Z.085 | CH₃ | H | 8-methylnaphth-1-yl |
| Z.086 | C₂H₅ | H | 8-methylnaphth-1-yl |
| Z.087 | CH₂OCH₃ | H | 8-methylnaphth-1-yl |
| Z.088 | CH₃ | CH₂C≡CH | 8-methylnaphth-1-yl |
| Z.089 | CH₃ | H | 5-methylnaphth-1-yl |
| Z.090 | C₂H₅ | H | 5-methylnaphth-1-yl |
| Z.091 | CH₂OCH₃ | H | 5-methylnaphth-1-yl |
| Z.092 | CH₃ | CH₂C≡CH | 5-methylnaphth-1-yl |
| Z.093 | CH₃ | H | naphth-1-yl |
| Z.094 | C₂H₅ | H | naphth-1-yl |
| Z.095 | CH₂OCH₃ | H | naphth-1-yl |
| Z.096 | CH₃ | CH₂C≡CH | naphth-1-yl |
| Z.097 | CH₃ | H | bicyclic |
| Z.098 | C₂H₅ | H | bicyclic |
| Z.099 | CH₂OCH₃ | H | bicyclic |
| Z.100 | CH₃ | CH₂C≡CH | bicyclic |

TABLE Z-continued
| Compound No. | R² | R³ | A |
|---|---|---|---|
| Z.101 | CH₃ | H | 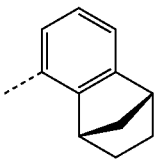 |
| Z.102 | C₂H₅ | H | 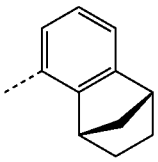 |
| Z.103 | CH₂OCH₃ | H | 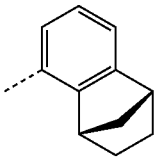 |
| Z.104 | CH₃ | CH₂C≡CH | 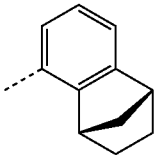 |
| Z.105 | CH₃ | H | 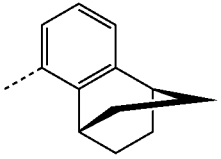 |
| Z.106 | CH₃ | H | 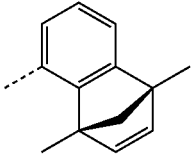 |
| Z.107 | CH₃ | H | 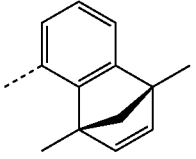 |
| Z.108 | CH₃ | H | 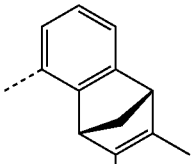 |
TABLE Z-continued
| Compound No. | R² | R³ | A |
|---|---|---|---|
| Z.109 | CH₃ | H | 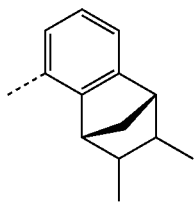 |
| Z.110 | CH₃ | H | 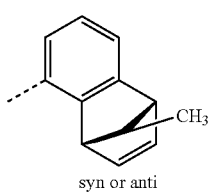<br>syn or anti |
| Z.111 | CH₃ | H | 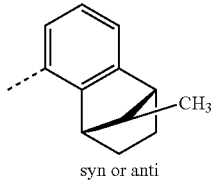<br>syn or anti |
| Z.112 | CH₃ | H | 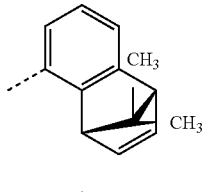 |
| Z.113 | CH₃ | H | 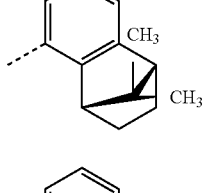 |
| Z.114 | CH₃ | H | 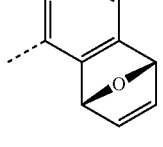 |
| Z.115 | CH₃ | H | 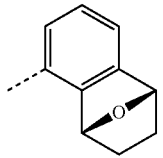 |
| Z.116 | C₂H₅ | H | 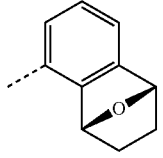 |

TABLE Z-continued

| Compound No. | R² | R³ | A |
|---|---|---|---|
| Z.117 | CH₂OCH₃ | H | |
| Z.118 | CH₃ | CH₂C≡CH | |
| Z.119 | CH₃ | H | |
| Z.120 | CH₃ | H | |
| Z.121 | C₂H₅ | H | |
| Z.122 | CH₂OCH₃ | H | |
| Z.123 | CH₃ | CH₂C≡CH | |
| Z.124 | CH₃ | H | |
| Z.125 | CH₃ | H | |
| Z.126 | CH₃ | H | |
| Z.127 | CH₃ | H | |
| Z.128 | CH₃ | H | |
| Z.129 | CH₃ | H | |
| Z.130 | CH₃ | H | |
| Z.131 | CH₃ | H | |
| Z.132 | C₂H₅ | H | |
| Z.133 | CH₂OCH₃ | H | |

TABLE Z-continued

| Compound No. | R² | R³ | A |
|---|---|---|---|
| Z.134 | CH₃ | CH₂C≡CH | (naphtho-thiophene structure) |
| Z.135 | CH₃ | H | (naphtho-thiophene structure) |
| Z.136 | CH₃ | H | (naphtho-thiophene structure) |
| Z.137 | C₂H₅ | H | (naphtho-thiophene structure) |
| Z.138 | CH₂OCH₃ | H | (naphtho-thiophene structure) |
| Z.139 | CH₃ | CH₂C≡CH | (naphtho-thiophene structure) |
| Z.140 | CH₃ | H | (naphtho-thiophene structure) |
| Z.141 | CH₃ | H | (naphtho-thiophene structure) |
| Z.142 | CH₃ | H | (naphtho-thiophene structure) |

TABLE Z-continued

| Compound No. | R² | R³ | A |
|---|---|---|---|
| Z.143 | CH₃ | H | (naphtho-thiophene structure) |
| Z.144 | CH₃ | H | (naphtho-thiophene structure) |
| Z.145 | CH₃ | H | (naphtho-thiophene structure) |
| Z.146 | CH₃ | H | (naphtho-N-CH₃ structure) |
| Z.147 | CH₃ | H | (naphtho-N-CH₃ structure) |
| Z.148 | CH₃ | H | (naphtho-N-CH₂CH₂ structure) |
| Z.149 | CH₃ | H | (naphtho-N-CHO structure) |
| Z.150 | CH₃ | H | (naphtho-N-CHO structure) |

TABLE Z-continued
| Compound No. | R² | R³ | A |
|---|---|---|---|
| Z.151 | CH₃ | H | 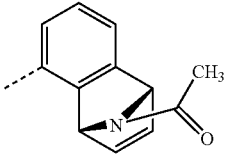 |
| Z.152 | CH₃ | H | 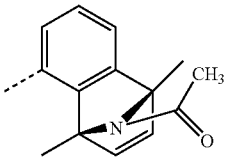 |
| Z.153 | CH₃ | H | 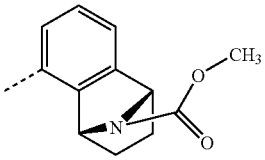 |
| Z.154 | CH₃ | H | 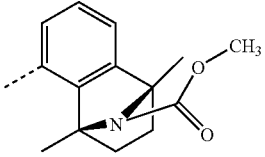 |
| Z.155 | CH₃ | H | 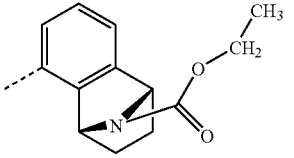 |
| Z.156 | CH₃ | H | 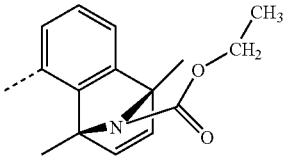 |
| Z.157 | CH₃ | H | 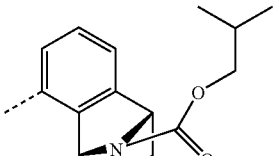 |
| Z.158 | CH₃ | H | 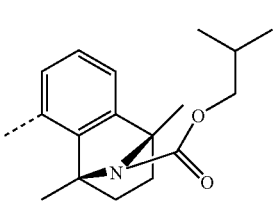 |
| Z.159 | CH₃ | H | 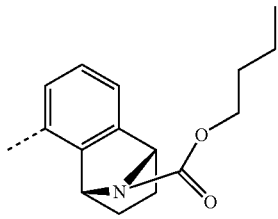 |
| Z.160 | CH₃ | H | 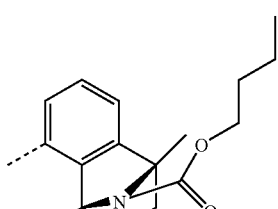 |
| Z.161 | CH₃ | H | 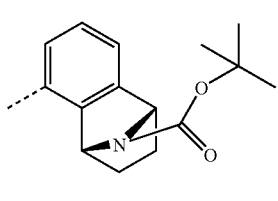 |
| Z.162 | CH₃ | H | 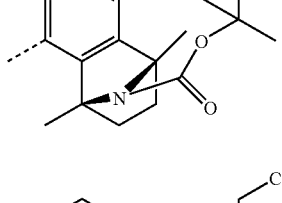 |
| Z.163 | CH₃ | H | 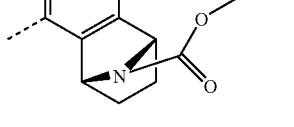 |
| Z.164 | CH₃ | H | 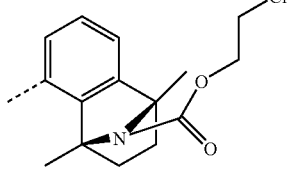 |
| Z.165 | CH₃ | H | 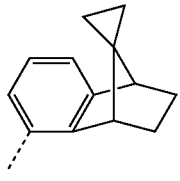 |

TABLE Z-continued
| Compound No. | R² | R³ | A |
|---|---|---|---|
| Z.166 | CH₃ | H | 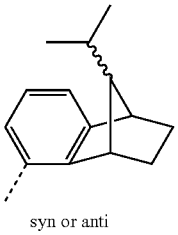<br>syn or anti |
| Z.167 | CH₃ | H | 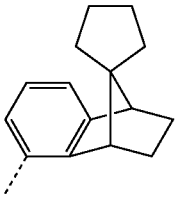 |
| Z.168 | CH₃ | H | 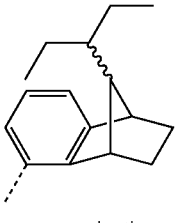<br>syn and anti |
| Z.169 | CH₃ | H | 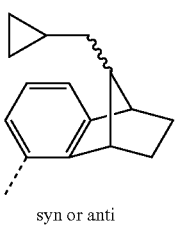<br>syn or anti |
| Z.170 | CH₃ | H | 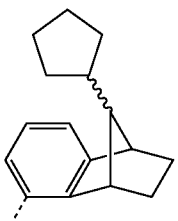<br>syn and anti |
| Z.171 | CH₃ | H | 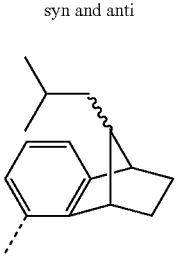<br>syn or anti |
TABLE Z-continued
| Compound No. | R² | R³ | A |
|---|---|---|---|
| Z.172 | CH₃ | H | 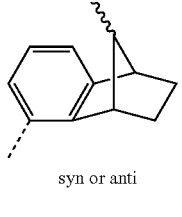<br>syn or anti |
| Z.173 | CH₃ | H | 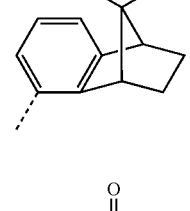 |
| Z.174 | CH₃ | H | 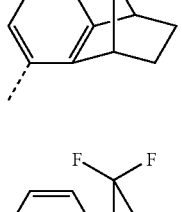 |
| Z.175 | CH₃ | H | 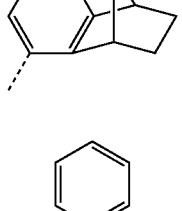 |
| Z.176 | CH₃ | H | 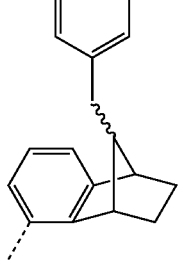<br>syn or anti |
| Z.177 | CH₃ | H | 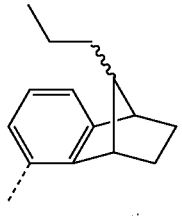<br>syn or anti |

TABLE Z-continued

| Compound No. | R² | R³ | A |
|---|---|---|---|
| Z.178 | CH₃ | H | 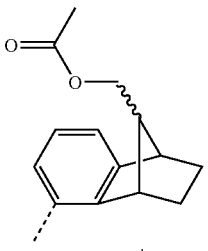 syn or anti |
| Z.179 | CH₃ | H | 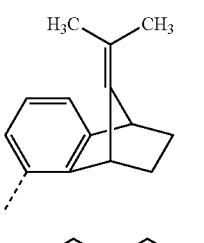 |
| Z.180 | CH₃ | H | 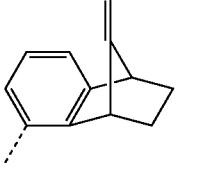 |
| Z.181 | CH₃ | H | 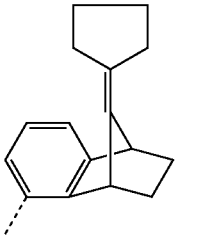 |
| Z.182 | CH₃ | H | 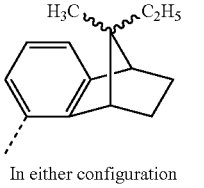 In either configuration |

Table 20 provides 182 compounds of formula (I-20):

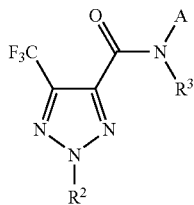

(I-20)

wherein R², R³ and A are as defined in Table 20.

Table 21 provides 182 compounds of formula (I-21):

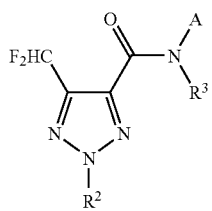

(I-21)

wherein R², R³ and A are as defined in Table 21.

Table 22 provides 182 compounds of formula (I-22):

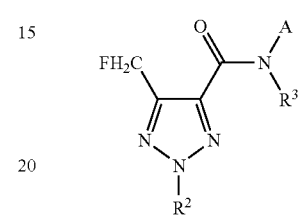

(I-22)

wherein R², R³ and A are as defined in Table 22.

Table 23 provides 182 compounds of formula (I-23):

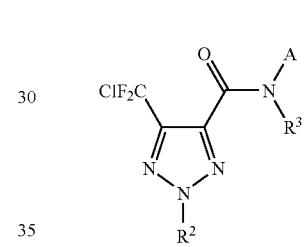

(I-23)

wherein R², R³ and A are as defined in Table 23.

Table 24 provides 182 compounds of formula (I-24):

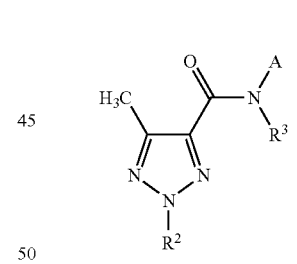

(I-24)

wherein R², R³ and A are as defined in Table 24.

Table 25 provides 182 compounds of formula (I-25):

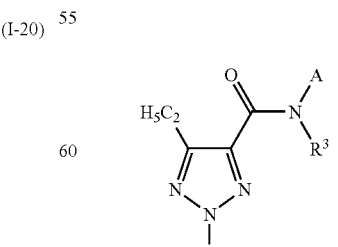

(I-25)

wherein R², R³ and A are as defined in Table 25.

Table 26 provides 133 compounds of formula (IIIa) where $R^{13}$, $R^{14}$, $R^{15}$, $R^{16}$, Q and X are as defined in Table 26. Q is shown to be either a single bond (—) or a double bond (=).

TABLE 26

| Compound. No. | $R^{13}$ | $R^{14}$ | $R^{15}$ | $R^{16}$ | Q | X |
|---|---|---|---|---|---|---|
| 26.001 | CH₃ | CH₃ | H | H | = | O |
| 26.002 | CH₃ | H | H | H | = | O |
| 26.003 | H | CH₃ | H | H | = | O |
| 26.004 | CH₃ | CH₃ | C(O)CH₃ | H | = | O |
| 26.005 | CH₃ | CH₃ | H | C(O)CH₃ | = | O |
| 26.006 | CH₃ | C(O)CH₃ | H | H | = | O |
| 26.007 | H | H | H | H | = | O |
| 26.008 | CF₃ | CF₃ | H | H | = | O |
| 26.009 | OCH₃ | OCH₃ | H | H | = | O |
| 26.010 | H | H | CH₃ | CH₃ | = | O |
| 26.011 | C₂H₅ | C₂H₅ | H | H | = | O |
| 26.012 | CH₃ | H | CH₃ | H | = | O |
| 26.013 | H | CH₃ | H | CH₃ | = | O |
| 26.014 | CH₃ | CH₃ | H | H | — | O |
| 26.015 | CH₃ | H | H | H | — | O |
| 26.016 | H | CH₃ | H | H | — | O |
| 26.017 | CH₃ | CH₃ | C(O)CH₃ | H | — | O |
| 26.018 | CH₃ | CH₃ | H | C(O)CH₃ | — | O |
| 26.019 | CH₃ | C(O)CH₃ | H | H | — | O |
| 26.020 | H | H | H | H | — | O |
| 26.021 | CF₃ | CF₃ | H | H | — | O |
| 26.022 | OCH₃ | OCH₃ | H | H | — | O |
| 26.023 | H | H | CH₃ | CH₃ | — | O |
| 26.024 | C₂H₅ | C₂H₅ | H | H | — | O |
| 26.025 | CH₃ | H | CH₃ | H | — | O |
| 26.026 | H | H | H | H | — | CH₂ |
| 26.027 | CH₃ | H | CH₃ | H | — | CH₂ |
| 26.028 | CH₃ | H | CH₃ | H | = | CH₂ |
| 26.029 | H | CH₃ | H | CH₃ | — | CH₂ |
| 26.030 | H | CH₃ | H | CH₃ | = | CH₂ |
| 26.031 | CH₃ | CH₃ | CH₃ | CH₃ | = | CH₂ |
| 26.032 | CH₃ | CH₃ | CH₃ | CH₃ | — | CH₂ |
| 26.033 | CH₃ | CH₃ | CH₃ | CH₃ | = | CH(CH₃) syn or anti |
| 26.034 | CH₃ | CH₃ | CH₃ | CH₃ | — | CH(CH₃) syn or anti |
| 26.035 | H | H | H | H | = | CH(CH₃) syn or anti |
| 26.036 | H | H | H | H | — | CH(CH₃) syn or anti |
| 26.037 | H | H | H | H | — | CH(C₂H₅) syn or anti |
| 26.038 | H | H | H | H | — | CH₂CH₂ |
| 26.039 | CH₃ | CH₃ | H | H | = | CH₂CH₂ |
| 26.040 | CH₃ | CH₃ | H | H | — | CH₂CH₂ |
| 26.041 | H | H | CH₃ | CH₃ | = | CH₂CH₂ |
| 26.042 | H | H | CH₃ | CH₃ | — | CH₂CH₂ |
| 26.043 | H | H | OCH₃ | H | — | CH₂CH₂ |
| 26.044 | H | H | H | OCH₃ | — | CH₂CH₂ |
| 26.045 | H | H | H | H | — | CH₂CH₂CH₂ |
| 26.046 | H | H | H | H | = | CH₂CH₂CH₂ |
| 26.047 | H | H | CH₃ | CH₃ | = | C(CH₃)₂ |
| 26.048 | H | H | CH₃ | CH₃ | — | C(CH₃)₂ |
| 26.049 | CH₃ | CH₃ | CH₃ | CH₃ | = | C(CH₃)₂ |
| 26.050 | CH₃ | CH₃ | CH₃ | CH₃ | — | C(CH₃)₂ |
| 26.051 | CH₃ | H | CH₃ | H | — | C(CH₃)₂ |
| 26.052 | H | CH₃ | H | CH₃ | — | C(CH₃)₂ |
| 26.053 | CH₃ | H | CH₃ | H | = | C(CH₃)₂ |
| 26.054 | H | CH₃ | H | CH₃ | = | C(CH₃)₂ |
| 26.055 | CH₃ | CH₃ | CH₃ | CH₃ | — | C(CH₃)(C₂H₅) |
| 26.056 | H | H | H | H | — | C(CH₃)₂ |
| 26.057 | H | H | H | H | = | C(CH₃)₂ |
| 26.058 | CH₃ | CH₃ | H | H | — | C(CH₃)₂ |
| 26.059 | CH₃ | CH₃ | H | H | = | C(CH₃)₂ |
| 26.060 | H | H | H | H | = | C(OCH₃)₂ |
| 26.061 | H | H | H | H | — | CH(OCH₃) |
| 26.062 | H | H | H | H | = | S |
| 26.063 | H | H | H | H | — | S |
| 26.064 | CH₃ | CH₃ | H | H | = | S |
| 26.065 | CH₃ | CH₃ | H | H | — | S |
| 26.066 | H | H | CH₃ | CH₃ | = | S |
| 26.067 | H | H | CH₃ | CH₃ | — | S |
| 26.068 | OCH₃ | OCH₃ | H | H | = | S |
| 26.069 | OCH₃ | OCH₃ | H | H | — | S |
| 26.070 | H | CH₃ | H | H | = | S |
| 26.071 | H | CH₃ | H | H | — | S |

TABLE 26-continued

| Compound. No. | R¹³ | R¹⁴ | R¹⁵ | R¹⁶ | Q | X |
|---|---|---|---|---|---|---|
| 26.072 | CH₃ | H | H | H | = | S |
| 26.073 | CH₃ | H | H | H | — | S |
| 26.074 | CH₃ | H | CH₃ | H | = | S |
| 26.075 | CH₃ | H | CH₃ | H | — | S |
| 26.076 | H | CH₃ | H | CH₃ | = | S |
| 26.077 | H | CH₃ | H | CH₃ | — | S |
| 26.078 | H | OCH₃ | H | H | = | S |
| 26.079 | H | OCH₃ | H | H | — | S |
| 26.080 | OCH₃ | H | H | H | = | S |
| 26.081 | OCH₃ | H | H | H | — | S |
| 26.082 | CH₃ | H | CH₃ | CH₃ | = | S |
| 26.083 | CH₃ | H | CH₃ | CH₃ | — | S |
| 26.084 | H | CH₃ | CH₃ | CH₃ | = | S |
| 26.085 | H | CH₃ | CH₃ | CH₃ | — | S |
| 26.086 | H | H | CH₃ | H | = | S |
| 26.087 | H | H | CH₃ | H | — | S |
| 26.088 | H | H | H | CH₃ | = | S |
| 26.089 | H | H | H | CH₃ | — | S |
| 26.090 | H | H | OCH₃ | H | = | S |
| 26.091 | H | H | OCH₃ | H | — | S |
| 26.092 | H | H | H | OCH₃ | = | S |
| 26.093 | H | H | H | OCH₃ | — | S |
| 26.094 | H | H | H | H | = | N(CH₃) |
| 26.095 | H | H | H | H | — | N(CH₃) |
| 26.096 | CH₃ | CH₃ | H | H | = | N(CH₃) |
| 26.097 | CH₃ | CH₃ | H | H | — | N(CH₃) |
| 26.098 | H | H | H | H | = | N(C₂H₅) |
| 26.099 | H | H | H | H | — | N(C₂H₅) |
| 26.100 | H | H | H | H | — | NH |
| 26.101 | H | H | H | H | — | NC(O)OC(CH₃)₃ |
| 26.102 | CH₃ | CH₃ | H | H | — | NC(O)OC(CH₃)₃ |
| 26.103 | H | H | H | H | — | N(CHO) |
| 26.104 | H | H | H | H | — | N(C(O)CH₃) |
| 26.105 | CH₃ | CH₃ | H | H | — | N(C(O)CH₃) |
| 26.106 | H | H | H | H | — | N(C(O)OCH₃) |
| 26.107 | CH₃ | CH₃ | H | H | — | N(C(O)OCH₃) |
| 26.108 | H | H | H | H | — | N(C(O)OC₂H₅) |
| 26.109 | CH₃ | CH₃ | H | H | — | N(C(O)OC₂H₅) |
| 26.110 | H | H | H | H | — | N(C(O)OCH₂CH₂Cl) |
| 26.111 | CH₃ | CH₃ | H | H | — | N(C(O)OCH₂CH₂Cl) |
| 26.112 | H | H | H | H | — | N(C(O)OC₄H₉-(n)) |
| 26.113 | CH₃ | CH₃ | H | H | — | N(C(O)OC₄H₉-(n)) |
| 26.114 | H | H | H | H | — | N(C(O)OC₄H₉-(i)) |
| 26.115 | CH₃ | CH₃ | H | H | — | N(C(O)OC₄H₉-(i)) |
| 26.116 | H | H | H | H | — | CH(C₃H₇-(i)) syn or anti |
| 26.117 | H | H | H | H | — | CH(C₃H₇-(n)) syn or anti |
| 26.118 | H | H | H | H | — | CH(C₄H₉-(i)) syn or anti |
| 26.119 | H | H | H | H | — | C(C₂H₄-(c)) |
| 26.120 | H | H | H | H | — | C(C₄H₈-(c)) |
| 26.121 | H | H | H | H | — | CHCH(C₂H₅)₂ syn or anti |
| 26.122 | H | H | H | H | — | CHCH₂(C₃H₅-(c)) syn or anti |
| 26.123 | H | H | H | H | — | CH(C₅H₉-(c)) syn or anti |
| 26.124 | H | H | H | H | — | CHCH₂OC(=O)CH₃ syn or anti |
| 26.125 | H | H | H | H | — | CH(CH=O) syn or anti |
| 26.126 | H | H | H | H | — | CHCH₂OH |
| 26.127 | H | H | H | H | — | C(OC₃H₇-(n))2 |
| 26.128 | H | H | H | H | — | C=O |
| 26.129 | H | H | H | H | — | CHCH₂—C₆H₅ syn or anti |
| 26.130 | H | H | H | H | — | C=C(CH₃)₂ |
| 26.131 | H | H | H | H | — | C=C(C₂H₅)₂ |
| 26.132 | H | H | H | H | — | cyclopentylidene |
| 26.133 | H | H | H | H | — | C(CH₃)(C₂H₅) In either configuration |

Table ZZ represents Table 27 (when ZZ is 27) and represents Table 28 (when ZZ is 28).

TABLE ZZ

| Compound No. | R³ | R⁶ | R² | R¹ |
|---|---|---|---|---|
| ZZ.1 | H | SiMe₃ | Me | CF₃ |
| ZZ.2 | H | SiMe₃ | Me | CF₂H |
| ZZ.3 | H | CH₂SiMe₃ | Me | CF₃ |
| ZZ.4 | H | CH₂SiMe₃ | Me | CF₂H |
| ZZ.5 | propargyl | CH₂SiMe₃ | Me | CF₃ |
| ZZ.6 | H | CHMeSiMe₃ | Me | CF₃ |
| ZZ.7 | H | CHMeSiMe₃ | Me | CF₂H |
| ZZ.8 | propargyl | CHMeSiMe₃ | Me | CF₃ |
| ZZ.9 | allenyl | CHMeSiMe₃ | Me | CF₃ |
| ZZ.10 | COMe | CHMeSiMe₃ | Me | CF₃ |
| ZZ.11 | H | CHMeSiMe₃ | Me | Me |
| ZZ.12 | H | (CH₂)₂SiMe₃ | Me | CF₃ |
| ZZ.13 | H | (CH₂)₂SiMe₃ | Me | CF₂H |
| ZZ.14 | propargyl | (CH₂)₂SiMe₃ | Me | CF₃ |
| ZZ.15 | H | (CH₂)₂SiMe₃ | Me | Me |
| ZZ.16 | H | (CH₂)₂SiMe₃ | CF₃ | CF₃ |
| ZZ.17 | H | CHMeCH₂SiMe₃ | Me | CF₃ |
| ZZ.18 | H | CHMeCH₂SiMe₃ | Me | CF₂H |
| ZZ.19 | propargyl | CHMeCH₂SiMe₃ | Me | CF₃ |
| ZZ.20 | propargyl | CHMeCH₂SiMe₃ | Me | CF₂H |
| ZZ.21 | H | CHMeCH₂SiMe₃ | Me | Me |
| ZZ.22 | H | CHMeCH₂SiMe₃ | CF₃ | CF₃ |
| ZZ.23 | COMe | CHMeCH₂SiMe₃ | Me | CF₃ |
| ZZ.24 | H | (CH₂)₃SiMe₃ | Me | CF₃ |
| ZZ.25 | H | (CH₂)₃SiMe₃ | Me | CF₂H |
| ZZ.26 | H | CH₂Si(Me₂)Et | Me | CF₃ |
| ZZ.27 | H | CH₂Si(Me₂)Et | Me | CF₂H |
| ZZ.28 | H | CH₂Si(Me₂)CHMe₂ | Me | CF₃ |
| ZZ.29 | H | CH₂Si(Me₂)CHMe₂ | Me | CF₂H |
| ZZ.30 | H | CH₂CHMeSiMe₃ | Me | CF₃ |
| ZZ.31 | H | CH₂CHMeSiMe₃ | Me | CF₂H |
| ZZ.32 | H | CMe₂CH₂SiMe₃ | Me | CF₃ |
| ZZ.33 | H | CMe₂CH₂SiMe₃ | Me | CF₂H |
| ZZ.34 | H | CHMeCHMeSiMe₃ | Me | CF₂H |
| ZZ.35 | H | CHMeCHMeSiMe₃ | Me | CF₃ |
| ZZ.36 | H | CH₂CMe₂SiMe₃ | Me | CF₃ |
| ZZ.37 | H | CH₂CMe₂SiMe₃ | Me | CF₂H |
| ZZ.38 | H | CHMe(CH₂)₂SiMe₃ | Me | CF₂H |
| ZZ.39 | H | CHMe(CH₂)₂SiMe₃ | Me | CF₃ |
| ZZ.40 | H | (CH₂)₂SiMe₃ | CH₂OMe | CH₂Me |
| ZZ.41 | H | (CH₂)₂SiMe₃ | CH₂OCH₂Me | CH₂Me |
| ZZ.42 | H | SiMe₂CH₂CHMe₂ | Me | CF₃ |

Table 27 provides 42 compounds of formula (I-27) where R¹, R², R³ and R⁶ are as defined in Table 9.

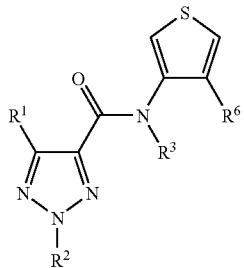

(I-27)

Table 28 provides 42 compounds of formula (I-28) where R¹, R², R³ and R⁶ are as defined in Table 10.

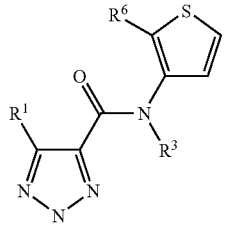

(I-28)

Throughout this description, temperatures are given in degrees Celsius; "NMR" means nuclear magnetic resonance spectrum; MS stands for mass spectrum; "%" is percent by weight, unless corresponding concentrations are indicated in other units; "syn" refers to a syn configuration of the relevant substituent with respect to the anellated benzene ring; and "anti" refers to an anti configuration of the relevant substituent with respect to the anellated benzene ring.

The following abbreviations are used throughout this description:
m.p.=melting point b.p.=boiling point.
s=singlet br=broad
d=doublet dd=doublet of doublets
t=triplet q=quartet
m=multiplet ppm=parts per million Table 29 shows selected melting point data for compounds of Tables 1 to 28.

TABLE 29

| Compound No. | m.p./(° C.) |
|---|---|
| 1.03 | 56-57 |
| 1.13 | 176-177 |
| 1.15 | liquid |
| 1.50 | 64-66 |
| 2.005 | 146-147 |
| 2.017 | 148 |
| 2.029 | 148-149 |
| 2.067 | 165-166 |
| 2.070 | 139-142 |
| 2.219 | 94.6-95.4 |
| 2.273 | 125-126 |
| 2.321 | 124-125 |
| 2.411 | 117-118 |
| 2.427 | 103-105 |
| 2.423 | 105 |
| 2.445 (trans) | 98-99 |
| 2.452 | 123-125 |
| 2.454 | 161-163 |
| 2.456 | 122-123 |
| 3.005 | 143-145 |
| 3.017 | 155-156 |
| 3.029 | 154-155 |
| 3.067 | 144-145 |
| 3.070 | 136-137 |
| 3.219 | 71-73 |
| 3.273 | 87-88 |
| 3.321 | 121-122 |
| 3.407 | 83-85 |
| 3.411 | 91-93 |
| 3.427 | 75-76 |
| 3.423 | 121-122 |
| 3.445 | 94-95 |
| 3.452 | 161-162 |
| 3.454 | 144-145 |
| 3.456 | 133-135 |
| 4.017 | 158-159 |
| 4.273 | 89-91 |
| 4.411 | 84-86 |

TABLE 29-continued

| Compound No. | m.p./(° C.) |
|---|---|
| 4.445 | 84-85 |
| 4.452 | 143-144 |
| 4.456 | 122-124 |
| 8.189 | 104-106 |
| 9.189 | 82-83 |
| 20.017 | 167-169 |
| 20.021 | 121-122 |
| 20.065 | 144-145 |
| 20.073 | 157-158 |
| 20.097 | 108-109 |
| 20.101 | 155-157 |
| 20.115 | 137-139 |
| 20.120 | 160-161 |
| 20.147 | 159-162 (decomposition) |
| 20.148 | 133-139 |
| 20.149 | amorphous |
| 20.161 | amorphous |
| 20.166 (syn:anti 90:10) | 150-153 |
| 20.166 (syn:anti 34:66) | 111-116 |
| 20.168 (syn:anti 40:60) | 102-120 |
| 20.169 (syn:anti 86:14) | 105-109 |
| 20.170 (syn:anti 74:26) | amorphous |
| 20.171 (syn:anti 16:84) | 106-107 |
| 20.171 (syn:anti 81:19) | amorphous |
| 20.176 (syn:anti 80:20) | 126-129 |
| 20.179 | 187-189 |
| 20.180 | 109-110 |
| 21.097 | 107-109 |
| 21.101 | 120-122 |
| 21.017 | 175-177 |
| 21.021 | 125-126 |
| 21.065 | 114-116 |
| 21.073 | 135-137 |
| 21.105 | 140-143 |
| 21.114 | 189-191 |
| 21.115 | 164-166 |
| 21.120 | 172-175 |
| 21.148 | 134-136 |
| 21.152 | 170-172 |
| 21.153 | amorphous |
| 21.154 | 120-122 |
| 21.155 | amorphous |
| 21.161 | amorphous |
| 21.165 (syn) | 106-108 |
| 21.166 (syn:anti 90:10) | 148-149 |
| 22.101 | 97-98 |
| 22.115 | 135-138 |
| 22.147 | viscous |
| 22.148 | 130-132 |

TABLE 29-continued

| Compound No. | m.p./(° C.) |
|---|---|
| 22.149 | amorphous |
| 22.161 | amorphous |
| 26.001 | 92-96 |
| 26.007 | 121-124 |
| 26.014 | 92-93 |
| 26.015 | 115-116 |
| 26.016 | 92-93 |
| 26.020 | 75-76 |
| 26.026 | 63-64 |
| 26.038 | 74-75 |
| 26.095 | 139-140 |
| 26.099 | viscous |
| 26.100 | viscous |
| 26.101 | 89-90 |
| 26.102 | 94-95 |
| 26.103 | 176-177 |
| 26.105 | 110-111 |
| 26.106 | 104-105 |
| 26.107 | 114-115 |
| 26.108 | viscous |
| 26.110 | viscous |
| 26.112 | viscous |
| 26.114 | viscous |
| 26.116 (syn:anti 86:14) | waxy solid |
| 26.116 (syn:anti 35:65) | oil |
| 26.118 (syn:anti 10:90) | viscous |
| 26.118 (syn:anti 82:18) | viscous |
| 26.119 | oil |
| 26.121 (syn:anti 50:50) | oil |
| 26.122 (syn:anti 84:14) | oil |
| 26.123 (syn:anti 75:25) | 73-78 |
| 26.128 (syn:anti 74:26) | oil |
| 26.129 | 81-82 |
| 26.130 | oil |

The compounds according to formula (I) may be prepared according to the following reaction schemes.

(a) Preparation of a Compound of Formula (II).

Schemes 1, 2 and 3 demonstrate that a compound of formula E, H, K, L, N, O, P, R, S, T, U, V, W, Y or Z [where $R^1$ and $R^2$ are as defined above for formula (II); and R' is $C_{1-5}$ alkyl] {each of which is a compound of formula (II), as defined above} may be prepared by a reaction sequence starting with a 1,2,3-triazole-4,5-dicarboxylic acid diester of formula A [Y. Tanaka et al., *Tetrahedron*, 29, 3271 (1973)] [where each R' is, independently, $C_{1-5}$ alkyl] (preferably the dimethyl ester).

Scheme 1

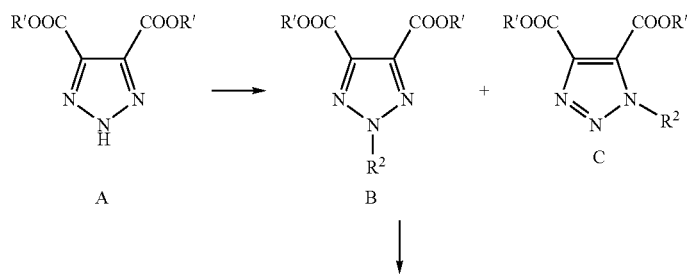

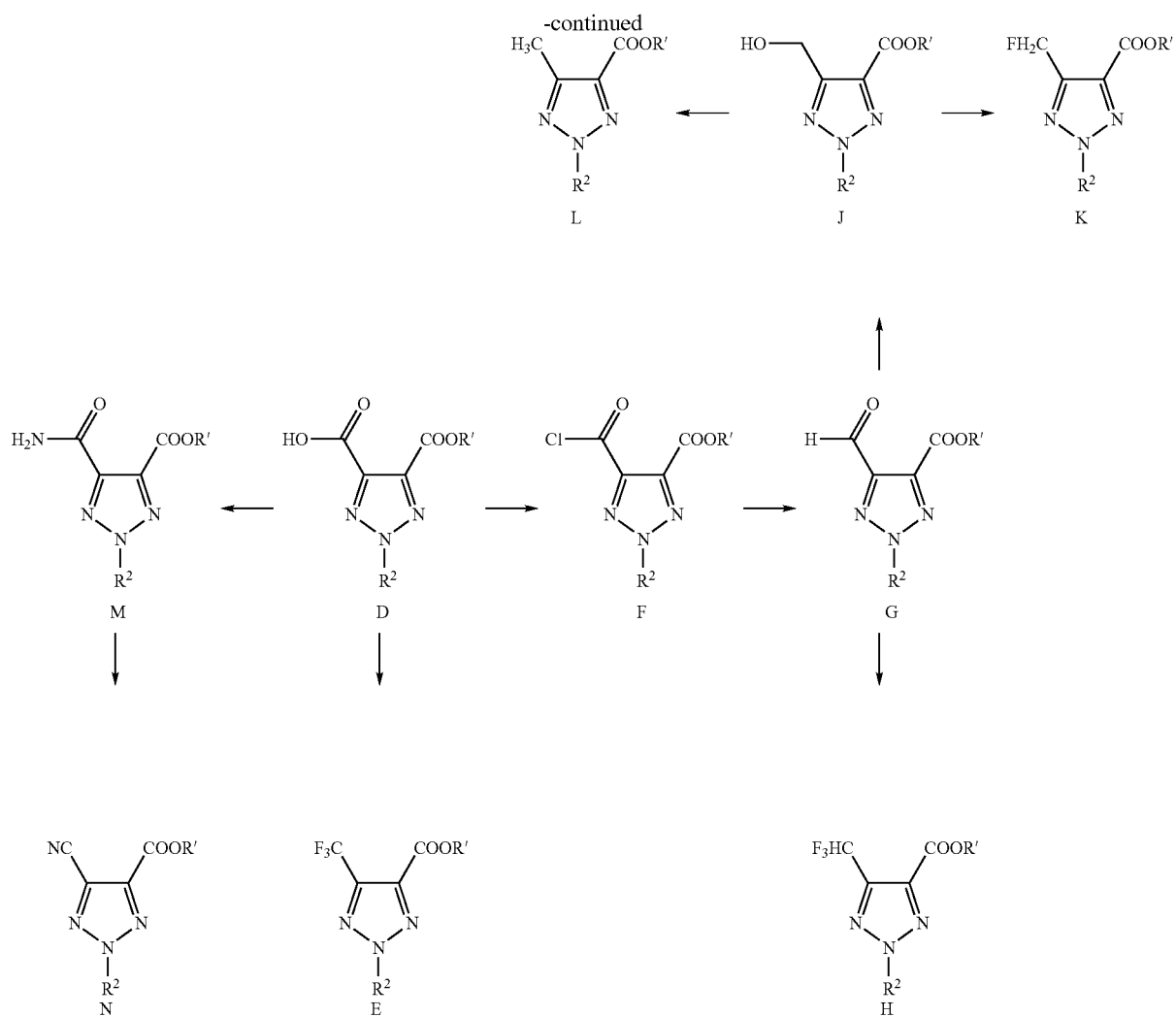

Treatment of A with an alkylating agent [such as $R^2$-halo (where $R^2$ is as defined above for formula (II); and halo is preferably iodo) or an appropriate sulphate, sulphonate or carbonate ester] in the presence of a base [such as $K_2CO_3$, $Na_2CO_3$ or $NEt_3$] in a suitable solvent [such as acetonitrile, DMF or dimethylacetamide] at ambient to elevated temperatures furnishes a mixture of regioisomers, of formulae B and C, which may be separated by conventional methods. Saponification of a compound of formula B with up to one equivalent of a base [such as KOH, NaOH or LiOH] in a protic solvent [such as methanol], preferably under reflux conditions, provides a mono-ester of formula D. Subsequent reaction of a compound of formula D with a fluorinating agent [such as DAST (diethylamino sulphur trifloride) or, preferably, $SF_4$] in the presence of hydrofluoric acid gives a 5-$CF_3$-1,2,3-triazole-4-carboxylic acid ester of formula E.

Alternatively, treatment of a compound of formula D with a chlorinating agent [such as thionyl chloride or phosgene] under standard conditions results in an acid chloride of formula F which may be reduced catalytically in an inert solvent [for example ethyl acetate or THF] in the presence of a base [for example Hünig base] to give an aldehyde-ester of formula G (modified Rosenmund conditions). Fluorination of a compound of formula G by means of DAST, dimethoxy-DAST or $SF_4$ in the presence of hydrofluoric acid, optionally with solvent, preferably at elevated temperatures, forms a 5-difluoromethyl-1,2,3-triazole-4-carboxylic acid ester of formula H.

Metal hydride reduction of a compound of formula G [for example by $NaBH_4$ or $LiBH_4$] in methanol provides a 5-hydroxymethyl-1,2,3-triazole of formula J, from which a 5-fluoromethyl derivative of formula K may be obtained by fluorination under mild conditions, preferably with DAST at low temperatures (0 to −78° C.) in an inert solvent [such as dichloromethane].

Alternatively, hydride reduction of a compound of formula J by conventional methods [for example via its mesylate, tosylate or iodide] results in a 5-methyl-1,2,3-triazole of formula L.

Chlorination of compound of formula D [for example by thionyl chloride] followed by treatment with ammonia, preferably in a protic solvent [such as water, methanol or ethanol] furnishes an amide of formula M from which a 5-cyano-1,2,3-triazole of formula N may be obtained by means of a dehydrating agent [such as phosphorylchloride].

Scheme 2

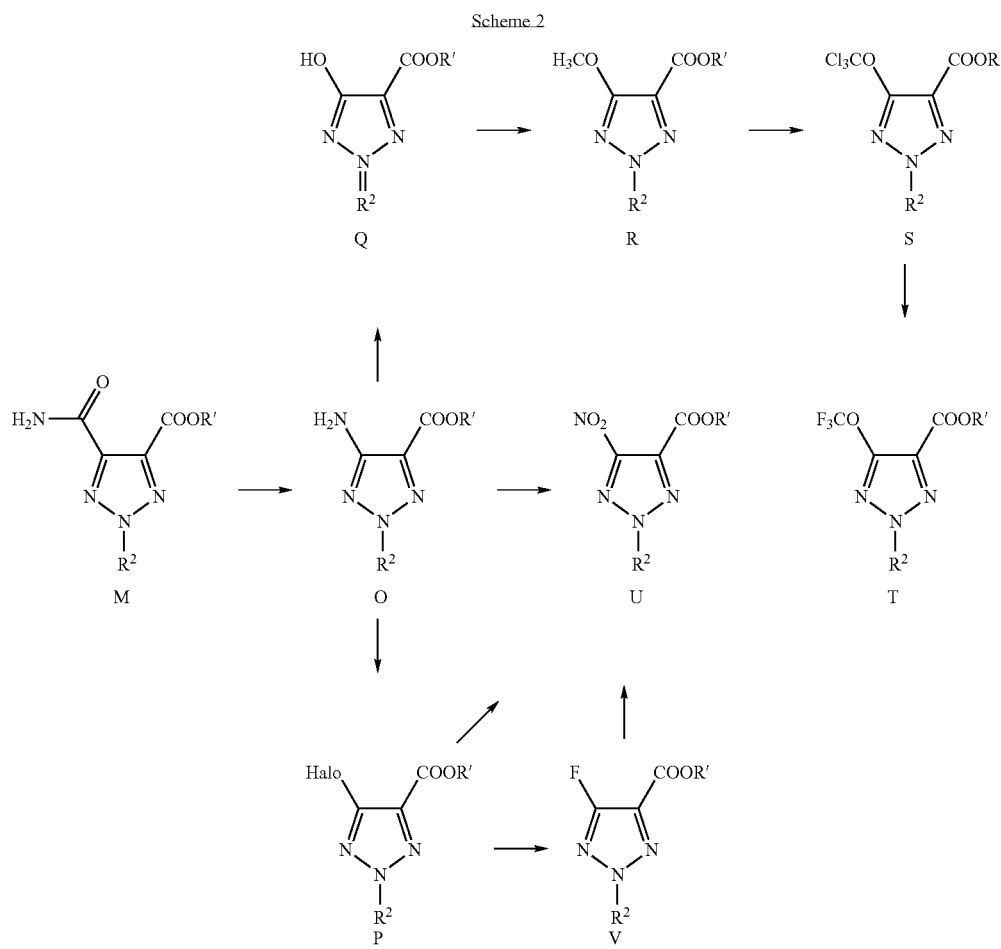

Further transformations to prepare a compound of formula (II) [where $R^1$ and $R^2$ are as defined above for formula (I); Y is OR' and R' is $C_{1-5}$ alkyl] include a Hofmann rearrangement of an amide of formula M with NaOBr or NaOCl in the presence of NaOH to give a 5-amino-1,2,3-triazole of formula O.

Diazotation of a compound of formula O by means of sodium nitrite under aqueous acidic conditions [for example sulphuric acid] or with a nitrite ester [for example (i)-amyl nitrite] in an organic solvent [for example acetone, dichloromethane or THF] in the presence of a halogenide [such as CuCl or CuBr] gives a 5-halo-1,2,3-triazole of formula P [where halo is Cl or Br] which on treatment with a fluorinating agent [such as KF or CsF], preferably in DMF or N-methylpyrrolidone at elevated temperatures, results in a 5-fluoro-1,2,3-triazole of formula V.

By diazotation of a compound of formula O and subsequent acidic aqueous hydrolysis under heating, a 5-hydroxy-1,2,3-triazole of formula Q may be obtained. Treatment of a compound of formula Q with an alkylating agent [such as methyl iodide, dimethylsulphate or dimethylcarbonate] and a base [for example NaH, $K_2CO_3$ or $Na_2CO_3$] in a polar solvent [for example DMF, DMSO or $CH_3CN$] gives a 5-methoxy-1,2,3-triazole of formula R which may be converted to a trichloromethoxy derivative of formula S with a chlorinating agent [such as chlorine] in the presence of azoisobutyronitrile (AIBN) or ultra-violet irradiation at elevated temperature. By treatment of a compound of formula S with a fluorinating agent [for example KF or $SbF_3$] a 5-trifluoromethoxy-1,2,3-triazole of formula T may be prepared.

Oxidation of a compound of formula O with [for example sodium perborate] or treatment according to A. Sudalai et al. [*Angew. Chem. Int. Ed.* 40, 405 (2001)] leads to a 5-nitro derivative of formula U. Alternatively, a compound of formula U may also be obtained by treatment of a compound of formula P or V with $NaNO_2$ in an polar solvent [such as DMF, sulpholane or N-methylpyrrolidone] at elevated temperatures.

Scheme 3

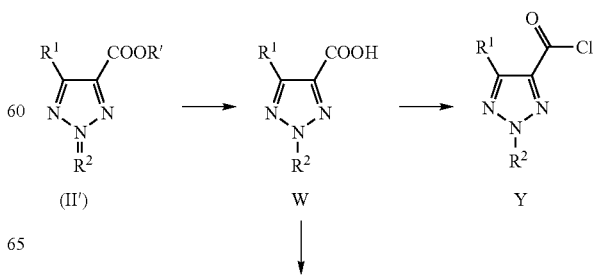

-continued

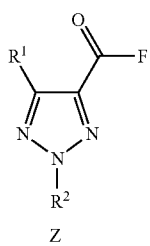
Z

Transformations of a compound of formula (II') [where $R^1$ and $R^2$ are as defined in formula (I); Y is OR'; and R' is $C_{1-5}$ alkyl] to give a compound of formula (II) [where $R^1$ and $R^2$ are as defined in formula (I) and Y is halo or hydroxy] includes saponification with a base [such as KOH or NaOH] in a protic solvent [such as methanol, ethanol or water], at ambient or elevated temperature to give a 1,2,3-triazole-4-carboxylic acid of formula W. Chlorination of a compound of formula W under standard conditions [for example with thionyl chloride, phosgene or oxalyl chloride] yields an acid chloride of formula Y.

Fluorination of a compound of formula W with DAST or $SF_4$ under mild conditions [low to ambient temperatures], preferably in an inert solvent [such as dichloromethane] gives an acid fluoride of formula Z.

(b) Preparation of a Compound of Formula (III).

A compound of formula (III)

$$H_2N-A \quad \text{(III)}$$

where A is as defined above for a compound of formula (I), is useful as an intermediate in the preparation of a compound of formula (I).

Most o-substituted amino-aryls and amino-heteroaryls of formula (III) are known from the literature, but some are novel.

A compound of formula (IIIa) may be obtained according to scheme 4:

Scheme 4

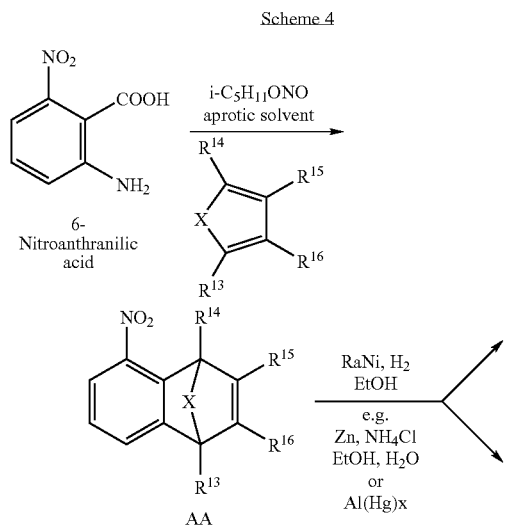

-continued

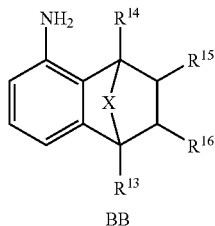
BB

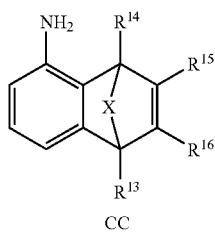
CC

Treatment of an orthlo-substituted nitrobenzonorbornadiene of formula AA (where $R^{13}$, $R^{14}$, $R^{15}$, $R^{16}$ and X are as defined above for a compound of formula (I)) [obtained through Diels-Alder addition of an in situ generated benzyne, for example, starting from a 6-nitroanthranilic acid as described by L. Paquette et al, *J. Amer. Chem. Soc.* 99, 3734 (1977) or from other suitable benzyne precursors (see H. Pellissier et al. *Tetrahedron,* 59, 701 (2003) with a 5-7 membered cyclic 1,4-diene according to, or by analogy to, L. Paquette et al, *J. Amer. Chem. Soc.* 99, 3734 (1977), D. Gravel et al. *Can. J. Chem.* 69, 1193 (1991), J. R. Malpass et al. *Tetrahedron,* 48, 861 (1992), D. E. Lewis et al. *Synthetic Communications,* 23, 993 (1993), R. N. Warrener et al. *Molecules,* 6, 353 (2001), R. N. Warrener et al. *Molecules,* 6, 194 (2001) or I. Fleming et al. *J. Chem. Soc., Perkin Trans.* 1, 2645 (1998)] with Zn, in the presence of ammonium chloride or an aluminium amalgam, in a protic solvent [such ethanol or water] gives an aniline of formula CC, whilst catalytic hydrogenation of a compound of formula AA with, for example, RaNi, Pd/C or Rh/C in the presence of a solvent [for example THF, ethyl acetate, methanol or ethanol] affords an aniline of formula BB.

Compounds of formula (IIIb)

where $R^6$ is an aliphatic or alicyclic, saturated or unsaturated group [in which the group contains three to thirteen carbon atoms and at least one silicon atom and, optionally, one to three heteroatoms, each independently selected from oxygen, nitrogen and sulphur, and the group is optionally substituted by up to four independently selected halogen atoms] and $R^{7-10}$ are as defined in formula (I) may be prepared by analogy with literature examples. References include e.g. E. A. Chemyshew et al., *Bull. Acad. Sci. USSR,* 1960, 1323; K. T. Kang et al., *Tetrahedron Letters,* 32, 4341 (1991), *Synthetic Comm.,* 24, 1507 (1994); M. Murata et al., *Tetrahedron Letters* 40, 9255 (1999); A. Falcou et al., *Tetrahedron* 56, 225 (2000); A.

Arcadi et al., *Tetrahedron Letters* 27, 6397 (1986); K. C. Nicolaou et al., *Chem. Eur. J.* 1, 318 (1995); N. Chatani et al., *J. Org. Chem.* 60, 834 (1995); T. Stuedemann et al., *Tetrahedron* 54, 1299 (1998); P. F. Hurdlik et al., *J. Org. Chem.* 54, 5613 (1989); K. Karabelas et al., *J. Org. Chem.* 51, 5286 (1986); T. Jeffery, *Tetrahedron Letters* 40, 1673 (1999) and *Tetrahedron Letters* 41, 8445 (2000); K. Olofson et al., *J. Org. Chem.* 63, 5076 (1998); H. Uirata et al., *Bull. Chem. Soc. Jap.* 57, 607 (1984); and G. Maas et al., *Tetrahedron* 49, 881 (1983); and references cited therein.

Recent reviews for the introduction of Si-containing functionalities into phenyl derivatives can be found in "The Chemistry of Organosilicon Compounds", Vols. 1-3, S. Patai, Z. Rappaport and Z. Rappaport, Y. Apeloid eds., Wiley 1989, 1998, 2001 and "Houben-Weyl Science and Synthesis", Organometallics Vol. 4, I. Fleming ed., G. Thieme 2002.

Another group of anilines comprises compounds of formula (IIIc)

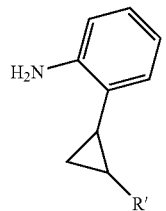

(IIIc)

where R' represents $C_{2-4}$ alkyl, $C_{2-4}$ haloalkyl or $C_{3-6}$ cycloalkyl (itself optionally substituted by up to 3 substituents, independently selected from halo, $C_{1-3}$ alkyl, $C_{1-3}$ haloalkyl and $C_{1-4}$ haloalkoxy).

A compound of formula (IIIc) may be prepared by a reaction sequence starting with a crossed aldol condensation of benzaldehyde with a ketone of formula $CH_3C(O)R'$ [where R' is as defined above for a compound of formula (IIIc)] in the presence of NaOH or KOH in a solvent (such as water or ethanol) and usually under reflux conditions or alternatively by reaction of benzaldehyde with a Wittig reagent under standard conditions. The resulting α,β-unsaturated ketone of formula (IV) [where R' is as defined above for a compound (IIIc)]:

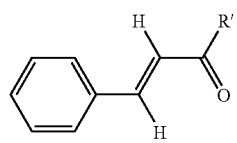

(IV)

may then be converted into a compound of formula (V') [where R' is as defined above for a compound (IIIc)]:

(V')

by reacting first with hydrazine hydrate in ethanol under reflux conditions and then heating (in the range of from 150 to 250° C.) in the presence of KOH (distilling off the solvent). After nitration with $HNO_3$—$H_2O$ or $HNO_3$-acetic anhydride in a cooled vessel (in the range of from −30° C. to 0° C.), the resulting o/p-mixture of a nitrobenzene of formula (VI) [where R' is as defined above for a compound (IIIc)]:

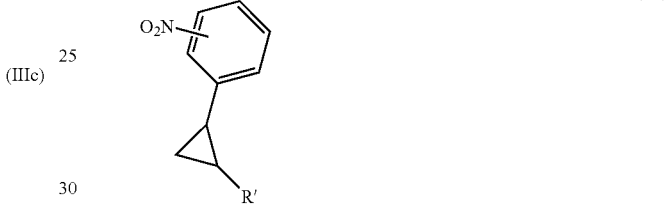

(VI)

may then be separated and catalytically reduced (Pt/C/$H_2$ or Ra—Ni/$H_2$) in a solvent (such as methanol, ethanol of THF) at ambient temperature to give a compound of formula (IIIc).

Alternatively the synthesis of a compound of formula (IIId) [where $R'^a$ is hydrogen or methyl]

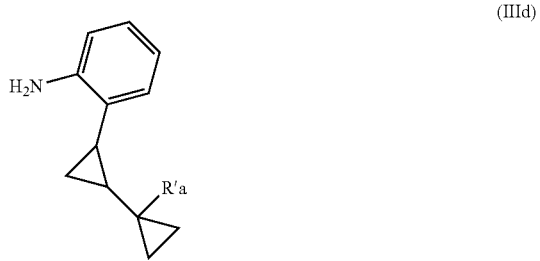

(IIId)

may be accomplished by a reaction sequence started by a Wittig reaction of o-nitrobenzaldehyde with an ylide, prepared from a cyclopropylmethyltriphenylphosphonium bromide in the presence of a strong base [such as NaH] in a solvent [such as DMSO], in the range of 0-85° C. The resulting E/Z-mixture of a compound of formula (VII)

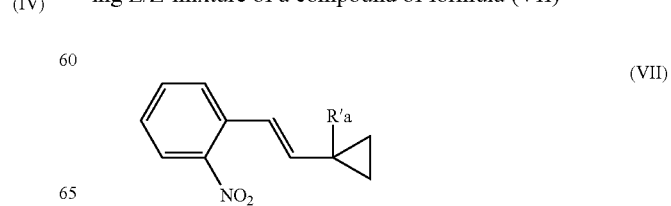

(VII)

[where R'$^a$ is hydrogen or methyl] may be converted to a compound of formula (VIII)

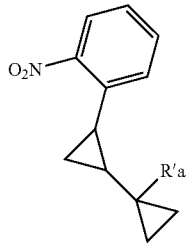

(VIII)

by the application of the Simmons Smith reaction (Zn—Cu, CH$_2$I$_2$, ether as a solvent) to the olefin group of a compound of formula (VII) to give a compound of formula (VIII). The reduction of the nitro moiety of a compound of formula (VIII) to give a compound of formula (IIIc) may be performed by using the same conditions as described above for a compound of formula (VI).

(c) Preparation of a Compound of Formula (I).

Scheme 5

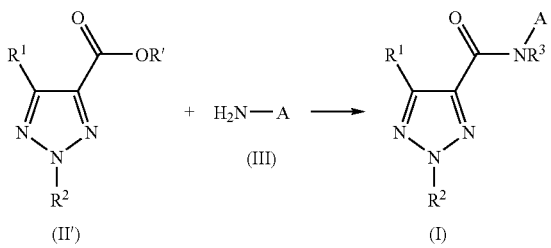

A compound of formula (I) [where A, R$^1$ and R$^2$ are as defined above and R$^3$ is H] may be synthesized by reacting a compound of formula (II') [where R$^1$ and R$^2$ are as defined above and R' is C$_{1-5}$ alkyl] with an aniline of formula (III) [where A is as defined above for a compound of formula (I)] in the presence of NaN(TMS)$_2$ at $-10°$ C. to ambient temperature, preferably in dry THF, as described by J. Wang et al., Synlett, 2001, 1485.

Scheme 6

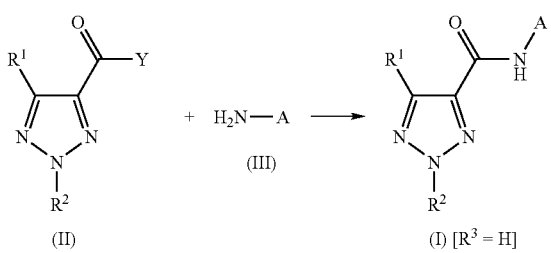

Alternatively, a compound of formula (I) [where A, R$^1$ and R$^2$ are as defined above and R$^3$ is H] may be prepared by reacting a compound of formula (II) [where R$^1$ and R$^2$ are as defined above and Y is OH] with a compound of formula (III) [where A is as defined above for a compound of formula (I)] in the presence of an activating agent [such as BOP-Cl] and two equivalents of a base [such as NEt$_3$] or by reacting a compound of formula (II) [where Y is Cl, Br or F] with a compound of formula (III) in the presence of one equivalent of a base [such as NEt$_3$, NaHCO$_3$, KHCO$_3$, Na$_2$CO$_3$ or K$_2$CO$_3$] in a solvent [such as dichloromethane, ethyl acetate or DMF] preferably at $-10$ to $30°$ C.

Scheme 7

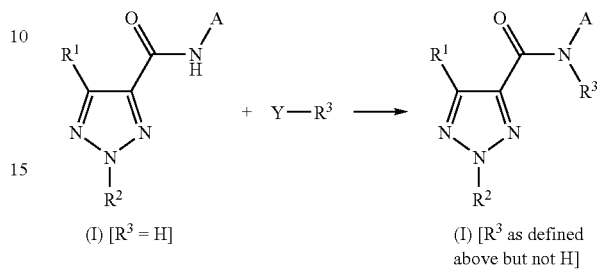

A compound of formula (I) [where R$^3$ is as defined above for formula (I), except that it is not hydrogen] may be prepared by reacting a compound of formula (I) [where R$^3$ is hydrogen] with a species Y—R$^3$ [where R$^3$ is as defined for formula (I), except that it is not hydrogen; and Y is halogen, preferably Cl, Br or I; or Y is such that Y—R$^3$ is an anhydride: that is, when R$^3$ is COR*, Y is OCOR*] in the presence of a base [for example NaH, NEt$_3$, NaHCO$_3$ or K$_2$CO$_3$] in an appropriate solvent [such as ethyl acetate] or in a biphasic mixture [such as dichloromethane/water mixturte], at $-10$ to $30°$ C.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later, for example from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Altemaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora,*

*Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound No. 1.15 [2-methyl-5-trifluoromethyl-2H-1,2,3-triazole-4-carboxylic acid methyl ester] and Compound No. 1.13 [2-methyl-5-trifluoromethyl-2H-1,2,3-triazole-4-carboxylic acid].

a) Preparation of 2-methyl-2H-1,2,3-triazole-4,5-dicarboxylic acid dimethylester and 1-methyl-1H-1,23-triazole-4,5-dicarboxylic acid dimethylester 1,2,3-Triazole-4,5-dicarboxylic acid dimethyl ester (Y. Tanaka et al. *Tetrahedron* 29, 3271 (1973)) (74.06 g; 0.40 mol), potassium carbonate (110.57 g; 0.80 mol) and methyl iodide (73.81 g; 0.52 mol) were reacted in acetonitrile (1000 ml) at 40° C. for 20 minutes and then for 20 hours at ambient temperature. The mixture was poured onto ice-water and extracted with ether to give the crude product (70.66 g) as a mixture of isomers. Separation on silica gel in ethyl acetate-hexane (2:3) yielded 36.51 g (46%) of 2-methyl-2H-1,2,3-triazole-4,5-dicarboxylic acid dimethylester [m.p. 86-87° C.; $^1$H-NMR (300 MHz, DMSO-d$_6$), δ(ppm): 4.27(s,3H), 3.88 (s,6H)] and 26.92 g (34%) of 1-methyl-1H-1,2,3-triazole-4,5-dicarboxylic dimethylester [m.p. 63-64° C.; $^1$H-NMR (300 MHz, DMSO-d$_6$), δ(ppm): 4.19(s,3H), 3.93(s,3H), 3.87(s,3H)].

b) Preparation of 2-methyl-2H-1,2,3-triazole-4,5-dicarboxylic acid monomethyl ester To a solution of 2-methyl-2H-1,2,3-triazole-4,5-dicarboxylic acid dimethylester (1.2 g; 6 mmol) in 30 ml methanol was added 358 mg KOH (assay 86%; 5.5 mmol). The mixture was heated at reflux temperature for 48 hours. The solvent was evaporated and the residue was then taken into water and extracted with ethyl acetate (3 times). The combined organic phases contained non-reacted starting material. The aqueous phase was acidified with 2N HCl (pH2-3) and extracted with ethyl acetate (3 times). The extracts were combined, dried (anhydrous MgSO4) and evaporated to dryness to give 803 mg (72%) of the desired compound (m.p. 125-126° C.; $^1$H-NMR (300 MHz, DMSO-d$_6$), δ(ppm): 13.7(br.s,1H, exchangable with D$_2$O), 4.24(s,3H), 3.84(s,3H).

c) Preparation of 2-methyl-5-trifluoromethyl-2H-1,2,3-triazole-4-carboxylic acid methyl ester [Compound Number 1.15]

2-Methyl-2H-1,2,3-triazole-4,5-dicarboxylic acid monomethyl ester (2.9 g; 15.66 mmol) and dichloromethane (160 ml) were placed in an 0.3 litre monel autoclave. Under an inert atmosphere and cooling with dry ice, gaseous HF (27 g) was introduced at −50° C. followed by gaseous SF$_4$ (distilled, 6.9 g; 64.23 mmol). The autoclave was heated to 80° C. for 6 hours. The maximum pressure amounted 9.8 bar. After cooling to ambient temperature the reaction mixture was poured onto ice-dichloromethane and adjusted to pH7 with aqueous NaHCO$_3$. Extraction with dichloromethane (3 times), drying over Na$_2$SO$_4$ and evaporation under reduced pressure afforded the crude product. Purification by Kugelrohr-distillation at 3 mbar and ca. 180° C. gave 2.8 g (85%) of Compound No. 1.15 as a yellowish liquid.

$^1$H-NMR (300 MHz, CDCl$_3$), δ(ppm): 4.29(s,3H), 3.97(s, 3H);

$^{19}$F-NMR (235 MHz, CDCl$_3$), δ (ppm): −61.7.

$^{13}$C-NMR (125 MHz, CDCl$_3$), δ(ppm): 159.05, 139.65 (q, J$_{C(5)F}$=40.8 Hz), 137.20, 119.63 (q, J$_{CF}$=269.4 Hz, CF$_3$), 52.96, 43.01.

d) Preparation of 2-methyl-5-trifluoromethyl-2H-1,2,3-triazole-4-carboxylic acid [Compound Number 1.13]

A solution of 2-methyl-5-trifluoromethyl-2H-1,2,3-triazole-4-carboxylic acid methyl ester [Compound Number 1.15] (2.09 g; 0.01 mol) and KOH (86%; 0.783 g; 1.2 eq.) in THF (50 ml) was heated at reflux temperature for 3.5 hours. The solution was evaporated, the residue was dissolved in water and acidified to pH 1-2 with HCl (1M). Evaporation of the aqueous solution followed by continuous extration in ethylacetate for 20 hours gave of Compound No 1.13 (2.11 g; 100%) as a crystalline solid.

$^1$H-NMR (400 MHz, DMSO-d$_6$), δ(ppm): 4.19(s,3H).

$^{19}$F-NMR (235 MHz, DMSO-d$_6$), δ (ppm): −59.3.

$^{13}$C-NMR (125 MHz, DMSO-d$_6$), δ(ppm): 160.74, 144.08, 135.81 (q, J$_{C(5)F}$=38.1 Hz), 120.63 (q, J$_{CF}$=268.4 Hz, CF$_3$), 42.20.

EXAMPLE 2

This Example illustrates the preparation of Compound No. 1.03 [2-methyl-5-difluoromethyl-2H-1,2,3-triazole-5-carboxylic acid methyl ester].

a) Preparation of 5-Chlorocarbonyl-2-methyl-2H-1,2,3-triazole-4-carboxylic acid methyl ester Methyl 2-methyl-1,2,3-triazole-4,5-dicarboxylate (2.3 g; 0.011 mol) was reacted with oxalyl chloride (1.46 ml; 0.014 mol) plus two drops of DMF in dichloromethane (20 ml) at 20° C. When the vigourous reaction ceased the temperature was raised to reflux for 15 hours. The mixture was evaporated to dryness to give 2.7 g of the acid chloride as a solid. $^1$H-NMR (300 MHz, CDCl$_3$), δ (ppm): 4.48(s, H), 4.0(s,3H).

b) Preparation of 5-formyl-2-methyl-2H-1,2,3-triazole-4-carboxylic acid methyl ester To a solution of freshly prepared 5-Chlorocarbonyl-2-methyl-2H-1,2,3-triazole-4-carboxylic acid methyl ester (2.7 g; ca. 13 mmol) in THF (270 ml) was added ethyl-diisopropylamine (1.88 g; 1.1 eq.). The mixture was hydrogenated in the presence of 2.7 g 10% Pd/C at 0-5° C. at normal pressure for 2½ hours and subsequently filtered from the catalyst. The clear solution was evaporated to give the crude as a solid which was dissolved again in ethyl acetate and stirred for a couple of minutes with silica gel. After filtration and evaporation 1.77 g (84%) of pure product as off-white crystals were obtained [m.p. 107-108° C.; $^1$H-NMR (300 MHz, CDCl$_3$), δ (ppm): 10.43(s,1H), 4.33(s,3H), 4.01(s,3H)].

c) Preparation of 2-methyl-5-difluoromethyl-2H-1,2,3-triazole-5-carboxylic acid methyl ester. [Compound No. 1.03.]

5-Formyl-2-methyl-2H-1,2,3-triazole-4-carboxylic acid methyl ester (600 mg; 3.5 mmol) in 0.5 ml CHCl$_3$ were reacted with (bis(2-methoxyethyl)amino)sulfurtrifluoride (1350 mg; 6.1 mmol) at ambient temperature to 50° C. for 6 days. The resulting orange solution was carefully quenched with 6 ml of a saturated aqueous NaHCO$_3$ solution (vigorous reaction) and extracted with ethyl acetate (twice). The combined organic phases were washed with aqueous NaHCO$_3$-solution, dried over anhydrous MgSO$_4$ and evaporated to give 351 mg (52%) of colourless crystals.

$^1$H-NMR (300 MHz, CDCl$_3$), δ (ppm): 7.15(t, J$_{HF}$=53.5 Hz, 1H, H—CF$_2$), 4.30(s,3H), 3.98(s,3H); $^{19}$F-NMR (235 MHz, CDCl$_3$), δ (ppm): −116.1; $^{13}$C-NMR (125 MHz, CDCl$_3$), δ (ppm): 160.0, 143.6(t, J$_{C(5)F}$=25.6 Hz), 137.2, 108.0(t, J$_{(CF)}$=237.8 Hz, CHF$_2$), 52.6, 42.7].

EXAMPLE 3

This Example illustrates the preparation of Compound No. 1.50 [2-methyl-5-fluoromethyl-2H-1,2,3-triazole-5-carboxylic acid methyl ester].

a) Preparation of 5-hydroxymethyl-2-methyl-2H-1,2,3-triazole-4-carboxylic acid methyl ester 2.6 g (13.3 mmol) of 5-formyl-2-methyl-2H-1,2,3-triazole-4-carboxylic acid methyl ester (see Example 2a) in methanol (100 ml) was treated with NaBH$_4$ (601 mg) under stirring for 1 hour at ambient temperature. The reaction mixture was quenched with saturated aqueous ammonium chloride solution, extracted with ethyl acetate, dried with Na$_2$SO$_4$ and evaporated to give the crude as an oil. Purification on silica gel in ethyl acetate:hexane (2:1) yielded 1.85 g (81%) of the crystalline product, m.p. 112-113° C.

$^1$H-NMR (300 MHz, CDCl$_3$), δ (ppm): 4.86(d, J=6.9 Hz, 1H), 4.22(s,3H), 3.98(s,3H), 3.53(t; J=6.9 Hz, exchangeable with D$_2$O).

b) Preparation of 2-methyl-5-fluoromethyl-2H-1,2,3-triazole-5-carboxylic acid methyl ester. [Compound No. 1.50.]

A solution of 5-hydroxymethyl-2-methyl-2H-1,2,3-triazole-4-carboxylic acid methyl ester (200 mg; 1.1 mmol) in CH$_2$Cl$_2$ (15 ml) was reacted with 0.26 ml diethylamino sulfur trifluoride (2 mmol) for 15 minutes at −40° C. followed by 15 hours at ambient temperature. After evaporation, the crude product was purified on silica gel in ethyl acetate:hexane (3:1) to give 181 mg (95%) of the desired product, m.p. 64-66° C.

$^1$H-NMR (300 MHz, CDCl$_3$), δ (ppm): 5.66(d, J$_{HF}$=47.5 Hz, 2H, H$_2$—CF), 4.26(s,3H), 3.96(s,3H).

$^{19}$F-NMR (235 MHz, CDCl$_3$), δ (ppm): −214.

$^{13}$C-NMR (125 MHz, CDCl$_3$), δ (ppm): 161.6, 145.86 (d, J$_{C(5)F}$=18.7 Hz), 137.09, 74.82(d, J$_{CF}$=166.6 Hz, CH$_2$F), 52.2, 42.3.

EXAMPLE 4

This Example illustrates the preparation of Compound No. 3.017 [5-difluoromethyl-2-methyl-2H-1,2,3-triazole-4-carboxylic acid (4'-chloro-biphenyl-2-yl)-amide].

To a solution of 2-methyl-5-difluoromethyl-2H-1,2,3-triazole-5-carboxylic acid methyl ester (300 mg; 1.57 mmol) and 4'-chloro-biphenyl-2-ylamine (320 mg; 1.57 mmol) in THF (3 ml) was added sodium bis(trimethylsilyl)-amide (0.88 ml 2M in THF; 1.76 mmol; 1.12 eq.) by syringe at 0° C. over 1.5 minutes. The reaction mixture was stirred at 0° C. for 15 minutes and then at ambient temperature for 22 hours. It was then poured on cold saturated NH$_4$Cl solution and extracted with ethyl acetate. After washing with brine it was dried (anhydrous MgSO$_4$) and evaporated to dryness to give a solid, which was triturated with hexane. The colourless crystalline product was filtered and dried: 300 mg (53%) [m.p. 155-156° C.; 1H-NMR (300 MHz, CDCl$_3$), δ (ppm): 8.5(br, exchangeable with D$_2$O, 1H), 8.4 (d, 1H), 7.5-7.2(m,7H), 7.38 (t, J$_{HF}$=52.5 Hz, 1H, CHF$_2$), 4.2(s,3H), LC-MS: 363(M+H)].

EXAMPLE 5

This Example illustrates the preparation of Compound No. 2.219 [2-methyl-5-trifluoromethyl-2H-1,2,3-triazole-4-carboxylic acid [2-(1,3-dimethyl-butyl)-phenyl]-amide].

To a solution of 2-methyl-5-trifluoromethyl-2H-1,2,3-triazole-4-carboxylic acid methyl ester (1150 mg; 0.75 mmol) and 2-(1,3-dimethyl-butyl)-phenylamine (133 mg; 0.75 mmol) in 1.5 ml THF was added sodium bis(trimethylsilyl)-amide (0.638 ml 2M in THF; 1.7 eq.) by syringe at ambient temperature. The reaction mixture was stirred for 20 hours and was then poured on cold saturated NH$_4$Cl solution and extracted with ethyl acetate. After washing with brine it was dried (anhydrous MgSO$_4$) and evaporated to dryness to give the crude product, which was purified on silica gel in cyclohexane-ethyl acetate (18:1) The crystalline product was triturated in hexane, filtered and dried in vacuo to yield 130 mg (49%) of Compound No. 2.219 [mp 94.6-95.4° C.; 1H-NMR (300 MHz, CDCl$_3$), δ (ppm): 8.5(br.s, exchangeable with D$_2$O,1H), 8.0(d,1H), 7.3-7.15(m,3H), 4.33(s,3H), 3.0(m, 1H), 1.55-1.35(m,3H), 1.26(d,3H), 0.9(2d,6H); LC-MS: 355.6(M+H)].

EXAMPLE 6

This Example illustrates the preparation of Compound No. 26.014 [1,8-Dimethyl-11-oxa-tricyclo[6.2.1.0*2.7*]undeca-2,4,6-trien-3-yl-amine].

A solution of 1,4-dimethyl-5-nitro-1,4-dihydro-1,4-epoxynaphthalene (5.49 g; 25.27 mmol) (see T. Nishiyama et al., *Rikagaku-hen*, 28, 37-43 (2000)) in 55 ml THF was hydrogenated in the presence of RaNi (1.1 g) at ambient temparature. Hydrogen uptake was 2.23 litre (97%) after 18 hours. After filtering off the catalyst, the filtrate was evaporated and taken into ether, washed with aqueous NaHCO$_3$-solution and dried (NaSO$_4$) to give 4.60 g of crude product, as an oil. Trituration with hexane and a trace of ether furnished a total of 4.5 g (94%) of reddish crystalline product, m.p. 92-93° C.

$^1$H-NMR (300 MHz, CDCl$_3$), δ (ppm): 7.05(t,1H), 6.7(t, 2H), ca.5(br., exchangeable with D$_2$O, 2H), 2.0(s,3H), 1.9(m, 2H), 1.8(s,3H), 1.7(m,1H), 1.5(m,1H).

EXAMPLE 7

This Example illustrates the preparation of Compound No. 26.001 [1,8-Dimethyl-11-oxa-tricyclo[6.2.1.0*2.7*]undeca-2,4,6,9-tetraen-3-yl-anine].

To 1,4-dimethyl-5-nitro-1,4-dihydro-1,4-epoxynaphthalene (4.22 g; 19.43 mmol) (see Example 6) in ethanol (60 ml) was added a solution of ammoniumchloride (2.08 g) in H$_2$O (5.2 ml) at 47° C. Under vigorous stirring, zinc powder (9.10 g; 0.14 mol) was added in portions over a period of 5 minutes.

The suspension was heated to reflux for 5½ hours followed by filtration through Hyflo™ to give a clear yellow filtrate. After evaporation, the crude product amounted 4.57 g, as a viscous oil. Column chromatography on silica gel in ethyl acetate-hexane (1:4) gave 1.24 g (34%) of the desired product, as brownish crystals, m.p. 92-96° C.

$^1$H-NMR (300 MHz, CDCl$_3$), δ(ppm): 6.85 and 6.7(two m, 2×2H), 6.47(t,1H), ca.5-3 (br., exchangeable with D$_2$O,2H), 2.07(s,3H), 1.85(s,3H).

FORMULATION EXAMPLES FOR COMPOUNDS OF FORMULA (I)

Working procedures for preparing formulations of the compounds of formula I such as Emulsifiable Concentrates, Solutions, Granules, Dusts and Wettable Powders are described in WO97/33890.

BIOLOGICAL EXAMPLES

FUNGICIDAL ACTIONS

Example B-1

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension (1×10$^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Infestation is prevented virtually completely (0-5% infestation) with each of Compounds 2.273, 3.219, 3.273, 3.321, 8.189, 9.189, 20.017, 20.022, 21.017 and 21.022.

Example B-2

Action Against *Podosphaera leucotricha*/Apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds 2.005, 3.017, 3.219 and 9.189 each exhibit strong efficacy (<20% infestation).

Example B-3

Action Against *Venturia inaegualis*/Apple (Scab on Apple)

4 week old apple seedlings cv. McIntosh are treated with the formulated test compound (0.02% active ingredient) in a spray chamber. One day after application, the apple plants are inoculated by spraying a spore suspension (4×10$^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds 3.017, 3.219 and 9.189 each exhibit strong efficacy (<20% infestation).

Example B-4

Action against *Erysiphe graminis*/Barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Compounds 2.017, 2.029, 2.273, 3.005, 3.017, 3.029, 3.067, 3.070, 3.219, 3.273, 3.321, 3.407, 8.189, 9.189 and 21.017 each exhibit strong efficacy (<20% infestation).

Example B-5

Action Against *Botrytis cinerea*/Grape (*Botrytis* on Gapes)

5 week old grape seedlings cv. Gutedel are treated with the formulated test compound (0.02% active ingredient) in a spray chamber. Two days after application, the grape plants are inoculated by spraying a spore suspension (1×10$^6$ conidia/ml) on the test plants. After an incubation period of 4 days at 21° C. and 95% r.h. in a greenhouse the disease incidence is assessed.

Compounds 2.029, 3.017 and 3.219 each show good activity in this test (<50% disease incidence).

Example B-6

Action Against *Botrytis cinerea*/Tomato (*Botrytis* on Tomatoes)

4 week old tomato plants cv. Roter Gnom are treated with the formulated test compound (0.02% active ingredient) in a spray chamber. Two days after application, the tomato plants are inoculated by spraying a spore suspension (1×10$^5$ conidia/ml) on the test plants. After an incubation period of 4 days at 20° C. and 95% r.h. in a growth chamber the disease incidence is assessed.

Compounds 2.029, 3.005, 3.029, 3.067, 3.070, 3.219, 3.273, 9.189 and 20.017 each exhibit good efficacy (<50% disease incidence).

Example B-7

Action Against *Seotoria nodorum*/Wheat (*Septoria* Leaf Spot on Wheat)

1 week old wheat plants cv. Arina are treated with the formulated test compound (0.02% active ingredient) in a spray chamber. One day after application, the wheat plants are inoculated by spraying a spore suspension (5×10$^5$ conidia/ml) on the test plants. After an incubation period of 1 day at 20° C. and 95% r.h. the plants are kept for 10 days at 20° C. and 60% r.h. in a greenhouse. The disease incidence is assessed 11 days after inoculation.

Compounds 3.273 and 9.189 each show good activity in this test (<50% disease incidence).

Example B-8

Action Against *Helminthosporium teres*/Barley (Net Blotch on Barley 1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% r.h. in a greenhouse the disease incidence is assessed.

Compounds 2.005, 2.017, 2.029, 2.067, 2.070, 2.273, 3.005, 3.017, 3.029, 3.067, 3.070, 3.219, 3.407, 9.189 and 21.017 each show good activity in this test (<20% disease incidence).

Example B-9

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Compounds 2.005, 2.029, 3.005, 3.017, 3.029 and 9.189 each show good activity in this test (<20% disease incidence).

Example B-10

Action Against *Uncinula necator*/Grape (Powdery Mildew on Gapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Compounds 3.017, 3.219 and 9.189 each show good activity in this test (<20% disease incidence).

The invention claimed is:

1. A compound of formula (I):

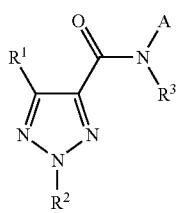

(I)

where A is an ortho-substituted ring selected from formulae (A1) to (A22);

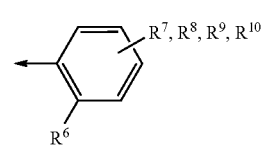
(A1)

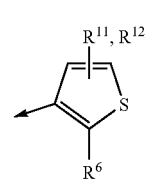
(A2)

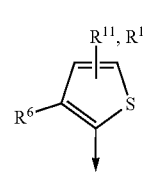
(A3)

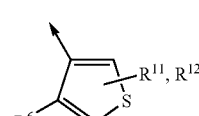
(A4)

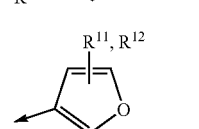
(A5)

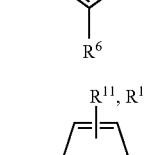
(A6)

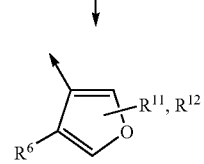
(A7)

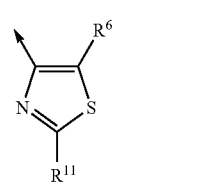
(A8)

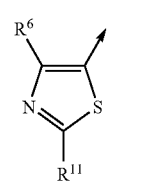
(A9)

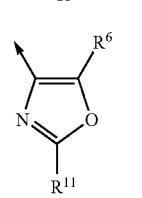
(A10)

-continued

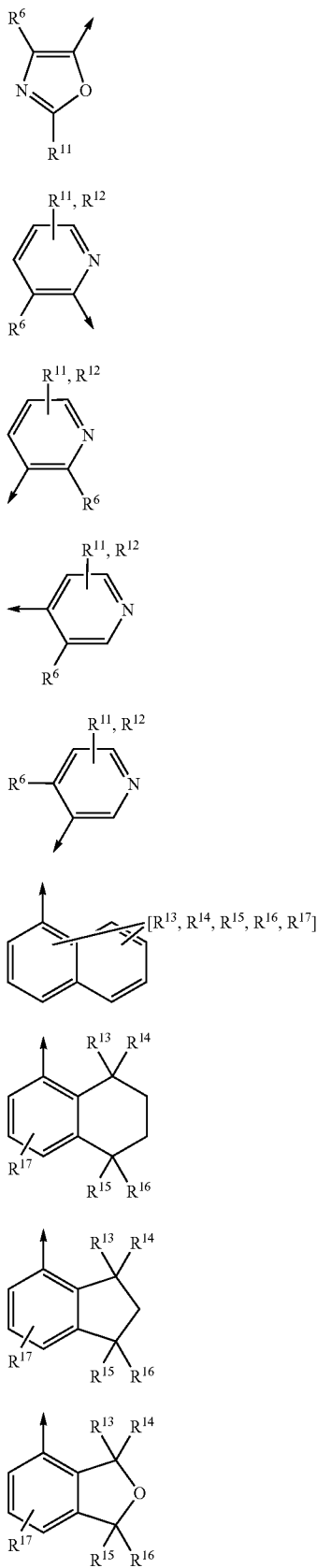

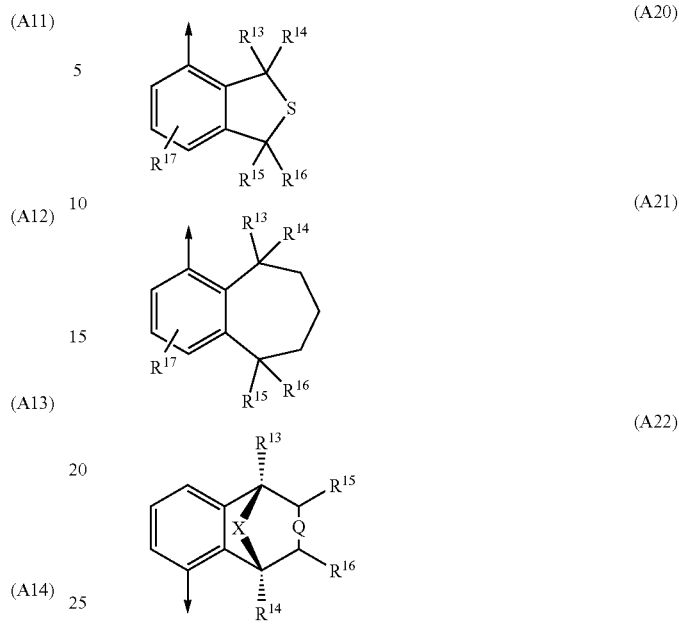

Q is a single or a double bond; X is O, N($R^{18}$), S or C$R^{19}R^{20}$) (C$R^{21}R^{22}$)$_m$(C$R^{23}R^{24}$)$_n$; $R^1$ is halogen, cyano, nitro, $C_{1-4}$ alkyl, $C_{1-4}$ haloalkyl, $C_{1-4}$ alkoxy, $C_{1-4}$ haloalkoxy or optionally substituted $C_{2-4}$ alkenyl, optionally substituted $C_{2-4}$ alkynyl or optionally substituted $SO_2(C_{1-4})$alkyl (where the optionally substituted moieties may each have up to 3 substituents, each independently selected from halogen and $C_{1-4}$alkoxy); $R^2$ is $C_{1-4}$alkyl, $C_{1-4}$ haloalkyl, $C_{1-4}$ alkoxy($C_{1-4}$)alkyl or $C_{1-4}$ alkylthio($C_{1-4}$)alkyl or optionally substituted aryl ($C_{1-4}$)alkyl- or [optionally substituted aryl] oxy($C_{1-4}$)alkyl- (where the optionally substituted aryl moieties may each have up to 3 substituents, each independently selected from halogen and $C_{1-4}$ alkoxy); $R^3$ is hydrogen, $CH_2C\!\!=\!\!CR^4$, $CH_2CR^4\!\!=\!\!C(H)R^4$, CH=C=$CH_2$ or CO$R^5$ or optionally substituted $C_{1-4}$alkyl, optionally substituted $C_{1-4}$ alkoxy or optionally substituted ($C_{1-4}$)alkylC(=O)O (where the optionally substituted moieties may each have up to 3 substituents, each independently selected from halogen, $C_{1-4}$alkoxy, $C_{1-4}$ alkyl, $C_{1-2}$ haloalkoxy, hydroxy, cyano, carboxyl, methoxycarbonyl, ethoxycarbonyl, methylsulfonyl and ethylsulfonyl); each $R^4$ is, independently, hydrogen, halogen, $C_{1-4}$ alkyl, $C_{1-4}$ haloalkyl, $C_{1-4}$ alkoxy or $C_{1-4}$ alkoxy ($C_{1-4}$)alkyl; $R^5$ is hydrogen or optionally substituted $C_{1-6}$ alkyl, optionally substituted $C_{1-4}$ alkoxy, optionally substituted $C_{1-4}$ alkoxy($C_{1-4}$)alkyl, optionally substituted $C_{1-4}$ alkylthio($C_{1-4}$)alkyl or optionally substituted aryl (where the optionally substituted moieties may each have up to 3 substituents, each independently selected from halogen, $C_{1-6}$ alkoxy, $C_{1-6}$ haloalkoxy, cyano, hydroxy, methoxycarbonyl and ethoxycarbonyl); $R^6$ is
  i) phenyl optionally substituted by up to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), (Z)pC=C$R_{25}$ and (Z)pC$R_{28}$=C$R_{26}R_{27}$;
  ii) a 5-6 membered heterocyclic ring in which the ring contains 1 to 3 heteroatoms (each independently chosen from oxygen, sulphur and nitrogen) and the ring is optionally substituted by up to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C(H)=N-O-(C_{1-6}$ alkyl) and $C(C_{1-6}$ alkyl)cyano, $C_{1-4}$ alkoxy, $C_{1-4}$ thioalkyl, $COO-C_{1-4}$ alkyl, $=N-OH$, $=N-O-(C_1-4$ alkyl), $C_{3-8}$ cycloalkyl (itself optionally substituted by up to 3 substituents, each independently selected from $C_{1-4}$ alkyl, halogen, $C_{1-4}$ alkoxy and $C_{1-4}$ haloalkoxy) and $C_{4-8}$ cycloalkenyl (itself optionally substituted by up to 3 substituents, each independently selected from $C_{1-4}$ alkyl, halogen, $C_{1-4}$ alkoxy and $C_{1-4}$ haloalkoxy);

iii) $C_{2-12}$ alkenyl optionally substituted by up to 6 substituents, each independently selected from halogen, cyano, $C_{1-4}$ alkoxy, $C_{1-4}$ thioalkyl, $COO-(C_{1-4}$ alkyl), $=N-OH$, $=N-O-(C_{1-4}$ alkyl), $C_{3-8}$ cycloalkyl (itself optionally substituted by up to 3 substituents, each independently selected from $C_{1-4}$ alkyl, halogen, $C_{1-4}$alkoxy and $C_{1-4}$ haloalkoxy) and $C_{4-8}$ cycloalkenyl (itself optionally substituted by up to 3 substituents, each independently selected from $C_{1-4}$ alkyl, halogen, $C_{1-4}$ alkoxy and $C_{1-4}$ haloalkoxy);

iv) $C_{2-12}$ alkynyl optionally substituted by up to 6 substituents, each independently selected from halogen, cyano, $C_{1-4}$ alkoxy, $C_{1-4}$ thioalkyl, $COO-C_{1-4}$ alkyl, $=N-OH$, $=H-O-(C_{1-4}$ alkyl), $C_{3-8}$ cycloalkyl (itself optionally substituted by up to 3 substituents, each independently selected from $C_{1-4}$ alkyl, halogen, $C_{1-4}$ alkoxy and $C_{1-4}$ haloalkoxy), $Si(CH_3)_3$ and $C_{4-8}$ cycloalkenyl (itself optionally substituted by up to 3 substituents, each independently selected from $C_{1-4}$ alkyl, halogen, $C_{1-4}$ alkoxy and $C_{1-4}$ haloalkoxy);

v) $C_{3-8}$ cycloalkyl optionally substituted by up to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl (itself optionally substituted by up to 3 substituents, each independently selected from $C_{1-4}$ alkyl, halogen, $C_{1-4}$ alkoxy and $C_{1-4}$ haloalkoxy) and phenyl (itself optionally substituted by up to five independently selected halogen atoms);

vi) $C_{4-8}$ cycloalkenyl optionally substituted by up to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl (itself optionally substituted by up to 3 substituents, each independently selected from $C_{1-4}$ alkyl, halogen, $C_{1-4}$alkoxy and $C_{1-4}$ haloalkoxy) and phenyl (itself optionally substituted by up to five independently selected halogen atoms);

vii) $C_{6-12}$ bicycloalkyl optionally substituted by up to 3 substituents, each independently selected from halogen, $C_{1-4}$ alkyl and $C_{1-4}$ haloalkyl; or viii) an aliphatic, saturated or unsaturated group in which the group contains three to thirteen carbon atoms and at least one silicon atom and, optionally, one to three heteroatoms, each independently selected from oxygen, nitrogen and sulphur, and the group is optionally substituted by up to four independently selected halogen atoms;

$R^7$, $R^8$, $R^9$, $R^{10}$, $R^{11}$ and $R^{12}$ are each, independently, hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl or $C_{1-4}$ thiohaloalkyl; $R^{13}$, $R^{14}$, $R^{15}$, $R^{16}$ and $R^{17}$ are each, independently, hydrogen, halogen, $C_{1-4}$ alkyl, $C(O)CH_3$, $C_{1-4}$ haloalkyl, $C_{1-4}$ alkoxy, $C_{1-4}$ haloalkoxy, $C_{1-4}$ thioalkyl, $C_{1-4}$ thiohaloalkyl, hydroxymethyl or $C_{1-}$ alkoxymethyl; $R^{18}$ is hydrogen, $C_{1-4}$ alkyl, $C_{1-4}$ alkoxy $(C_{1-4})$alkyl, formyl, $C(=O)C_{1-4}$alkyl (optionally substituted by halogen or $C_{1-4}$ alkoxy) or $C(=O)O-C_{1-6}$ alkyl (optionally substituted by halogen, $C_{1-4}$ alkoxy or CN); $R^{19}$, $R^{20}$, $R^{21}$, $R^{22}$, $R^{23}$ and $R^{24}$ are each, independently, $C_{1-6}$ alkyl, $C_{1-6}$ alkenyl both optionally substituted by halogen, hydroxy, $=O$, $C_{1-4}$ alkoxy, $O-C(O)-C_{1-4}$ alkyl, aryl or a 3-7 membered carbocyclic ring (itself optionally substituted by up to three methyl groups), a 3-7 membered carbocyclic ring (optionally substituted by up to three methyl groups and optionally containing one heteroatom selected from nitrogen and oxygen), hydrogen, halogen, hydroxy or $C_{1-4}$ alkoxy; or $R^{19}R^{20}$ together with the carbon atom to which they are attached form a carbonyl-group, a 3-5 membered carbocyclic ring (optionally substituted by up to three methyl groups), $C_{1-6}$ alkylidene (optionally substituted by up to three methyl groups) or $C_{3-6}$ cycloalkylidene (optionally substituted by up to three methyl groups); $R^{25}$ is hydrogen, halogen, $C_{1-4}$ alkyl, $C_{1-4}$ haloalkyl, $C_{1-4}$ alkoxy$(C_{1-4})$alkyl, $C_{1-4}$ haloalkoxy$(C_{1-4})$alkyl or $Si(C_{1-4}$ alkyl$)_3$; $R^{26}$ and $R^{27}$ are each, independently, hydrogen, halogen, $C_{1-4}$ alkyl or $C_{1-4}$ haloalkyl; $R^{28}$ is hydrogen, $C_{1-4}$ alkyl or $C_{1-4}$ haloalkyl; m is 0 or 1; n is 0 or 1; p is 0 or 1; and Z is $C_{1-4}$ alkylene.

2. A compound of formula (I) according to claim 1, where A is selected from formulae (A1), (A2), (A3), (A16), (A17), (A18), (A19), (A20) and (A22).

3. A compound of formula (I) according to claim 1, where $R^1$ is $C_{1-4}$ alkyl, $C_{1-4}$ haloalkyl, $NO_2$, CN or $OCF_3$.

4. A compound of formula (I) according to claim 1, where $R^2$ is $C_{1-4}$ alkyl, $C_{1-4}$ haloalkyl, $C_{1-4}$ alkoxy$(C_{1-4})$alkyl or $C_{1-4}$ alkylthio$(C_{1-4})$alkyl.

5. A compound of formula (I) according to claim 1, where $R^3$ is hydrogen, $CH_2C=CR^4$, $CH_2CR^4=C(H)R^4$, $CH=C=CH_2$ or $COR^5$.

6. A composition comprising a compound of formula (I) according to claim 1, together with a suitable carrier.

7. A method of controlling or preventing infestation of cultivated plants by fungi by application of a compound of formula (I) according to claim 1, to plants, to parts thereof or the locus thereof.

* * * * *